US011268108B2

(12) United States Patent
Ammendola et al.

(10) Patent No.: US 11,268,108 B2
(45) Date of Patent: Mar. 8, 2022

(54) REPLICATION COMPETENT ADENOVIRAL VECTORS

(71) Applicant: GLAXOSMITHKLINE BIOLOGICALS SA, Rixensart (BE)

(72) Inventors: Virginia Ammendola, Rome (IT); Stefano Colloca, Rome (IT); Alessandra Vitelli, Rome (IT)

(73) Assignee: GLAXOSMITHKLINE BIOLOGICALS SA, Rixensart (BE)

( * ) Notice: Subject to any disclaimer, the term of this patent is extended or adjusted under 35 U.S.C. 154(b) by 0 days.

(21) Appl. No.: 16/756,376

(22) PCT Filed: Oct. 16, 2018

(86) PCT No.: PCT/EP2018/078206
§ 371 (c)(1),
(2) Date: Apr. 15, 2020

(87) PCT Pub. No.: WO2019/076877
PCT Pub. Date: Apr. 25, 2019

(65) Prior Publication Data

US 2021/0189421 A1 Jun. 24, 2021

Related U.S. Application Data

(60) Provisional application No. 62/572,927, filed on Oct. 16, 2017.

(51) Int. Cl.

| | |
|---|---|
| ***C12N 15/86*** | (2006.01) |
| ***C12N 7/00*** | (2006.01) |
| ***C07K 14/005*** | (2006.01) |
| ***A61K 39/00*** | (2006.01) |
| ***A61K 35/76*** | (2015.01) |
| ***A61K 9/00*** | (2006.01) |
| ***A61K 39/12*** | (2006.01) |

(52) U.S. Cl.
CPC ............ *C12N 15/86* (2013.01); *A61K 9/0019* (2013.01); *A61K 9/0053* (2013.01); *A61K 39/12* (2013.01); *C12N 7/00* (2013.01); *A61K 2039/5256* (2013.01); *A61K 2039/54* (2013.01); *A61K 2039/572* (2013.01); *C12N 2710/10343* (2013.01); *C12N 2730/10134* (2013.01); *C12N 2760/20134* (2013.01)

(58) Field of Classification Search
CPC .......... C12N 2710/10343; C12N 15/86; C12N 2710/10322; C12N 7/00; C07K 14/005
See application file for complete search history.

(56) References Cited

FOREIGN PATENT DOCUMENTS

WO 2017017049 A1 2/2017

OTHER PUBLICATIONS

Mei et al., "Complete replication-competent adenovirus 11p vectors with E1 or E3 insertions show improved heat stability", Virology, 497, 2016:198-21.*

International Search Report and Written Opinion for corresponding International Application No. PCT/EP2018/078206, dated Dec. 19, 2018 (10 pages).

Morris et al., Simian adenoviruses as vaccine vectors, Future Virology, 2016, p. 649-659, vol. 11, issue 9.

Ya-Fang et al., "Complete replication-competent adenovirus 11p vectors with E1 or E3 insertions . . . " Virology, 2016, p. 198-210, vol. 497.

* cited by examiner

*Primary Examiner* — Barry A Chestnut

(74) *Attorney, Agent, or Firm* — Birch, Stewart, Kolasch & Birch, LLP

(57) ABSTRACT

Replication competent simian adenoviral vectors are provided for the delivery of exogenous immunogens. Vectors of the invention demonstrate superior replication and expression of exogenous immunogens. They are useful as prophylactic and therapeutic vaccines as well as in gene therapy.

18 Claims, 11 Drawing Sheets

Specification includes a Sequence Listing.

Vero Cells

SEQUENCE LISTING

```
<160> NUMBER OF SEQ ID NOS: 4

<210> SEQ ID NO 1
<211> LENGTH: 37830
<212> TYPE: DNA
<213> ORGANISM: Chimpanzee adenovirus

<400> SEQUENCE: 1

catcatcaat aatatacctt attttggatt gaagccaata tgataatgag atgggcggcg     60

cggggcggga ggcgggtccg gggcgggcc ggcgggcggg gcggtgtggc ggaagtggac    120

tttgtaagtg tggcggatgt gacttgctag tgccgggcgc ggtaaaagtg acgttttccg    180

tgcgcgacaa cgcccacggg aagtgacatt tttcccgcgg tttttaccgg atgttgtagt    240

gaatttgggc gtaaccaagt aagatttggc cattttcgcg ggaaaactga aacggggaag    300

tgaaatctga ttaatttcgc gttagtcata ccgcgtaata tttgtcgagg gccgagggac    360

tttggccgat tacgtggagg actcgcccag gtgtttttg aggtgaattt ccgcgttccg    420

ggtcaaagtc tccgttttat tattatagtc agctgacgcg gagtgtattt ataccctctg    480

atctcgtcaa gtggccactc ttgagtgcca gcgagtagag ttttctcctc tgccgctctc    540

cgctccgctc cgctcggctc tgacaccggg gaaaaaatga gacatttcac ctacgatggc    600

ggtgtgctca ccggccagct ggctgctgaa gtcctggaca ccctgatcga ggaggtattg    660

gccgataatt atcctccctc gactcctttt gagccaccta cacttcacga actctacgat    720

ctggatgtgg tggggcccag cgatccgaac gagcaggcgg tttccagttt ttttccagag    780

tccatgttgt tggccagcca ggagggggtc gaacttgaga cccctcctcc gatcgtggat    840

tcccccgatc cgccgcagct gactaggcag cccgagcgct gtgcgggacc tgagactatg    900

ccccagctgc tacctgaggt gatcgatctc acctgtaatg agtctggttt tccacccagc    960

gaggatgagg acgaagaggg tgagcagttt gtgttagatt ctgtggaaca acccgggcga   1020

ggatgcaggt cttgtcaata tcaccggaaa aacacaggag actcccagat tatgtgttct   1080

ctgtgttata tgaagatgac ctgtatgttt atttacagta agtttatcat ctgtgggcag   1140

gtgggctata gtgtgggtgg tggtctttgg ggggtttttt aatatatgtc aggggttatg   1200

ctgaagactt ttttattgtg atttttaaag gtccagtgtc tgagcccgag caagaacctg   1260

aaccggagcc tgagccttct cgccccagga gaaagcctgt aatcttaact agacccagcg   1320

caccggtagc gagaggcctc agcagcgcgg agaccaccga ctccggtgct tcctcatcac   1380

ccccggagat tcacccctg gtgcccctgt gtcccgttaa gcccgttgcc gtgagagtca   1440

gtgggcggcg gtctgctgtg gagtgcattg aggacttgct tttgattca caggaacctt   1500

tggacttgag cttgaaacgc cccaggcatt aaacctggtc acctggactg aatgagttga   1560

cgcctatgtt tgcttttgaa tgacttaatg tgtatagata ataaagagtg agataatgtt   1620
```

-continued

```
ttaattgcat ggtgtgttta acttgggcgg agtctgctgg gtatataagc ttccctgggc   1680
taaacttggt tacacttgac ctcatggagg cctgggagtg tttggagaac tttgccggag   1740
ttcgtgcctt gctggacgag agctctaaca atacctcttg gtggtggagg tatttgtggg   1800
gctctcccca gggcaagtta gtttgtagaa tcaaggagga ttacaagtgg gaatttgaag   1860
agcttttgaa atcctgtggt gagctattgg attctttgaa tctaggccac caggctctct   1920
tccaggagaa ggtcatcagg actttggatt tttccacacc ggggcgcatt gcagccgcgg   1980
ttgcttttct agcttttttg aaggatagat ggagcgaaga gacccacttg agttcgggct   2040
acgtcctgga ttttctggcc atgcaactgt ggagagcatg gatcagacac aagaacaggc   2100
tgcaactgtt gtcttccgtc cgcccgttgc tgattccggc ggaggagcaa caggccgggt   2160
cagaggaccg ggcccgtcgg gatccggagg agagggcacc gaggccgggc gagaggagcg   2220
cgctgaacct gggaaccggg ctgagcggcc atccacatcg ggagtgaatg tcgggcaggt   2280
ggtggatctt tttccagaac tgcggcggat tttgactatt agggaggatg ggcaatttgt   2340
taagggtctt aagagggaga ggggggcttc tgagcataac gaggaggcca gtaatttagc   2400
ttttagcttg atgaccagac accgtccaga gtgcatcact tttcagcaga ttaaggacaa   2460
ttgtgccaat gagttggatc tgttgggtca gaagtatagc atagagcagc tgaccactta   2520
ctggctgcag ccgggtgatg atctggagga agctattagg gtgtatgcta aggtggccct   2580
gcggcccgat tgcaagtaca agctcaaggg gctggtgaat atcaggaatt gttgctacat   2640
ttctggcaac ggggcggagg tggagataga gaccgaagac agggtggctt tcagatgcag   2700
catgatgaat atgtggccgg gggtgctggg catggacggg gtggtgatta tgaatgtgag   2760
gttcacgggg cccaacttta acggcacggt gtttttgggg aacaccaacc tggtcctgca   2820
cggggtgagc ttctatgggt ttaacaacac ctgtgtggag gcctggaccg atgtgaaggt   2880
ccgcggttgc gccttttatg gatgttggaa ggccatagtg agccgcccta agagcaggag   2940
ttccattaag aaatgcttgt ttgagaggtg caccttgggg atcctggccg agggcaactg   3000
cagggtgcgc cacaatgtgg cctccgagtg cggttgcttc atgctagtca agagcgtggc   3060
ggtaatcaag cataatatgg tgtgcggcaa cagcgaggac aaggcctcac agatgctgac   3120
ctgcacggat ggcaactgcc acttgctgaa gaccatccat gtaaccagcc acagccggaa   3180
ggcctggccc gtgttcgagc acaacttgct gacccgctgc tccttgcatc tgggcaacag   3240
gcgggggtg ttcctgccct atcaatgcaa ctttagtcac accaagatct tgctagagcc   3300
cgagagcatg tccaaggtga acttgaacgg ggtgtttgac atgaccatga agatctggaa   3360
ggtgctgagg tacgacgaga ccaggtcccg gtgcagaccc tgcgagtgcg ggggcaagca   3420
tatgaggaac cagcccgtga tgctggatgt gaccgaggag ctgaggacag accacttggt   3480
tctggcctgc accagggccg agtttggttc tagcgatgaa gacacagatt gaggtgggtg   3540
agtgggcgtg gcctggggtg gtcatgaaaa tatataagtt gggggtctta gggtctcttt   3600
atttgtgttg cagagaccgc cggagccatg agcgggagca gcagcagcag cagtagcagc   3660
agcgccttgg atggcagcat cgtgagccct tatttgacga cgcggatgcc ccactgggcc   3720
ggggtgcgtc agaatgtgat gggctccagc atcgacggcc gacccgtcct gcccgcaaat   3780
tccgccacgc tgacctatgc gaccgtcgcg gggacgccgt tggacgccac cgccgccgcc   3840
gccgccaccg cagccgcctc ggccgtgcgc agcctggcca cggactttgc attcctggga   3900
ccactggcga caggggctac ttctcgggcc gctgctgccg ccgttcgcga tgacaagctg   3960
accgccctgc tggcgcagtt ggatgcgctt actcgggaac tgggtgacct ttctcagcag   4020
```

-continued gtcatggccc tgcgccagca ggtctcctcc ctgcaagctg gcgggaatgc ttctcccaca 4080
aatgccgttt aagataaata aaaccagact ctgtttggat taaagaaaag tagcaagtgc 4140
attgctctct ttatttcata attttccgcg cgcgataggc cctagaccag cgttctcggt 4200
cgttgagggt gcggtgtatc ttctccagga cgtggtagag gtggctctgg acgttgagat 4260
acatgggcat gagcccgtcc cgggggtgga ggtagcacca ctgcagagct tcatgctccg 4320
gggtggtgtt gtagatgatc cagtcgtagc aggagcgctg ggcatggtgc ctaaaaatgt 4380
ccttcagcag caggccgatg gccaggggga ggcccttggt gtaagtgttt acaaaacggt 4440
taagttggga agggtgcatt cggggagaga tgatgtgcat cttggactgt atttttagat 4500
tggcgatgtt tccgcccaga tcccttctgg gattcatgtt gtgcaggacc accagtacag 4560
tgtatccggt gcacttgggg aatttgtcat gcagcttaga gggaaaagcg tggaagaact 4620
tggagacgcc tttgtggcct cccagatttt ccatgcattc gtccatgatg atggcaatgg 4680
gcccgcggga ggcagcttgg gcaaagatat ttctggggtc gctgacgtcg tagttgtgtt 4740
ccagggtgag gtcgtcatag gccattttta caaagcgcgg gcggagggtg cccgactggg 4800
ggatgatggt cccctctggc cctggggcgt agttgccctc gcagatctgc atttcccagg 4860
ccttaatctc ggagggggga atcatatcca cctgcggggc gatgaagaaa acggtttccg 4920
gagccgggga gattaactgg gatgagagca ggtttctaag cagctgtgat tttccacaac 4980
cggtgggccc ataaataaca cctataaccg gttgcagctg gtagtttaga gagctgcagc 5040
tgccgtcgtc ccggaggagg ggggccacct cgttgagcat gtccctgacg cgcatgttct 5100
ccccgaccag atccgccaga aggcgctcgc cgcccaggga cagcagctct tgcaaggaag 5160
caaagttttt cagcggcttg aggccgtccg ccgtgggcat gtttttcagg gtctggctca 5220
gcagctccag gcggtcccag agctcggtga cgtgctctac ggcatctcta tccagcatat 5280
ctcctcgttt cgcgggttgg ggcgactttc gctgtagggc accaagcggt ggtcgtccag 5340
cggggccaga gtcatgtcct tccatgggcg cagggtcctc gtcagggtgg tctgggtcac 5400
ggtgaagggg tgcgctccgg gctgagcgct tgccaaggtg cgcttgaggc tggttctgct 5460
ggtgctgaag cgctgccggt cttcgccctg cgcgtcggcc aggtagcatt tgaccatggt 5520
gtcatagtcc agcccctccg cggcgtgtcc cttggcgcgc agcttgccct tggaggtggc 5580
gccgcacgag gggcagagca ggctcttgag cgcgtagagc ttgggggcga ggaagaccga 5640
ttcgggggag taggcgtccg cgccgcagac cccgcacacg gtctcgcact ccaccagcca 5700
ggtgagctcg gggcgcgccg ggtcaaaaac caggtttccc ccatgctttt tgatgcgttt 5760
cttacctcgg gtctccatga ggtggtgtcc ccgctcggtg acgaagaggc tgtccgtgtc 5820
tccgtagacc gacttgaggg gtcttttctc caggggggtc cctcggtctt cctcgtagag 5880
gaactcggac cactctgaga cgaaggcccg cgtccaggcc aggacgaagg aggctatgtg 5940
ggaggggtag cggtcgttgt ccactagggg gtccaccttc tccaaggtgt gaagacacat 6000
gtcgccttcc tcggcgtcca ggaaggtgat tggcttgtag gtgtaggcca cgtgaccggg 6060
ggttcctgac ggggggggtat aaaagggggt gggggcgcgc tcgtcgtcac tctcttccgc 6120
atcgctgtct gcgagggcca gctgctgggg tgagtattcc ctctcgaagg cgggcatgac 6180
ctccgcgctg aggttgtcag tttccaaaaa cgaggaggat ttgatgttca cctgtcccga 6240
ggtgatacct ttgagggtac ccgcgtccat ctggtcagaa aacacgatct ttttattgtc 6300
cagcttggtg gcgaacgacc cgtagagggc gttggagagc agcttggcga tggagcgcag 6360
ggtctggttc ttgtccctgt cggcgcgctc cttggccgcg atgttgagct gcacgtactc 6420

-continued gcgcgcgacg cagcgccact cggggaagac ggtggtgcgc tcgtcgggca ccaggcgcac 6480
gcgccagccg cggttgtgca gggtgaccag gtccacgctg gtggcgacct cgccgcgcag 6540
gcgctcgttg gtccagcaga gacggccgcc cttgcgcgag cagaaggggg gcagggggtc 6600
gagctgggtc tcgtccgggg ggtccgcgtc cacggtgaaa accccggggc gcaggcgcgc 6660
gtcgaagtag tctatcttgc aaccttgcat gtccagcgcc tgctgccagt cgcgggcggc 6720
gagcgcgcgc tcgtaggggt tgagcggcgg gccccagggc atggggtggg tgagtgcgga 6780
ggcgtacatg ccgcagatgt catagacgta gaggggctcc cgcaggaccc cgatgtaggt 6840
ggggtagcag cggccgccgc ggatgctggc gcgcacgtag tcatacagct cgtgcgaggg 6900
ggcgaggagg tcggggccca ggttggtgcg ggcggggcgc tccgcgcgga agacgatctg 6960
cctgaagatg gcatgcgagt tggaagagat ggtggggcgc tggaagacgt tgaagctggc 7020
gtcctgcagg ccgacggcgt cgcgcacgaa ggaggcgtag gagtcgcgca gcttgtgtac 7080
cagctcggcg gtgacctgca cgtcgagcgc gcagtagtcg agggtctcgc ggatgatgtc 7140
atatttagcc tgccccttct ttttccacag ctcgcggttg aggacaaact cttcgcggtc 7200
tttccagtac tcttggatcg ggaaaccgtc cggttccgaa cggtaagagc ctagcatgta 7260
gaactggttg acggcctggt aggcgcagca gcccttctcc acggggaggg cgtaggcctg 7320
cgcggccttg cggagcgagg tgtgggtcag ggcgaaggtg tccctgacca tgactttgag 7380
gtactggtgc ttgaagtcgg agtcgtcgca gccgccccgc tcccagagcg agaagtcggt 7440
gcgcttcttg gagcgggggt tgggcagagc gaaggtgaca tcgttgaaga ggattttgcc 7500
cgcgcggggc atgaagttgc gggtgatgcg gaagggcccc ggcacttcag agcggttgtt 7560
gatgacctgg gcggcgagca cgatctcgtc gaagccgttg atgttgtggc ccacgatgta 7620
gagttccagg aagcggggcc ggccctttac ggtgggcagc ttctttagct cttcgtaggt 7680
gagctcctcg ggcgaggcga ggccgtgctc ggccagggcc cagtccgcga ggtgcgggtt 7740
gtctctgagg aaggacttcc agaggtcgcg ggccaggagg gtctgcaggc ggtctctgaa 7800
ggtcctgaac tggcggccca cggccatttt ttcgggggtg atgcagtaga aggtgagggg 7860
gtcttgctgc cagcggtccc agtcgagctg cagggcgagg tcgcgcgcgg cggtgaccag 7920
gcgctcgtcg cccccgaatt tcatgaccag catgaagggc acgagctgct ttccgaaggc 7980
ccccatccaa gtgtaggtct ctacatcgta ggtgacaaag aggcgctccg tgcgaggatg 8040
cgagccgatc gggaagaact ggatctcccg ccaccagttg gaggagtggc tgttgatgtg 8100
gtggaagtag aagtcccgtc gccgggccga acactcgtgc tggcttttgt aaaagcgagc 8160
gcagtactgg cagcgctgca cgggctgtac ctcatgcacg agatgcacct ttcgcccgcg 8220
cacgaggaag ccgaggggaa atctgagccc cccgcctggc tcgcggcatg gctggttctc 8280
ttctactttg gatgcgtgtc cgtctccgtc tggctcctcg aggggtgtta cggtggagcg 8340
gaccaccacg ccgcgcgagc cgcaggtcca gatatcggcg cgcggcggtc ggagtttgat 8400
gacgacatcg cgcagctggg agctgtccat ggtctggagc tcccgcggcg gcggcaggtc 8460
agccgggagt tcttgcaggt tcacctcgca gagtcgggcc agggcgcggg gcaggtctag 8520
gtggtacctg atctctaggg gcgtgttggt ggcggcgtcg atggcttgca ggagcccgca 8580
gccccggggg gcgacgacgg tgccccgcgg ggtggtggtg gtggtggcgg tgcagctcag 8640
aagcggtgcc gcgggcgggc ccccggaggt aggggggcct ccggtcccgc gggcaggggc 8700
ggcagcggca cgtcggcgtg gagcgcgggc aggagttggt gctgtgcccg gaggttgctg 8760
gcgaaggcga cgacgcggcg gttgatctcc tggatctggc gcctctgcgt gaagacgacg 8820

-continued

```
ggcccggtga gcttgaacct gaaagagagt tcgacagaat caatctcggt gtcattgacc   8880
gcggcctggc gcaggatctc ctgcacgtct cccgagttgt cttggtaggc gatctcggcc   8940
atgaactgct cgatctcttc ctcctggagg tctccgcgtc cggcgcgttc cacggtggcc   9000
gccaggtcgt tggagatgcg ccccatgagc tgcgagaagg cgttgagtcc gccctcgttc   9060
cagactcggc tgtagaccac gcccccctgg tcatcgcggg cgcgcatgac cacctgcgcg   9120
aggttgagct ccacgtgccg cgcgaagacg gcgtagttgc gcagacgctg gaagaggtag   9180
ttgagggtgg tggcggtgtg ctcggccacg aagaagttca tgacccagcg gcgcaacgtg   9240
gattcgttga tgtcccccaa ggcctccagc cgttccatgg cctcgtagaa gtccacggcg   9300
aagttgaaaa actgggagtt gcgcgccgac acggtcaact cctcctccag aagacggatg   9360
agctcggcga cggtgtcgcg cacctcgcgc tcgaaggcta tggggatctc ttcctccgct   9420
agcatcacca cctcctcctc ttcctcctct tctggcactt ccatgatggc ttcctcctct   9480
tcgggggtg gcggcggcgg cggtggggga gggggcgctc tgcgccggcg gcggcgcacc   9540
gggaggcggt ccacgaagcg cgcgatcatc tccccgcggc ggcggcgcat ggtctcggtg   9600
acggcgcggc cgttctcccg gggcgcagt tggaagacgc cgccggacat ctggtgctgg   9660
ggcgggtggc cgtgaggcag cgagacggcg ctgacgatgc atctcaacaa ttgctgcgta   9720
ggtacgccgc cgagggacct gagggagtcc atatccaccg gatccgaaaa cctttcgagg   9780
aaggcgtcta accagtcgca gtcgcaaggt aggctgagca ccgtggcggg cggcgggggg   9840
tggggggagt gtctggcgga ggtgctgctg atgatgtaat tgaagtaggc ggacttgaca   9900
cggcggatgg tcgacaggag caccatgtcc ttgggtccgg cctgctggat gcggaggcgg   9960
tcggctatgc cccaggcttc gttctggcat cggcgcaggt ccttgtagta gtcttgcatg  10020
agcctttcca ccggcacctc ttctccttcc tcttctgctt cttccatgtc tgcttcggcc  10080
ctggggcggc gccgcgcccc cctgcccccc atgcgcgtga ccccgaaccc cctgagcggt  10140
tggagcaggg ccaggtcggc gacgacgcgc tcggccagga tggcctgctg cacctgcgtg  10200
agggtggttt ggaagtcatc caagtccacg aagcggtggt aggcgcccgt gttgatggtg  10260
taggtgcagt tggccatgac ggaccagttg acggtctggt ggcccggttg cgacatctcg  10320
gtgtacctga gtcgcgagta ggcgcgggag tcgaagacgt agtcgttgca agtccgcacc  10380
aggtactggt agcccaccag gaagtgcggc ggcggctggc ggtagagggg ccagcgcagg  10440
gtggcggggg ctccgggggc caggtcttcc agcatgaggc ggtggtaggc gtagatgtac  10500
ctggacatcc aggtgatacc cgcggcggtg gtggaggcgc gcgggaagtc gcgcacccgg  10560
ttccagatgt tgcgcagggg cagaaagtgc tccatggtag gcgtgctctg tccagtcaga  10620
cgcgcgcagt cgttgatact ctagaccagg gaaaacgaaa gccggtcagc gggcactctt  10680
ccgtggtctg gtgaatagat cgcaagggta tcatggcgga gggcctcggt tcgagccccg  10740
ggtccgggcc ggacggtccg ccatgatcca cgcggttacc gcccgcgtgt cgaacccagg  10800
tgtgcgacgt cagacaacgg tggagtgttc cttttggcgt tttctggcc gggcgccggc  10860
gccgcgtaag agactaagcc gcgaaagcga aagcagtaag tggctcgctc cccgtagccg  10920
gagggatcct tgctaagggt tgcgttgcgg cgaaccccgg ttcgaatccc gtactcgggc  10980
cggccggacc cgcggctaag gtgttggatt ggcctccccc tcgtataaag accccgcttg  11040
cggattgact ccggacacgg ggacgagccc cttttatttt tgctttcccc agatgcatcc  11100
ggtgctgcgg cagatgcgcc ccccgcccca gcagcagcaa caacaccagc aagagcggca  11160
gcaacagcag cgggagtcat gcagggcccc ctcacccacc ctcggcgggc cggccacctc  11220
```

-continued ggcgtccgcg gccgtgtctg gcgcctgcgg cggcggcggg gggccggctg acgaccccga 11280
ggagcccccg cggcgcaggg ccagacacta cctggacctg gaggagggcg agggcctggc 11340
gcggctgggg gcgccgtctc ccgagcgcca cccgcgggtg cagctgaagc gcgactcgcg 11400
cgaggcgtac gtgcctcggc agaacctgtt cagggaccgc gcgggcgagg agcccgagga 11460
gatgcgggac aggaggttca gcgcagggcg ggagctgcgg caggggctga accgcgagcg 11520
gctgctgcgc gaggaggact ttgagcccga cgcgcggacg gggatcagcc ccgcgcgcgc 11580
gcacgtggcg gccgccgacc tggtgacggc gtacgagcag acggtgaacc aggagatcaa 11640
cttccaaaag agtttcaaca accacgtgcg cacgctggtg gcgcgcgagg aggtgaccat 11700
cgggctgatg cacctgtggg actttgtaag cgcgctggtg cagaacccca acagcaagcc 11760
tctgacggcg cagctgttcc tgatagtgca gcacagcagg gacaacgagg cgtttaggga 11820
cgcgctgctg aacatcaccg agcccgaggg tcggtggctg ctggacctga ttaacatcct 11880
gcagagcata gtggtgcagg agcgcagcct gagcctggcc gacaaggtgg cggccatcaa 11940
ctactcgatg ctgagcctgg gcaagtttta cgcgcgcaag atctaccaga cgccgtacgt 12000
gcccatagac aaggaggtga agatcgacgg tttttacatg cgcatggcgc tgaaggtgct 12060
caccctgagc gacgacctgg gcgtgtaccg caacgagcgc atccacaagg ccgtgagcgt 12120
gagccggcgg cgcgagctga gcgaccgcga gctgatgcac agcctgcagc gggcgctggc 12180
gggcgccggc agcggcgaca gggaggcgga gtcctacttc gatgcggggg cggacctgcg 12240
ctgggcgccc agccggcggg ccctggaggc cgcgggggtc cgcgaggact atgacgagga 12300
cggcgaggag gatgaggagt acgagctaga ggagggcgag tacctggact aaaccgcggg 12360
tggtgtttcc ggtagatgca agacccgaac gtggtggacc cggcgctgcg ggcggctctg 12420
cagagccagc cgtccggcct taactcctca gacgactggc gacaggtcat ggaccgcatc 12480
atgtcgctga cggcgcgtaa cccggacgcg ttccggcagc agccgcaggc caacaggctc 12540
tccgccatcc tggaggcggt ggtgcctgcg cgctcgaacc ccacgcacga gaaggtgctg 12600
gccatagtga acgcgctggc cgagaacagg gccatccgcc cggacgaggc cgggctggtg 12660
tacgacgcgc tgctgcagcg cgtggcccgc tacaacagcg gcaacgtgca gaccaacctg 12720
gaccggctgg tgggggacgt gcgcgaggcg gtggcgcagc gcgagcgcgc ggatcggcag 12780
ggcaacctgg gctccatggt ggcgctgaat gccttcctga gcacgcagcc ggccaacgtg 12840
ccgcgggggc aggaagacta caccaacttt gtgagcgcgc tgcggctgat ggtgaccgag 12900
accccccaga gcgaggtgta ccagtcgggc ccggactact tcttccagac cagcagacag 12960
ggcctgcaga cggtgaacct gagccaggct ttcaagaacc tgcgggggct gtggggcgtg 13020
aaggcgccca ccggcgaccg ggcgacggtg tccagcctgc tgacgcccaa ctcgcgcctg 13080
ctgctgctgc tgatcgcgcc gttcacggac agcggcagcg tgtcccggga cacctacctg 13140
gggcacctgc tgaccctgta ccgcgaggcc atcgggcagg cgcaggtgga cgagcacacc 13200
ttccaggaga tcaccagcgt gagccgcgcg ctggggcagg aggacacgag cagcctggag 13260
gcgactctga actacctgct gaccaaccgg cggcagaaga ttccctcgct gcacagcctg 13320
acctccgagg aggagcgcat cttgcgctac gtgcagcaga gcgtgagcct gaacctgatg 13380
cgcgacgggg tgacgcccag cgtggcgctg gacatgaccg cgcgcaacat ggaaccgggc 13440
atgtacgccg cgcaccggcc ttacatcaac cgcctgatgg actacctgca tcgcgcggcg 13500
gccgtgaacc ccgagtactt taccaacgcc atcctgaacc cgcactggct cccgccgccc 13560
gggttctaca gcgggggctt cgaggtcccg gagaccaacg atggcttcct gtgggacgac 13620

-continued

```
atggacgaca gcgtgttctc cccgcggccg caggcgctgg cggaagcgtc cctgctgcgt  13680
cccaagaagg aggaggagga ggaggcgagt cgccgccgcg gcagcagcgg cgtggcttct  13740
ctgtccgagc tgggggcggc agccgccgcg cgccccgggt ccctgggcgg cagccccttt  13800
ccgagcctgg tggggtctct gcacagcgag cgcaccaccc gccctcggct gctgggcgag  13860
gacgagtacc tgaataactc cctgctgcag ccggtgcggg agaaaaacct gcctcccgcc  13920
ttccccaaca acgggataga gagcctggtg gacaagatga gcagatggaa gacctatgcg  13980
caggagcaca gggacgcgcc tgcgctccgg ccgcccacgc ggcgccagcg ccacgaccgg  14040
cagcgggggc tggtgtggga tgacgaggac tccgcggacg atagcagcgt gctggacctg  14100
ggagggagcg gcaacccgtt cgcgcacctg cgcccccgcc tggggaggat gttttaaaaa  14160
aaaaaaaaaa aagcaagaag catgatgcaa aaattaaata aaactcacca aggccatggc  14220
gaccgagcgt tggtttcttg tgttcccttc agtatgcggc gcgcggcgat gtaccaggag  14280
ggacctcctc cctcttacga gagcgtggtg ggcgcggcgg cggcggcgcc ctcttctccc  14340
tttgcgtcgc agctgctgga gccgccgtac gtgcctccgc gctacctgcg gcctacgggg  14400
gggagaaaca gcatccgtta ctcggagctg gcgcccctgt tcgacaccac ccgggtgtac  14460
ctggtggaca acaagtcggc ggacgtggcc tccctgaact accagaacga ccacagcaat  14520
tttttgacca cggtcatcca gaacaatgac tacagcccga gcgaggccag cacccagacc  14580
atcaatctgg atgaccggtc gcactggggc ggcgacctga aaaccatcct gcacaccaac  14640
atgcccaacg tgaacgagtt catgttcacc aataagttca aggcgcgggt gatggtgtcg  14700
cgctcgcaca ccaaggaaga ccgggtggag ctgaagtacg agtgggtgga gttcgagctg  14760
ccagagggca actactccga gaccatgacc attgacctga tgaacaacgc gatcgtggag  14820
cactatctga aagtgggcag gcagaacggg gtcctggaga gcgacatcgg ggtcaagttc  14880
gacaccagga acttccgcct ggggctggac cccgtgaccg ggctggttat gcccggggtg  14940
tacaccaacg aggccttcca tcccgacatc atcctgctgc ccggctgcgg ggtggacttc  15000
acttacagcc gcctgagcaa cctcctgggc atccgcaagc ggcagccctt ccaggagggc  15060
ttcaggatca cctacgagga cctggagggg ggcaacatcc ccgcgctcct cgatgtggag  15120
gcctaccagg atagcttgaa ggaaaatgag gcgggacagg aggataccgc ccccgccgcc  15180
tccgccgccg ccgagcaggg cgaggatgct gctgacaccg cggccgcgga cggggcagag  15240
gccgaccccg ctatggtggt ggaggctccc gagcaggagg aggacatgaa tgacagtgcg  15300
gtgcgcggag acaccttcgt cacccggggg gaggaaaagc aagcggaggc cgaggccgcg  15360
gccgaggaaa agcaactggc ggcagcagcg gcggcggcgg cgttggccgc ggcggaggct  15420
gagtctgagg ggaccaagcc cgccaaggag cccgtgatta agcccctgac cgaagatagc  15480
aagaagcgca gttacaacct gctcaaggac agcaccaaca ccgcgtaccg cagctggtac  15540
ctggcctaca actacggcga cccgtcgacg ggggtgcgct cctggaccct gctgtgcacg  15600
ccggacgtga cctgcggctc ggagcaggtg tactggtcgc tgcccgacat gatgcaagac  15660
cccgtgacct tccgctccac gcggcaggtc agcaacttcc cggtggtggg cgccgagctg  15720
ctgcccgtgc actccaagag cttctacaac gaccaggccg tctactccca gctcatccgc  15780
cagttcacct ctctgaccca cgtgttcaat cgctttcctg agaaccagat tctggcgcgc  15840
ccgcccgccc ccaccatcac caccgtcagt gaaaacgttc ctgctctcac agatcacggg  15900
acgctaccgc tgcgcaacag catcggagga gtccagcgag tgaccgttac tgacgccaga  15960
cgccgcacct gcccctacgt ttacaaggcc ttgggcatag tctcgccgcg cgtcctttcc  16020
```

-continued

```
agccgcactt tttgagcaac accaccatca tgtccatcct gatctcaccc agcaataact  16080
ccggctgggg actgctgcgc gcgcccagca agatgttcgg aggggcgagg aagcgttccg  16140
agcagcaccc cgtgcgcgtg cgcgggcact tccgcgcccc ctggggagcg cacaaacgcg  16200
gccgcgcggg gcgcaccacc gtggacgacg ccatcgactc ggtggtggag caggcgcgca  16260
actacaggcc cgcggtctct accgtggacg cggccatcca gaccgtggtg cggggcgcgc  16320
ggcggtacgc caagctgaag agccgccgga agcgcgtggc ccgccgccac cgccgccgac  16380
ccggggccgc cgccaaacgc gccgccgcgg ccctgcttcg ccgggccaag cgcacgggcc  16440
gccgcgccgc catgagggcc gcgcgccgct tggccgccgg catcaccgcc gccaccatgg  16500
ccccccgtac ccgaagacgc gcggccgccg ccgccgccgc cgccatcagt gacatggcca  16560
gcaggcgccg gggcaacgtg tactgggtgc gcgactcggt gaccggcacg cgcgtgcccg  16620
tgcgcttccg cccccgcgg acttgagatg atgtgaaaaa acaacactga gtctcctgct  16680
gttgtgtgta tcccagcggc ggcggcgcgc gcagcgtcat gtccaagcgc aaaatcaaag  16740
aagagatgct ccaggtcgtc gcgccggaga tctatgggcc cccgaagaag gaagagcagg  16800
attcgaagcc ccgcaagata aagcgggtca aaaagaaaaa gaaagatgat gacgatgccg  16860
atggggaggt ggagttcctg cgcgccacgg cgcccaggcg cccggtgcag tggaagggcc  16920
ggcgcgtaaa gcgcgtcctg cgccccggca ccgcggtggt cttcacgccc ggcgagcgct  16980
ccacccggac tttcaagcgc gtctatgacg aggtgtacgg cgacgaagac ctgctggagc  17040
aggccaacga gcgcttcgga gagtttgctt acgggaagcg tcagcgggcg ctggggaagg  17100
aggacctgct ggcgctgccg ctggaccagg gcaaccccac ccccagtctg aagcccgtga  17160
ccctgcagca ggtgctgccg agcagcgcac cctccgaggc gaagcggggt ctgaagcgcg  17220
agggcggcga cctggcgccc accgtgcagc tcatggtgcc caagcggcag aggctggagg  17280
atgtgctgga gaaaatgaaa gtagaccccg gtctgcagcc ggacatcagg gtccgcccca  17340
tcaagcaggt ggcgccgggc ctcggcgtgc agaccgtgga cgtggtcatc ccccaccggca  17400
actcccccgc cgccgccacc actaccgctg cctccacgga catggagaca cagaccgatc  17460
ccgccgcagc cgcagccgca gccgccgccg cgacctcctc ggcggaggtg cagacggacc  17520
cctggctgcc gccggcgatg tcagctcccc gcgcgcgtcg cgggcgcagg aagtacggcg  17580
ccgccaacgc gctcctgccc gagtacgcct tgcatccttc catcgcgccc acccccggct  17640
accgaggcta tacctaccgc ccgcgaagag ccaagggttc cacccgccgt ccccgccgac  17700
gcgccgccgc caccacccgc cgccgccgcc gcagacgcca gcccgcactg gctccagtct  17760
ccgtgaggaa agtggcgcgc gacggacaca ccctggtgct gcccagggcg cgctaccacc  17820
ccagcatcgt ttaaaagcct gttgtggttc ttgcagatat ggccctcact tgccgcctcc  17880
gtttcccggt gccgggatac cgaggaggaa gatcgcgccg caggaggggt ctggccggcc  17940
gcggcctgag cggaggcagc cgccgcgcgc accggcggcg acgcgccacc agccgacgca  18000
tgcgcggcgg ggtgctgccc ctgttaatcc ccctgatcgc cgcggcgatc ggcgccgtgc  18060
ccgggatcgc ctccgtggcc ttgcaagcgt cccagaggca ttgacagact tgcaaacttg  18120
caaatatgga aaaaaaaacc ccaataaaaa agtctagact ctcacgctcg cttggtcctg  18180
tgactatttt gtagaatgga agacatcaac tttgcgtcgc tggccccgcg tcacggctcg  18240
cgcccgttcc tgggacactg gaacgatatc ggcaccagca acatgagcgg tggcgccttc  18300
agttggggct ctctgtggag cggcattaaa agtatcgggt ctgccgttaa aaattacggc  18360
tcccgggcct ggaacagcag cacgggccag atgttgagag acaagttgaa agagcagaac  18420
```

-continued

```
ttccagcaga aggtggtgga gggcctggcc tccggcatca acggggtggt ggacctggcc  18480
aaccaggccg tgcagaataa gatcaacagc agactggacc cccggccgcc ggtggaggag  18540
gtgccgccgg cgctggagac ggtgtccccc gatgggcgtg gcgagaagcg cccgcggccc  18600
gatagggaag agaccactct ggtcacgcag accgatgagc cgcccccgta tgaggaggcc  18660
ctgaagcaag gtctgcccac cacgcggccc atcgcgccca tggccaccgg ggtggtgggc  18720
cgccacaccc ccgccacgct ggacttgcct ccgcccgccg atgtgccgca gcagcagaag  18780
gcggcacagc cgggcccgcc cgcgaccgcc tcccgttcct ccgccggtcc tctgcgccgc  18840
gcggccagcg gcccccgcgg gggggtcgcg aggcacggca actggcagag cacgctgaac  18900
agcatcgtgg gtctgggggt gcggtccgtg aagcgccgcc gatgctactg aatagcttag  18960
ctaacgtgtt gtatgtgtgt atgcgcccta tgtcgccgcc agaggagctg ctgagtcgcc  19020
gccgttcgcg cgcccaccac caccgccact ccgcccctca agatggcgac cccatcgatg  19080
atgccgcagt ggtcgtacat gcacatctcg ggccaggacg cctcggagta cctgagcccc  19140
gggctggtgc agttcgcccg cgccaccgag agctacttca gcctgagtaa caagtttagg  19200
aaccccacgg tggcgcccac gcacgatgtg accaccgacc ggtctcagcg cctgacgctg  19260
cggttcattc ccgtggaccg cgaggacacc gcgtactcgt acaaggcgcg gttcaccctg  19320
gccgtgggcg acaaccgcgt gctggacatg gcctccacct actttgacat ccgcggggtg  19380
ctggaccggg gtcccacttt caagccctac tctggcaccg cctacaactc cctggccccc  19440
aagggcgctc ccaactcctg cgagtgggag caagaggaaa ctcaggcagt tgaagaagca  19500
gcagaagagg aagaagaaga tgctgacggt caagctgagg aagagcaagc agctaccaaa  19560
aagactcatg tatatgctca ggctcccctt tctggcgaaa aaattagtaa agatggtctg  19620
caaataggaa cggacgctac agctacagaa caaaaaccta tttatgcaga ccctacattc  19680
cagcccgaac cccaaatcgg ggagtcccag tggaatgagg cagatgctac agtcgccggc  19740
ggtagagtgc taaagaaatc tactcccatg aaaccatgct atggttccta tgcaagaccc  19800
acaaatgcta atggaggtca gggtgtacta acggcaaatg cccagggaca gctagaatct  19860
caggttgaaa tgcaattctt ttcaacttct gaaaacgccc gtaacgaggc taacaacatt  19920
cagcccaaat tggtgctgta tagtgaggat gtgcacatgg agaccccgga tacgcacctt  19980
tcttacaagc ccgcaaaaag cgatgacaat tcaaaaatca tgctgggtca gcagtccatg  20040
cccaacagac ctaattacat cggcttcaga gacaacttta tcggcctcat gtattacaat  20100
agcactggca acatgggagt gcttgcaggt caggcctctc agttgaatgc agtggtggac  20160
ttgcaagaca gaaacacaga actgtcctac cagctcttgc ttgattccat gggtgacaga  20220
accagatact tttccatgtg gaatcaggca gtggacagtt atgacccaga tgttagaatt  20280
attgaaaatc atggaactga agacgagctc cccaactatt gtttccctct gggtggcata  20340
ggggtaactg acacttacca ggctgttaaa accaacaatg gcaataacgg gggccaggtg  20400
acttggacaa aagatgaaac ttttgcagat cgcaatgaaa taggggtggg aaacaatttc  20460
gctatggaga tcaacctcag tgccaacctg tggagaaact tcctgtactc caacgtggcg  20520
ctgtacctac cagacaagct taagtacaac ccctccaatg tggacatctc tgacaacccc  20580
aacacctacg attacatgaa caagcgagtg gtggccccgg ggctggtgga ctgctacatc  20640
aacctgggcg cgcgctggtc gctggactac atggacaacg tcaacccctt caaccaccac  20700
cgcaatgcgg gcctgcgcta ccgctccatg ctcctgggca acgggcgcta cgtgcccttc  20760
cacatccagg tgccccagaa gttctttgcc atcaagaacc tcctcctcct gccgggctcc  20820
```

tacacctacg agtggaactt caggaaggat gtcaacatgg tcctccagag ctctctgggt 20880
aacgatctca gggtggacgg ggccagcatc aagttcgaga gcatctgcct ctacgccacc 20940
ttcttcccca tggcccacaa cacggcctcc acgctcgagg ccatgctcag gaacgacacc 21000
aacgaccagt ccttcaatga ctacctctcc gccgccaaca tgctctaccc catacccgcc 21060
aacgccacca acgtccccat ctccatcccc tcgcgcaact gggcggcctt ccgcggctgg 21120
gccttcaccc gcctcaagac caaggagacc ccctccctgg gctcgggatt cgacccctac 21180
tacacctact cgggctccat tccctacctg gacggcacct tctacctcaa ccacactttc 21240
aagaaggtct cggtcacctt cgactcctcg gtcagctggc cgggcaacga ccgtctgctc 21300
acccccaacg agttcgagat caagcgctcg gtcgacgggg agggctacaa cgtggcccag 21360
tgcaacatga ccaaggactg gttcctggtc cagatgctgg ccaactacaa catcggctac 21420
cagggcttct acatcccaga gagctacaag gacaggatgt actccttctt caggaacttc 21480
cagcccatga gccggcaggt ggtggaccag accaagtaca aggactacca ggaggtgggc 21540
atcatccacc agcacaacaa ctcgggcttc gtgggctacc tcgcccccac catgcgcgag 21600
ggacaggcct accccgccaa cttccccctat ccgctcatag gcaagaccgc ggtcgacagc 21660
atcacccaga aaaagttcct ctgcgaccgc accctctggc gcatcccctt ctccagcaac 21720
ttcatgtcca tgggtgcgct ctcggacctg ggccagaact tgctctacgc caactccgcc 21780
cacgccctcg acatgacctt cgaggtcgac cccatggacg agcccaccct tctctatgtt 21840
ctgttcgaag tctttgacgt ggtccgggtc caccagccgc accgcggcgt catcgagacc 21900
gtgtacctgc gtacgccctt ctcggccggc aacgccacca cctaaagaag caagccgcag 21960
tcatcgccgc ctgcatgccg tcgggttcca ccgagcaaga gctcagggcc atcgtcagag 22020
acctgggatg cgggccctat tttttgggca ccttcgacaa gcgcttccct ggctttgtct 22080
ccccacacaa gctggcctgc gccatcgtca acacggccgg ccgcgagacc gggggcgtgc 22140
actggctggc cttcgcctgg aacccgcgct ccaaaacatg cttcctcttt gacccccttcg 22200
gcttttcgga ccagcggctc aagcaaatct acgagttcga gtacgagggc ttgctgcgtc 22260
gcagcgccat cgcctcctcg cccgaccgct gcgtcaccct cgaaaagtcc acccagaccg 22320
tgcaggggcc cgactcggcc gcctgcggtc tcttctgctg catgtttctg cacgcctttg 22380
tgcactggcc tcagagtccc atggaccgca accccaccat gaacttgctg acgggggtgc 22440
ccaactccat gctccagagc ccccaggtcg agcccaccct gcgccgcaac caggagcagc 22500
tctacagctt cctggagcgc cactcgcctt acttccgccg ccacagcgca cagatcagga 22560
gggccacctc cttctgccac ttgcaagaga tgcaagaagg gtaataacga tgtacacact 22620
ttttttctca ataaatggca tctttttatt tatacaagct ctctggggta ttcatttccc 22680
accaccaccc gccgttgtcg ccatctggct ctatttagaa atcgaaaggg ttctgccggg 22740
agtcgccgtg cgccacgggc agggacacgt tgcgatactg gtagcgggtg ccccacttga 22800
actcgggcac caccaggcga ggcagctcgg ggaagttttc gctccacagg ctgcgggtca 22860
gcaccagcgc gttcatcagg tcgggcgccg agatcttgaa gtcgcagttg gggccgccgc 22920
cctgcgcgcg cgagttgcgg tacaccgggt tgcagcactg gaacaccaac agcgccgggt 22980
gcttcacgct ggccagcacg ctgcggtcgg agatcagctc ggcgtccagg tcctccgcgt 23040
tgctcagcgc gaacggggtc atcttgggca cttgccgccc caggaagggc gcgtgccccg 23100
gtttcgagtt gcagtcgcag cgcagcggga tcagcaggtg cccgtgcccg gactcggcgt 23160
tggggtacag cgcgcgcatg aaggcctgca tctggcggaa ggccatctgg gccttggcgc 23220

-continued cctccgagaa gaacatgccg caggacttgc ccgagaactg gtttgcgggg cagctggcgt 23280
cgtgcaggca gcagcgcgcg tcggtgttgg cgatctgcac cacgttgcgc ccccaccggt 23340
tcttcacgat cttggccttg gacgattgct ccttcagcgc gcgctgcccg ttctcgctgg 23400
tcacatccat ctcgatcaca tgttccttgt tcaccatgct gctgccgtgc agacacttca 23460
gctcgccctc cgtctcggtg cagcggtgct gccacagcgc gcagcccgtg ggctcgaaag 23520
acttgtaggt cacctccgcg aaggactgca ggtacccctg caaaaagcgg cccatcatgg 23580
tcacgaaggt cttgttgctg ctgaaggtca gctgcagccc gcggtgctcc tcgttcagcc 23640
aggtcttgca cacggccgcc agcgcctcca cctggtcggg cagcatcttg aagttcacct 23700
tcagctcatt ctccacgtgg tacttgtcca tcagcgtgcg cgccgcctcc atgcccttct 23760
cccaggccga caccagcggc aggctcacgg ggttcttcac catcaccgtg gccgccgcct 23820
ccgccgcgct ttcgctttcc gccccgctgt tctcttcctc ttcctcctct tcctcgccgc 23880
cgcccactcg cagcccccgc accacggggt cgtcttcctg caggcgctgc accttgcgct 23940
tgccgttgcg cccctgcttg atgcgcacgg gcgggttgct gaagcccacc atcaccagcg 24000
cggcctcttc ttgctcgtcc tcgctgtcca gaatgacctc cggggagggg gggttggtca 24060
tcctcagtac cgaggcacgc ttctttttct tcctgggggc gttcgccagc tccgcggctg 24120
cggccgctgc cgaggtcgaa ggccgagggc tgggcgtgcg cggcaccagc gcgtcctgcg 24180
agccgtcctc gtcctcctcg gactcgagac ggaggcgggc ccgcttcttc gggggcgcgc 24240
ggggcggcgg aggcggcggc ggcgacggag acggggacga gacatcgtcc agggtgggtg 24300
gacggcgggc cgcgccgcgt ccgcgctcgg gggtggtctc gcgctggtcc tcttcccgac 24360
tggccatctc ccactgctcc ttctcctata ggcagaaaga gatcatggag tctctcatgc 24420
gagtcgagaa ggaggaggac agcctaaccg cccccctctga gccctccacc accgccgcca 24480
ccaccgccaa tgccgccgcg gacgacgcgc ccaccgagac caccgccagt accaccctcc 24540
ccagcgacgc acccccgctc gagaatgaag tgctgatcga gcaggacccg ggttttgtga 24600
gcggagagga ggatgaggtg gatgagaagg agaaggagga ggtcgccgcc tcagtgccaa 24660
aagaggataa aaagcaagac caggacgacg cagataagga tgagacagca gtcgggcggg 24720
ggaacggaag ccatgatgct gatgacggct acctagacgt gggagacgac gtgctgctta 24780
agcacctgca ccgccagtgc gtcatcgtct gcgacgcgct gcaggagcgc tgcgaagtgc 24840
ccctggacgt ggcggaggtc agccgcgcct acgagcggca cctcttcgcg ccgcacgtgc 24900
cccccaagcg ccgggagaac ggcacctgcg agcccaaccc gcgtctcaac ttctacccgg 24960
tcttcgcggt acccgaggtg ctggccacct accacatctt tttccaaaac tgcaagatcc 25020
ccctctcctg ccgcgccaac cgcacccgcg ccgacaaaac cctgaccctg cggcagggcg 25080
cccacatacc tgatatcgcc tctctggagg aagtgcccaa gatcttcgag ggtctcggtc 25140
gcgacgagaa acgggcggcg aacgctctgc acggagacag cgaaaacgag agtcactcgg 25200
gggtgctggt ggagctcgag ggcgacaacg cgcgcctggc cgtactcaag cgcagcatag 25260
aggtcaccca ctttgcctac ccggcgctca acctgccccc caaggtcatg agtgtggtca 25320
tgggcgagct catcatgcgc cgcgcccagc ccctggccgc ggatgcaaac ttgcaagagt 25380
cctccgagga aggcctgccc gcggtcagcg acgagcagct ggcgcgctgg ctggagaccc 25440
gcgaccccgc gcagctggag gagcggcgca agctcatgat ggccgcggtg ctggtcaccg 25500
tggagctcga gtgtctgcag cgcttcttcg cggaccccga gatgcagcgc aagctcgagg 25560
agaccctgca ctacaccttc cgccagggct acgtgcgcca ggcctgcaag atctccaacg 25620

-continued tggagctctg caacctggtc tcctacctgg gcatcctgca cgagaaccgc ctcgggcaga 25680
acgtcctgca ctccaccctc aaaggggagg cgcgccgcga ctacatccgc gactgcgcct 25740
acctcttcct ctgctacacc tggcagacgg ccatgggggt ctggcagcag tgcctggagg 25800
agcgcaacct caaggagctg gaaaagctcc tcaagcgcac cctcagggac ctctggacgg 25860
gcttcaacga gcgctcggtg gccgccgcgc tggcggacat catctttccc gagcgcctgc 25920
tcaagaccct gcagcagggc ctgcccgact tcaccagcca gagcatgctg cagaacttca 25980
ggactttcat cctggagcgc tcgggcatcc tgccggccac ttgctgcgcg ctgcccagcg 26040
acttcgtgcc catcaagtac agggagtgcc cgccgccgct ctggggccac tgctacctct 26100
tccagctggc caactacctc gcctaccact cggacctcat ggaagacgtg agcggcgagg 26160
gcctgctcga gtgccactgc cgctgcaacc tctgcacgcc ccaccgctct ctagtctgca 26220
acccgcagct gctcagcgag agtcagatta tcggtacctt cgagctgcag ggtccctcgc 26280
ctgacgagaa gtccgcggct ccagggctga aactcactcc ggggctgtgg acttccgcct 26340
acctacgcaa atttgtacct gaggactacc acgcccacga gatcaggttc tacgaagacc 26400
aatcccgccc gcccaaggcg gagctcaccg cctgcgtcat cacccagggg cacatcctgg 26460
gccaattgca agccatcaac aaagcccgcc gagagttctt gctgaaaaag ggtcgggggg 26520
tgtacctgga cccccagtcc ggcgaggagc taaacccgct acccccgccg ccgccccagc 26580
agcgggacct tgcttcccag gatggcaccc agaaagaagc agcagccgcc gccgccgccg 26640
cagccataca tgcttctgga ggaagaggag gaggactggg acagtcaggc agaggaggtt 26700
tcggacgagg agcaggagga gatgatggaa gactgggagg aggacagcag cctagacgag 26760
gaagcttcag aggccgaaga ggtggcagac gcaacaccat cgccctcggt cgcagccccc 26820
tcgccggggc ccctgaaatc ctccgaaccc agcaccagcg ctataacctc cgctcctccg 26880
gcgccggcgc cacccgcccg cagacccaac cgtagatggg acaccacagg aaccggggtc 26940
ggtaagtcca agtgcccgcc gccgccaccg cagcagcagc agcagcagcg ccagggctac 27000
cgctcgtggc gcgggcacaa gaacgccata gtcgcctgct tgcaagactg cgggggcaac 27060
atctctttcg cccgccgctt cctgctattc caccacgggg tcgcctttcc ccgcaatgtc 27120
ctgcattact accgtcatct ctacagcccc tactgcagcg gcgacccaga ggcggcagcg 27180
gcagccacag cggcgaccac cacctaggaa gatatcctcc gcgggcaaga cagcggcagc 27240
agcggccagg agacccgcgg cagcagcggc gggagcggtg ggcgcactgc gcctctcgcc 27300
caacgaaccc ctctcgaccc gggagctcag acacaggatc ttccccactt tgtatgccat 27360
cttccaacag agcagaggcc aggagcagga gctgaaaata aaaaacagat ctctgcgctc 27420
cctcacccgc agctgtctgt atcacaaaag cgaagatcag cttcggcgca cgctggagga 27480
cgcggaggca ctcttcagca aatactgcgc gctcactctt aaagactagc tccgcgccct 27540
tctcgaattt aggcgggaga aaactacgtc atcgccggcc gccgcccagc ccgcccagcc 27600
gagatgagca aagagattcc cacgccatac atgtggagct accagccgca gatgggactc 27660
gcggcgggag cggcccagga ctactccacc cgcatgaact acatgagcgc gggaccccac 27720
atgatctcac aggtcaacgg gatccgcgcc cagcgaaacc aaatactgct ggaacaggcg 27780
gccatcaccg ccacgccccg ccataatctc aacccccgaa attggcccgc cgccctcgtg 27840
taccaggaaa ccccctccgc caccaccgta ctacttccgc gtgacgccca ggccgaagtc 27900
cagatgacta actcaggggc gcagctcgcg ggcggctttc gtcacggggc gcggccgctc 27960
cgaccaggta taagacacct gatgatcaga ggccgaggta tccagctcaa cgacgagtcg 28020

-continued

```
gtgagctctt cgctcggtct ccgtccggac ggaactttcc agctcgccgg atccggccgc  28080
tcttcgttca cgccccgcca ggcgtacctg actctgcaga cctcgtcctc ggagccccgc  28140
tccggcggca tcggaaccct ccagttcgtg gaggagttcg tgccctcggt ctacttcaac  28200
cccttctcgg gacctcccgg acgctacccc gaccagttca ttccgaactt tgacgcggtg  28260
aaggactcgg cggacggcta cgactgaatg tcaggtgtcg aggcagagca gcttcgcctg  28320
agacacctcg agcactgccg ccgccacaag tgcttcgccc gcggttctgg tgagttctgc  28380
tactttcagc tacccgagga gcataccgag gggccggcgc acggcgtccg cctgaccacc  28440
cagggcgagg ttacctgttc cctcatccgg gagtttaccc tccgtcccct gctagtggag  28500
cgggagcggg gtccctgtgt cctaactatc gcctgcaact gccctaaccc tggattacat  28560
caagatcttt gctgtcatct ctgtgctgag tttaataaac gctgagatca gaatctactg  28620
gggctcctgt cgccatcctg tgaacgccac cgtcttcacc caccccgacc aggcccaggc  28680
gaacctcacc tgcggtctgc atcggagggc caagaagtac ctcacctggt acttcaacgg  28740
cacccccttt gtggtttaca acagcttcga cggggacgga gtctccctga aagaccagct  28800
ctccggtctc agctactcca tccacaagaa caccaccctc caactcttcc ctccctacct  28860
gccgggaacc tacgagtgcg tcaccggccg ctgcacccac ctcacccgcc tgatcgtaaa  28920
ccagagcttt ccgggaacag ataactccct cttccccaga acaggaggtg agctcaggaa  28980
actccccggg gaccagggcg gagacgtacc ttcgaccctt gtggggttag gatttttttat  29040
taccgggttg ctggctcttt taatcaaagt ttccttgaga tttgttcttt ccttctacgt  29100
gtatgaacac ctcaacctcc aataactcta ccctttcttc ggaatcaggt gacttctctg  29160
aaatcgggct tggtgtgctg cttactctgt tgattttttt ccttatcata ctcagccttc  29220
tgtgcctcag gctcgccgcc tgctgcgcac acatctatat ctactgctgg ttgctcaagt  29280
gcaggggtcg ccacccaaga tgaacaggta catggtccta tcgatcctag gcctgctggc  29340
cctggcggcc tgcagcgccg ccaaaaaaga gattaccttt gaggagcccg cttgcaatgt  29400
aactttcaag cccgagggtg accaatgcac caccctcgtc aaatgcgtta ccaatcatga  29460
gaggctgcgc atcgactaca aaaacaaaac tggccagttt gcggtctata gtgtgtttac  29520
gcccggagac ccctctaact actctgtcac cgtcttccag ggcggacagt ctaagatatt  29580
caattacact ttcccttttt atgagttatg cgatgcggtc atgtacatgt caaaacagta  29640
caacctgtgg cctccctctc cccaggcgtg tgtggaaaat actgggtctt actgctgtat  29700
ggctttcgca atcactacgc tcgctctaat ctgcacggtg ctatacataa aattcaggca  29760
gaggcgaatc tttatcgatg aaaagaaaat gccttgatcg ctaacaccgg ctttctatct  29820
gcagaatgaa tgcaatcacc tccctactaa tcaccaccac cctccttgcg attgcccatg  29880
ggttgacacg aatcgaagtg ccagtggggt ccaatgtcac catggtgggc cccgccggca  29940
attccaccct catgtgggaa aaatttgtcc gcaatcaatg ggttcatttc tgctctaacc  30000
gaatcagtat caagcccaga gccatctgcg atgggcaaaa tctaactctg atcaatgtgc  30060
aaatgatgga tgctgggtac tattacgggc agcggggaga aatcattaat tactggcgac  30120
cccacaagga ctacatgctg catgtagtcg aggcacttcc cactaccacc cccactacca  30180
cctctcccac caccaccacc actactacta ctactactac tactactact actaccacta  30240
ccgctgcccg ccatacccgc aaaagcacca tgattagcac aaagcccccct cgtgctcact  30300
cccacgccgg cgggcccatc ggtgcgacct cagaaaccac cgagctttgc ttctgccaat  30360
gcactaacgc cagcgctcat gaactgttcg acctggagaa tgaggatgtc cagcagagct  30420
```

```
ccgcttgcct gacccaggag gctgtggagc ccgttgccct gaagcagatc ggtgattcaa  30480
taattgactc ttcttctttt gccactcccg aataccctcc cgattctact ttccacatca  30540
cgggtaccaa agaccctaac ctctctttct acctgatgct gctgctctgt atctctgtgg  30600
tctcttccgc gctgatgtta ctggggatgt tctgctgcct gatctgccgc agaaagagaa  30660
aagctcgctc tcagggccaa ccactgatgc ccttccccta ccccccggat tttgcagata  30720
acaagatatg agctcgctgc tgacactaac cgctttacta gcctgcgctc taacccttgt  30780
cgcttgcgac tcgagattcc acaatgtcac agctgtggca ggagaaaatg ttactttcaa  30840
ctccacggcc gatacccagt ggtcgtggag tggctcaggt agctacttaa ctatctgcaa  30900
tagctccact tcccccggca tatccccaac caagtaccaa tgcaatgcca gcctgttcac  30960
cctcatcaac gcttccaccc tggacaatgg actctatgta ggctatgtac cctttggtgg  31020
gcaaggaaag acccacgctt acaacctgga agttcgccag cccagaacca ctacccaagc  31080
ttctcccacc accaccacca ccaccaccat caccagcagc agcagcagca gcagccacag  31140
cagcagcagc agattattga ctttggtttt ggccagctca tctgccgcta cccaggccat  31200
ctacagctct gtgcccgaaa ccactcagat ccaccgccca gaaacgacca ccgccaccac  31260
cctacacacc tccagcgatc agatgccgac caacatcacc cccttggctc ttcaaatggg  31320
acttacaagc cccactccaa aaccagtgga tgcggccgag gtctccgccc tcgtcaatga  31380
ctgggcgggg ctgggaatgt ggtggttcgc cataggcatg atggcgctct gcctgcttct  31440
gctctggctc atctgctgcc tccaccgcag gcgagccaga ccccccatct atagacccat  31500
cattgtcctg aaccccgata atgatgggat ccatagattg gatggcctga aaaacctact  31560
tttttctttt acagtatgat aaattgagac atgcctcgca ttttcttgta catgttcctt  31620
ctcccacctt ttctggggtg ttctacgctg gccgctgtgt ctcacctgga ggtagactgc  31680
ctctcaccct tcactgtcta cctgctttac ggattggtca ccctcactct catctgcagc  31740
ctaatcacag taatcatcgc cttcatccag tgcattgatt acatctgtgt gcgcctcgca  31800
tacttcagac accacccgca gtaccgagac aggaacattg cccaacttct aagactgctc  31860
taatcatgca taagactgtg atctgccttc tgatcctctg catcctgccc accctcacct  31920
cctgccagta caccacaaaa tctccgcgca aaagacatgc ctcctgccgc ttcacccaac  31980
tgtggaatat acccaaatgc tacaacgaaa agagcgagct ctccgaagct tggctgtatg  32040
gggtcatctg tgtcttagtt ttctgcagca ctgtctttgc cctcataatc taccccctact  32100
ttgatttggg atggaacgcg atcgatgcca tgaattaccc caccctttccc gcacccgaga  32160
taattccact gcgacaagtt gtacccgttg tcgttaatca acgcccccca tcccctacgc  32220
ccactgaaat cagctacttt aacctaacag gcggagatga ctgacgccct agatctagaa  32280
atggacggca tcagtaccga gcagcgtctc ctagagaggc gcaggcaggc ggctgagcaa  32340
gagcgcctca atcaggagct ccgagatctc gttaacctgc accagtgcaa aagaggcatc  32400
ttttgtctgg taaagcaggc caaagtcacc tacgagaaga ccggcaacag ccaccgcctc  32460
agttacaaat tgcccaccca gcgccagaag ctggtgctca tggtgggtga gaatcccatc  32520
accgtcaccc agcactcggt agagaccgag gggtgtctgc actccccctg tcggggtcca  32580
gaagacctct gcaccctggt aaagaccctg tgcggtctca gagatttagt cccctttaac  32640
taatcaaaca ctggaatcaa taaaaagaat cacttactta aaatcagaca gcaggtctct  32700
gtccagttta ttcagcagca cctccttccc ctcctcccaa ctctggtact ccaaacgcct  32760
tctggcggca aacttcctcc acaccctgaa gggaatgtca gattcttgct cctgtccctc  32820
```

-continued

```
cgcacccact atcttcatgt tgttgcagat gaagcgcacc aaaacgtctg acgagagctt  32880
caaccccgtg taccccctatg acacggaaag cggccctccc tccgtccctt tcctcacccc  32940
tcccttcgtg tctcccgatg gattccaaga aagtcccccc ggggtcctgt ctctgaacct  33000
ggccgagccc ctggtcactt cccacggcat gctcgccctg aaaatgggaa gtggcctctc  33060
cctggacgac gctggcaacc tcacctctca agatatcacc accgctagcc ctcccctcaa  33120
aaaaaccaag accaacctca gcctagaaac ctcatccccc ctaactgtga gcacctcagg  33180
cgccctcacc gtagcagccg ccgctcccct ggcggtggcc ggcacctccc tcaccatgca  33240
atcagaggcc cccctgacag tacaggatgc aaaactcacc ctggccacca aaggcccct  33300
gaccgtgtct gaaggcaaac tggccttgca aacatcggcc ccgctgacgg ccgctgacag  33360
cagcaccctc acagtcagtg ccacaccacc ccttagcaca agcaatggca gcttgggtat  33420
tgacatgcaa gcccccattt acaccaccaa tggaaaacta ggacttaact ttggcgctcc  33480
cctgcatgtg gtagacagcc taaatgcact gactgtagtt actggccaag gtcttacgat  33540
aaacggaaca gccctacaaa ctagagtctc aggtgccctc aactatgaca catcaggaaa  33600
cctagaattg agagctgcag gggtatgcg agttgatgca aatggtcaac ttatccttga  33660
tgtagcttac ccatttgatg cacaaaacaa tctcagcctt aggcttggac agggacccct  33720
gtttgttaac tctgcccaca acttggatgt taactacaac agaggcctct acctgttcac  33780
atctggaaat accaaaaagc tagaagttaa tatcaaaaca gccaagggtc tcatttatga  33840
tgacactgct atagcaatca atgcgggtga tgggctacag tttgactcag gctcagatac  33900
aaatccatta aaaactaaac ttggattagg actggattat gactccagca gagccataat  33960
tgctaaactg ggaactggcc taagctttga caacacaggt gccatcacag taggcaacaa  34020
aaatgatgac aagcttacct tgtggaccac accagaccca tcccctaact gtagaatcta  34080
ttcagagaaa gatgctaaat tcacacttgt tttgactaaa tgcggcagtc aggtgttggc  34140
cagcgtttct gttttatctg taaaaggtag ccttgcgccc atcagtggca cagtaactag  34200
tgctcagatt gtcctcagat ttgatgaaaa tggagttcta ctaagcaatt cttcccttga  34260
ccctcaatac tggaactaca gaaaaggtga ccttacagag ggcactgcat ataccaacgc  34320
agtgggattt atgcccaacc tcacagcata cccaaaaaca cagagccaaa ctgctaaaag  34380
caacattgta agtcaggttt acttgaatgg ggacaaatcc aaacccatga ccctcaccat  34440
taccctcaat ggaactaatg aaacaggaga tgccacagta agcacttact ccatgtcatt  34500
ctcatggaac tggaatggaa gtaattacat taatgaaacg ttccaaacca actccttcac  34560
cttctcctac atcgcccaag aataaaaagc atgacgctgt tgatttgatt caatgtgttt  34620
ctgttttatt ttcaagcaca acaaaatcat tcaagtcatt cttccatctt agcttaatag  34680
acacagtagc ttaatagacc cagtagtgca aagccccatt ctagcttata gatcagacag  34740
tgataattaa ccaccaccac caccatacct tttgattcag gaaatcatga tcatcacagg  34800
atcctagtct tcaggccgcc ccctccctcc caagacacag aatacacagt cctctccccc  34860
cgactggctt taaataacac catctggttg gtcacagaca tgttcttagg ggttatattc  34920
cacacggtct cctgccgcgc caggcgctcg tcggtgatgt tgataaactc tcccggcagc  34980
tcgctcaagt tcacgtcgct gtccagcggc tgaacctccg gctgacgcga taactgtgcg  35040
accggctgct ggacgaacgg aggccgcgcc tacaaggggg tagagtcata atcctcggtc  35100
aggatagggc ggtgatgcag cagcagcgag cgaaacatct gctgccgccg ccgctccgtc  35160
cggcaggaaa acaacacgcc ggtggtctcc tccgcgataa tccgcaccgc ccgcagcatc  35220
```

-continued

```
agcttcctcg ttctccgcgc gcagcacctc acccttatct cgctcaaatc ggcgcagtag  35280
gtacagcaca gcaccacgat gttattcatg atcccacagt gcagggcgct gtatccaaag  35340
ctcatgccgg gaaccaccgc ccccacgtgg ccatcgtacc acaagcgcac gtaaatcaag  35400
tgtcgacccc tcatgaacgc gctggacaca aacattactt ccttgggcat gttgtaattc  35460
accacctccc ggtaccagat aaacctctgg ttgaacaggg caccttccac caccatcctg  35520
aaccaagagg ccagaacctg cccaccggct atgcactgca gggaacccgg gttggaacaa  35580
tgacaatgca gactccaagg ctcgtaaccg tggatcatcc ggctgctgaa ggcatcgatg  35640
ttggcacaac acagacacac gtgcatgcac tttctcatga ttagcagctc ttccctcgtc  35700
aggatcatat cccaaggaat aacccattct tgaatcaacg taaaacccac acagcaggga  35760
aggcctcgca cataactcac gttgtgcatg gtcagcgtgt tgcattccgg aaacagcgga  35820
tgatcctcca gtatcgaggc gcgggtctcc ttctcacagg gaggtaaagg gtccctgctg  35880
tacggactgc gccgggacga ccgagatcgt gttgagcgta gtgtcatgga aaagggaacg  35940
ccggacgtgg tcatacttct tgaagcagaa ccaggttcgc gcgtggcagg cctccttgcg  36000
tctgcggtct cgccgtctag ctcgctccgt gtgatagttg tagtacagcc actcccgcag  36060
agcgtcgagg cgcaccctgg cttccggatc tatgtagact ccgtcttgca ccgcggccct  36120
gataatatcc accaccgtag aataagcaac acccagccaa gcaatacact cgctctgcga  36180
gcggcagaca ggaggagcgg gcagagatgg gagaaccatg ataaaaaact ttttttaaag  36240
aatattttcc aattcttcga aagtaagatc tatcaagtgg cagcgctccc ctccactggc  36300
gcggtcaaac tctacggcca aagcacagac aacggcattt ctaagatgtt ccttaatggc  36360
gtccaaaaga cacaccgctc tcaagttgca gtaaactatg aatgaaaacc catccggctg  36420
attttccaat atagacgcgc cggcagcgtc caccaaaccc agataatttt cttctctcca  36480
gcggtttacg atctgtctaa gcaaatccct tatatcaagt ccgaccatgc caaaaaatctg  36540
ctcaagagcg ccctccacct tcatgtacaa gcagcgcatc atgattgcaa aaattcaggt  36600
tcttcagaga cctgtataag attcaaaatg ggaacattaa caaaaattcc tctgtcgcgc  36660
agatcccttc gcagggcaag ctgaacataa tcagacaggt ccgaacggac cagtgaggcc  36720
aaatccccac caggaaccag atccagagac cctatactga ttatgacgcg catactcggg  36780
gctatgctga ccagcgtagc gccgatgtag gcgtgctgca tgggcggcga gataaaatgc  36840
aaagtgctgg ttaaaaaatc aggcaaagcc tcgcgcaaaa aagctaacac atcataatca  36900
tgctcatgca ggtagttgca ggtaagctca ggaaccaaaa cggaataaca cacgattttc  36960
ctctcaaaca tgacttcgcg gatactgcgt aaaacaaaaa attataaata aaaaattaat  37020
taaataactt aaacattgga agcctgtctc acaacaggaa aaaccacttt aatcaacata  37080
agacgggcca cgggcatgcc ggcatagccg taaaaaaatt ggtccccgtg attaacaagt  37140
accacagaca gctccccggt catgtcgggg gtcatcatgt gagactctgt atacacgtct  37200
ggattgtgaa catcagacaa acaaagaaat cgagccacgt agcccggagg tataatcacc  37260
cgcaggcgga ggtacagcaa aacgaccccc ataggaggaa tcacaaaatt agtaggagaa  37320
aaaaatacat aaacaccaga aaaccctgt tgctgaggca aaatagcgcc ctcccgatcc  37380
aaaacaacat aaagcgcttc cacaggagca gccataacaa agacccgagt cttaccagta  37440
aaagaaaaaa gatctctcaa cgcagcacca gcaccaacac ttcgcagtgt aaaaggccaa  37500
gtgccgagag agtatatata ggaataaaaa gtgacgtaaa cgggcaaagt ccaaaaaacg  37560
cccagaaaaa ccgcacgcga acctacgccc cgaaacgaaa gccaaaaaac actagacact  37620
```

-continued cccttccggc gtcaacttcc gctttcccac gctacgtcac ttcccccggt caaacaaact 37680
acatatcccg aacttccaag tcgccacgcc caaaacaccg cctacacctc cccgcccgcc 37740
ggcccgcccc cggacccgcc tcccgccccg cgccgcccat ctcattatca tattggcttc 37800
aatccaaaat aaggtatatt attgatgatg 37830

<210> SEQ ID NO 2
<211> LENGTH: 36571
<212> TYPE: DNA
<213> ORGANISM: Chimpanzee adenovirus

<400> SEQUENCE: 2
catcatcaat aatatacctc aaacttttgg tgcgcgttaa tatgcaaatg agctgtttga 60
atttggggat gcggggcgct gattggctgc gggagcggcg accgttaggg gcggggcggg 120
tgacgttttg atgacgtggc cgtgaggcgg agccggtttg caagttctcg tgggaaaagt 180
gacgtcaaac gaggtgtggt ttgaacacgg aaatactcaa ttttcccgcg ctctctgaca 240
ggaaatgagg tgtttctggg cggatgcaag tgaaaacggg ccattttcgc gcgaaaactg 300
aatgaggaag tgaaaatctg agtaatttcg cgtttatggc agggaggagt atttgccgag 360
ggccgagtag actttgaccg attacgtggg ggtttcgatt accgtatttt tcacctaaat 420
ttccgcgtac ggtgtcaaag tccggtgttt ttacgtaggc gtcagctgat cgccagggta 480
tttaaacctg cgctcactag tcaagaggcc actcttgagt gccagcgagt agagttttct 540
cctccgcgcc gcgagtcaga tctacacttt gaaagatgag gcacttgaga gacctgcccg 600
gtaatgtttt cctggctact gggaacgaga ttctggaatt ggtggtggac gccatgatgg 660
gtgacgaccc tcccgagccc cctaccccat ttgaggcgcc ttcgctgtac gatttgtatg 720
atctggaggt ggatgtgccc gagaacgacc ccaacgagga ggcggtgaat gatttgttta 780
gcgatgccgc gctgctggct gccgagcagg ctaatacgga ctttggctca gacagcgatt 840
cttctctcca taccccgaga cccggcagag gtgagaaaaa gatccccgag cttaaagggg 900
aagagctcga cctgcgctgc tatgaggaat gcttgcctcc gagcgatgat gaggaggacg 960
aggaggcgat tcgagctgca gcgaaccagg gagtgaaagc tgcgggcgaa agctttagcc 1020
tggactgtcc tactctgccc ggacacggct gtaagtcttg tgaatttcat cgcatgaata 1080
ctggagataa gaatgtgatg tgtgccctgt gctatatgag agcttacaac cattgtgttt 1140
acagtaagtg tgattaactt tagttgggaa ggcagagggt gactgggtgc tgactggttt 1200
atttatgtat atgtttttta tgtgtaggtc ccgtctctga cgcagatgag acccccactt 1260
cagagtgcat ttcatcaccc ccagaaattg gcgaggaacc gcccgaagat attattcata 1320
gaccagttgc agtgagagtc accgggcgga gagcagctgt ggagagtttg gatgacttgc 1380
tacagggtgg ggatgaacct ttggacttgt gtacccggaa acgccccagg cactaagtgc 1440
cacacatgtg tgtttactta aggtgatgtc agtatttata gggtgtggag tgcaataaaa 1500
tccgtgttga ctttaagtgc gtggtttatg actcaggggt ggggactgtg ggtatataag 1560
caggtgcaga cctgtgtggt cagttcagag caggactcat ggagatctgg acggtcttgg 1620
aagactttca ccagactaga cagctgctag agaactcatc ggagggagtc tcttacctgt 1680
ggagattctg cttcggtggg cctctagcta agctagtcta tagggccaag caggattata 1740
aggatcaatt tgaggatatt ttgagagagt gtcctggtat ttttgactct ctcaacttgg 1800
gccatcagtc tcactttaac cagagtattc tgagagccct tgacttttcc actcctggca 1860
gaactaccgc cgcggtagcc ttttttgcct ttatccttga caaatggagt caagaaaccc 1920

-continued

```
atttcagcag ggattaccgt ctggactgct tagcagtagc tttgtggaga acatggaggt   1980
gccagcgcct gaatgcaatc tccggctact tgccagtaca gccggtagac acgctgagga   2040
tcctgagtct ccagtcaccc caggaacacc aacgccgcca gcagccgcag caggagcagc   2100
agcaagagga ggaccgagaa gagaacccga gagccggtct ggaccctccg gtggcggagg   2160
aggaggagta gctgacttgt ttcccgagct gcgccgggtg ctgactaggt cttccagtgg   2220
acgggagagg gggattaagc gggagaggca tgaggagact agtcacagaa ctgaactgac   2280
tgtcagtctg atgagccgca ggcgcccaga atcggtgtgg tggcatgagg tgcagtcgca   2340
ggggatagat gaggtctcgg tgatgcatga gaaatattcc ctagaacaag tcaagacttg   2400
ttggttggag cctgaggatg attgggaggt agccatcagg aattatgcca agctagctct   2460
gaagccagac aagaagtaca agattaccaa actgattaat atcagaaatt cctgctacat   2520
ttcagggaat ggggccgagg tggagatcag tacccaggag agggtggcct tcagatgctg   2580
catgatgaat atgtacccgg gggtggtggg catggaggga gtcaccttta tgaacgcgag   2640
gttcaggggc gatgggtata atggggtggt ctttatggcc aacaccaagc tgacagtgca   2700
cggatgctcc ttctttggct tcaataacat gtgcatcgag gcctggggca gtgtttcagt   2760
gaggggatgc agtttttcag ccaactggat gggggtcgtg ggcagaacca agagcaaggt   2820
gtcagtgaag aaatgcctgt tcgagaggtg ccacctgggg gtgatgagcg agggcgaagc   2880
caaagtcaaa cactgcgcct ctactgagac gggctgcttt gtgctgatca agggcaatgc   2940
ccaagtcaag cataacatga tctgtggggc ctcggatgag cgcggctacc agatgctgac   3000
ctgcgccggt gggaacagcc atatgctggc caccgtgcat gtgacctcgc acccccgcaa   3060
gacatggccc gagttcgagc acaacgtcat gacccgctgc aatgtgcacc tgggctcccg   3120
ccgaggcatg ttcatgccct accagtgcaa catgcaattt gtgaaggtgc tgctggagcc   3180
cgatgccatg tccagagtga gcctgacggg ggtgtttgac atgaatgtgg agatgtggaa   3240
aattctgaga tatgatgaat ccaagaccag gtgccgggcc tgcgaatgcg gaggcaagca   3300
cgccaggctt cagcccgtgt gtgtggaggt gacggaggac ctgcgacccg atcatttggt   3360
gttgtcctgc aacgggacgg agttcggctc cagcggggaa gaatctgact agagtgagta   3420
gtgtttgggg gaggtggagg gcctggatga ggggcagaat gactaaaatc tgtgtttttc   3480
tgcgcagcag catgagcgga agcgcctcct ttgagggagg ggtattcagc ccttatctga   3540
cggggcgtct cccctcctgg gcgggagtgc gtcagaatgt gatgggatcc acggtggacg   3600
gccggcccgt gcagcccgcg aactcttcaa ccctgaccta cgcgaccctg agctcctcgt   3660
ccgtggacgc agctgccgcc gcagctgctg cttccgccgc cagcgccgtg cgcggaatgg   3720
ccctgggcgc cggctactac agctctctgg tggccaactc gagttccacc aataatcccg   3780
ccagcctgaa cgaggagaag ctgctgctgc tgatggccca gctcgaggcc ctgacccagc   3840
gcctgggcga gctgacccag caggttgctc agctgcaggc ggagacgcgg gccgcggttg   3900
ccacggtgaa aaccaaataa aaaatgaatc aataaataaa cggagacggt tgttgatttt   3960
aacacagagt cttgaatctt tatttgattt ttcgcgcgcg gtaggccctg gaccaccggt   4020
ctcgatcatt gagcacccgg tggatctttt ccaggacccg gtagaggtgg gcttggatgt   4080
tgaggtacat gggcatgagc ccgtcccggg ggtggaggta gctccattgc agggcctcgt   4140
gctcgggggt ggtgttgtaa atcacccagt catagcaggg gcgcagggcg tggtgctgca   4200
cgatgtcctt gaggaggaga ctgatggcca cgggcagccc cttggtgtag gtgttgacga   4260
acctgttgag ctgggaggga tgcatgcggg gggagatgag atgcatcttg gcctggatct   4320
```

-continued

```
tgagattggc gatgttcccg cccagatccc gccgggggtt catgttgtgc aggaccacca   4380
gcacggtgta tccggtgcac ttggggaatt tgtcatgcaa cttggaaggg aaggcgtgaa   4440
agaatttgga gacgcccttg tggccgccca ggttttccat gcactcatcc atgatgatgg   4500
cgatgggccc gtgggcggcg gcctgggcaa agacgtttcg ggggtcggac acatcgtagt   4560
tgtggtcctg ggtgagctcg tcataggcca ttttaatgaa tttggggcgg agggtgcccg   4620
actgggggac gaaggtgccc tcgatcccgg gggcgtagtt gccctcgcag atctgcatct   4680
cccaggcctt gagctcggag ggggggatca tgtccacctg cggggcgatg aaaaaaacgg   4740
tttccggggc gggggagatg agctgcgccg aaagcaggtt ccggagcagc tgggacttgc   4800
cgcagccggt ggggccgtag atgaccccga tgaccggctg caggtggtag ttgagggaga   4860
gacagctgcc gtcctcgcgg aggagggggg ccacctcgtt catcatctcg cgcacatgca   4920
tgttctcgcg cacgagttcc gccaggaggc gctcgccccc cagcgagagg agctcttgca   4980
gcgaggcgaa gtttttcagc ggcttgagcc cgtcggccat gggcattttg gagagggtct   5040
gttgcaagag ttccagacgg tcccagagct cggtgatgtg ctctagggca tctcgatcca   5100
gcagacctcc tcgtttcgcg ggttggggcg actgcgggag tagggcacca ggcgatgggc   5160
gtccagcgag gccagggtcc ggtccttcca gggtcgcagg gtccgcgtca gcgtggtctc   5220
cgtcacggtg aaggggtgcg cgccgggctg ggcgcttgcg agggtgcgct tcaggctcat   5280
ccggctggtc gagaaccgct cccggtcggc gccctgtgcg tcggccaggt agcaattgag   5340
catgagttcg tagttgagcg cctcggccgc gtggcccttg gcgcggagct tacctttgga   5400
agtgtgtccg cagacgggac agaggaggga cttgagggcg tagagcttgg gggcgaggaa   5460
gacggactcg gggcgtagg cgtccgcgcc gcagctggcg cagacggtct cgcactccac   5520
gagccaggtg aggtcggggc ggtcggggtc aaaaacgagg tttcctccgt gctttttgat   5580
gcgtttctta cctctggtct ccatgagctc gtgtccccgc tgggtgacaa agaggctgtc   5640
cgtgtccccg tagaccgact ttatgggccg gtcctcgagc ggggtgccgc ggtcctcgtc   5700
gtagaggaac cccgcccact ccgagacgaa ggcccgggtc caggccagca cgaaggaggc   5760
cacgtgggag gggtagcggt cgttgtccac cagcgggtcc accttctcca gggtatgcaa   5820
gcacatgtcc ccctcgtcca catccaggaa ggtgattggc ttgtaagtgt aggccacgtg   5880
accgggggtc ccggccgggg gggtataaaa gggggcgggc cctgctcgt cctcactgtc   5940
ttccggatcg ctgtccagga gcgccagctg ttggggtagg tattccctct cgaaggcggg   6000
catgacctcg gcactcaggt tgtcagtttc tagaaacgag gaggatttga tattgacggt   6060
gccgttggag acgcctttca tgagcccctc gtccatctgg tcagaaaaga cgatcttttt   6120
gttgtcgagc ttggtggcga aggagccgta gagggcgttg gagagcagct tggcgatgga   6180
gcgcatggtc tggttctttt ccttgtcggc gcgctccttg gcggcgatgt tgagctgcac   6240
gtactcgcgc gccacgcact tccattcggg gaagacggtg gtgagctcgt cgggcacgat   6300
tctgacccgc cagccgcggt tgtgcagggt gatgaggtcc acgctggtgg ccacctcgcc   6360
gcgcaggggc tcgttggtcc agcagaggcg cccgcccttg cgcgagcaga aggggggcag   6420
cgggtccagc atgagctcgt cgggggggtc ggcgtccacg gtgaagatgc cgggcaggag   6480
ctcggggtcg aagtagctga tgcaggtgcc cagatcgtcc agcgccgctt gccagtcgcg   6540
cacggccagc gcgcgctcgt aggggctgag gggcgtgccc cagggcatgg ggtgcgtgag   6600
cgcggaggcg tacatgccgc agatgtcgta gacgtagagg ggctcctcga ggacgccgat   6660
gtaggtgggg tagcagcgcc ccccgcggat gctggcgcgc acgtagtcgt acagctcgtg   6720
```

-continued

```
cgagggcgcg aggagccccg tgccgaggtt ggagcgttgc ggcttttcgg cgcggtagac   6780
gatctggcgg aagatggcgt gggagttgga ggagatggtg ggcctctgga agatgttgaa   6840
gtgggcgtgg ggcaggccga ccgagtccct gatgaagtgg gcgtaggagt cctgcagctt   6900
ggcgacgagc tcggcggtga cgaggacgtc cagggcgcag tagtcgaggg tctcttggat   6960
gatgtcgtac ttgagctggc ccttctgctt ccacagctcg cggttgagaa ggaactcttc   7020
gcggtccttc cagtactctt cgagggggaa cccgtcctga tcggcacggt aagagcccac   7080
catgtagaac tggttgacgg ccttgtaggc gcagcagccc ttctccacgg ggagggcgta   7140
agcttgcgcg gccttgcgca gggaggtgtg ggtgagggcg aaggtgtcgc gcaccatgac   7200
tttgaggaac tggtgcttga agtcgaggtc gtcgcagccg ccctgctccc agagttggaa   7260
gtccgtgcgc ttcttgtagg cggggttggg caaagcgaaa gtaacatcgt tgaagaggat   7320
cttgcccgcg cggggcatga agttgcgagt gatgcggaaa ggctggggca cctcggcccg   7380
gttgttgatg acctgggcgg cgaggacgat ctcgtcgaag ccgttgatgt tgtgcccgac   7440
gatgtagagt tccacgaatc gcgggcagcc cttgacgtgg ggcagcttct tgagctcgtc   7500
gtaggtgagc tcggcggggt cgctgagccc gtgctgctcg agggcccagt cggcgacgtg   7560
ggggttggcg ctgaggaagg aagtccagag atccacggcc agggcggtct gcaagcggtc   7620
ccggtactga cggaactgct ggcccacggc catttttcg ggggtgacgc agtagaaggt   7680
gcgggggtcg ccgtgccagc ggtcccactt gagttggagg gcgaggtcgt gggcgagctc   7740
gacgagcggc gggtccccgg agagtttcat gaccagcatg aaggggacga gctgcttgcc   7800
gaaggacccc atccaggtgt aggtttccac atcgtaggtg aggaagagcc tttcggtgcg   7860
aggatgcgag ccgatgggga agaactggat ctcctgccac cagttggagg aatggctgtt   7920
gatgtgatgg aagtagaaat gccgacggcg cgccgagcac tcgtgcttgt gtttatacaa   7980
gcgtccgcag tgctcgcaac gctgcacggg atgcacgtgc tgcacgagct gtacctgggt   8040
tcctttgacg aggaatttca gtgggcagtg gagcgctggc ggctgcatct ggtgctgtac   8100
tacgtcctgg ccatcggcgt ggccatcgtc tgcctcgatg gtggtcatgc tgacgagccc   8160
gcgcgggagg caggtccaga cctcggctcg gacgggtcgg agagcgagga cgagggcgcg   8220
caggccggag ctgtccaggg tcctgagacg ctgcggagtc aggtcagtgg gcagcggcgg   8280
cgcgcggttg acttgcagga gcttttccag ggcgcgcggg aggtccagat ggtacttgat   8340
ctccacggcg ccgttggtgg cgacgtccac ggcttgcagg gtcccgtgcc cctggggcgc   8400
caccaccgtg ccccgtttct tcttgggcgg cggcggctcc atgcttagaa gcggcggcga   8460
ggacgcgcgc cgggcggcag gggcggctcg gggcccggag gcaggggcgg caggggcacg   8520
tcggcgccgc gcgcgggcag gttctggtac tgcgcccgga gaagactggc gtgagcgacg   8580
acgcgacggt tgacgtcctg gatctgacgc ctctgggtga aggccacggg acccgtgagt   8640
ttgaacctga aagagagttc gacagaatca atttcggtat cgttgacggc ggcctgccgc   8700
aggatctctt gcacgtcgcc cgagttgtcc tggtaggcga tctcggtcat gaactgctcg   8760
atctcctcct cctgaaggtc tccgcggccg gcgcgctcga cggtggccgc gaggtcgttg   8820
gagatgcggc ccatgagctg cgagaaggcg ttcatgccgg cctcgttcca gacgcggctg   8880
tagaccacgg ctccgttggg gtcgcgcgcg cgcatgacca cctgggcgag gttaagctcg   8940
acgtggcgcg tgaagaccgc gtagttgcag aggcgctggt agaggtagtt gagcgtggtg   9000
gcgatgtgct cggtgacgaa gaagtacatg atccagcggc ggagcggcat ctcgctgacg   9060
tcgcccaggg cttccaagcg ctccatggtc tcgtagaagt ccacggcgaa gttgaaaaac   9120
```

-continued

```
tgggagttgc gcgccgagac ggtcaactcc tcctccagaa gacggatgag ctcggcgatg   9180
gtggcgcgca cctcgcgctc gaaggccccg gggggctcct cttcttccat ctcctcctcc   9240
tcttcctcct ccactaacat ctcttctact tcctcctcag gaggcggcgg cgggggaggg   9300
gccctgcgtc gccggcggcg cacgggcaga cggtcgatga agcgctcgat ggtctccccg   9360
cgccggcgac gcatggtctc ggtgacggcg cgcccgtcct cgcggggccg cagcgtgaag   9420
acgccgccgc gcatctccag gtggccgccg gggggtctc cgttgggcag ggagagggcg    9480
ctgacgatgc atcttatcaa ttggcccgta gggactccgc gcaaggacct gagcgtctcg   9540
agatccacgg gatccgaaaa ccgctgaacg aaggcttcga gccagtcgca gtcgcaaggt   9600
aggctgagcc cggtttcttg ttcttcgggt atttggtcgg gaggcgggcg ggcgatgctg   9660
ctggtgatga agttgaagta ggcggtcctg agacggcgga tggtggcgag gagcaccagg   9720
tccttgggcc cggcttgctg gatgcgcaga cggtcggcca tgccccaggc gtggtcctga   9780
cacctggcga ggtccttgta gtagtcctgc atgagccgct ctacgggcac gtcctcctcg   9840
cccgcgcggc cgtgcatgcg cgtgagcccg aacccgcgct gcggctggac gagcgccagg   9900
tcggcgacga cgcgctcggc gaggatggcc tgctggatct gggtgagggt ggtctggaag   9960
tcgtcgaagt cgacgaagcg gtggtaggct ccggtgttga tggtgtagga gcagttggcc  10020
atgacggacc agttgacggt ctggtggccg gggcgcacga gctcgtggta cttgaggcgc  10080
gagtaggcgc gcgtgtcgaa gatgtagtcg ttgcaggtgc gcacgaggta ctggtatccg  10140
acgaggaagt gcggcggcgg ctggcggtag agcggccatc gctcggtggc gggggcgccg  10200
ggcgcgaggt cctcgagcat gaggcggtgg tagccgtaga tgtacctgga catccaggtg  10260
atgccggcgg cggtggtgga ggcgcgcggg aactcgcgga cgcggttcca gatgttgcgc  10320
agcggcagga agtagttcat ggtggccgcg gtctggcccg tgaggcgcgc gcagtcgtgg  10380
atgctctaga catacgggca aaaacgaaag cggtcagcgg ctcgactccg tggcctggag  10440
gctaagcgaa cgggttgggc tgcgcgtgta ccccggttcg aatctcgaat caggctggag  10500
ccgcagctaa cgtggtactg gcactcccgt ctcgacccaa gcctgctaac gaaacctcca  10560
ggatacggag gcgggtcgtt ttttggcctt ggtcgctggt catgaaaaac tagtaagcgc  10620
ggaaagcggc cgcccgcgat ggctcgctgc cgtagtctgg agaaagaatc gccagggttg  10680
cgttgcggtg tgccccggtt cgagcctcag cgctcggtgc cggccggatt ccgcggctaa  10740
cgtgggcgtg gctgccccgt cgtttccaag accccttagc cagccgactt ctccagttac  10800
ggagcgagcc cctctttttc ttgtgttttt gccagatgca tcccgtactg cggcagatgc  10860
gcccccaccc tccaccacaa ccgcccctac cgcagcagca gcaacagccg gcgcttctgc  10920
ccccgcccca gcagcagcag ccagccacta ccgcggcggc cgccgtgagc ggagccggcg  10980
ttcagtatga cctggccttg gaagagggcg aggggctggc gcggctgggg gcgtcgtcgc  11040
cggagcggca cccgcgcgtg cagatgaaaa gggacgctcg cgaggcctac gtgcccaagc  11100
agaacctgtt cagagacagg agcggcgagg agcccgagga gatgcgcgcc tcccgcttcc  11160
acgcggggcg ggagctgcgg cgcggcctgg accgaaagcg ggtgctgagg gacgaggatt  11220
tcgaggcgga cgagctgacg gggatcagcc ccgcgcgcgc gcacgtggcc gcggccaacc  11280
tggtcacggc gtacgagcag accgtgaagg aggagagcaa ctttcaaaaa tccttcaaca  11340
accacgtgcg cacgctgatc gcgcgcgagg aggtgaccct gggcctgatg cacctgtggg  11400
acctgctgga ggccatcgtg cagaacccca cgagcaagcc gctgacggcg cagctgtttc  11460
tggtggtgca gcacagtcgg gacaacgaga cgttcaggga ggcgctgctg aatatcaccg  11520
```

agcccgaggg ccgctggctc ctggacctgg tgaacattct gcagagcatc gtggtgcagg 11580
agcgcgggct gccgctgtcc gagaagctgg cggccatcaa cttctcggtg ctgagcctgg 11640
gcaagtacta cgctaggaag atctacaaga ccccgtacgt gcccatagac aaggaggtga 11700
agatcgacgg gttttacatg cgcatgaccc tgaaagtgct gaccctgagc gacgatctgg 11760
gggtgtaccg caacgacagg atgcaccgcg cggtgagcgc cagccgccgg cgcgagctga 11820
gcgaccagga gctgatgcac agcctgcagc gggccctgac cggggccggg accgaggggg 11880
agagctactt tgacatgggc gcggacctgc gctggcagcc cagccgccgg gccttggaag 11940
ctgccggcgg cgtgccctac gtggaggagg tggacgatga ggaggaggag ggcgagtacc 12000
tggaagactg atggcgcgac cgtatttttg ctagatgcag caacagccac cgccgcctcc 12060
tgatcccgcg atgcgggcgg cgctgcagag ccagccgtcc ggcattaact cctcggacga 12120
ttggacccag gccatgcaac gcatcatggc gctgacgacc cgcaatcccg aagcctttag 12180
acagcagcct caggccaacc ggctctcggc catcctggag gccgtggtgc cctcgcgctc 12240
gaaccccacg cacgagaagg tgctggccat cgtgaacgcg ctggtggaga acaaggccat 12300
ccgcggcgac gaggccgggc tggtgtacaa cgcgctgctg gagcgcgtgg cccgctacaa 12360
cagcaccaac gtgcagacga acctggaccg catggtgacc gacgtgcgcg aggcggtgtc 12420
gcagcgcgag cggttccacc gcgagtcgaa cctgggctcc atggtggcgc tgaacgcctt 12480
cctgagcacg cagcccgcca acgtgccccg gggccaggag gactacacca acttcatcag 12540
cgcgctgcgg ctgatggtgg ccgaggtgcc ccagagcgag gtgtaccagt cggggccgga 12600
ctacttcttc cagaccagtc gccagggctt gcagaccgtg aacctgagcc aggctttcaa 12660
gaacttgcag ggactgtggg gcgtgcaggc cccggtcggg gaccgcgcga cggtgtcgag 12720
cctgctgacg ccgaactcgc gcctgctgct gctgctggtg gcgcccttca cggacagcgg 12780
cagcgtgagc cgcgactcgt acctgggcta cctgcttaac ctgtaccgcg aggccatcgg 12840
gcaggcgcac gtggacgagc agacctacca ggagatcacc cacgtgagcc gcgcgctggg 12900
ccaggaggac ccgggcaacc tggaggccac cctgaacttc ctgctgacca accggtcgca 12960
gaagatcccg ccccagtacg cgctgagcac cgaggaggag cgcatcctgc gctacgtgca 13020
gcagagcgtg gggctgttcc tgatgcagga gggggccacg cccagcgccg cgctcgacat 13080
gaccgcgcgc aacatggagc ccagcatgta cgcccgcaac cgcccgttca tcaataagct 13140
gatggactac ttgcatcggg cggccgccat gaactcggac tactttacca acgccatctt 13200
gaacccgcac tggctcccgc cgcccgggtt ctacacgggc gagtacgaca tgcccgaccc 13260
caacgacggg ttcctgtggg atgacgtgga cagcagcgtg ttctcgccgc gtcccaccac 13320
caccgtgtgg aagaaagagg gcggggaccg gcggccgtcc tcggcgctgt ccggtcgcgc 13380
gggtgctgcc gcggcggtgc ccgaggccgc cagccccttt ccgagcctgc cctttttcgct 13440 gaacagcgtg cgcagcagcg agctgggtcg gctgacgcgg ccgcgcctgc tgggcgagga 13500
ggagtacctg aacgactcct tgttgaggcc cgagcgcgaa aagaacttcc ccaataacgg 13560
gatagagagc ctggtggaca agatgagccg ctggaagacg tacgcgcacg agcacaggga 13620
cgagccccga gctagcagcg caggcacccg tagacgccag cggcacgaca ggcagcgggg 13680
tctggtgtgg gacgatgagg attccgccga cgacagcagc gtgttggact tgggtgggag 13740
tggtggtggt aacccgttcg ctcacttgcg cccccgtatc gggcgcctga tgtaagaatc 13800 tgaaaaaataa aaaacggtac tcaccaaggc catggcgacc agcgtgcgtt cttctctgtt 13860
gtttgtagta gtatgatgag gcgcgtgtac ccggagggtc ctcctccctc gtacgagagc 13920

-continued

```
gtgatgcagc aggcggtggc ggcggcgatg cagccccgc tggaggcgcc ttacgtgccc  13980
ccgcggtacc tggcgcctac ggaggggcgg aacagcattc gttactcgga gctggcaccc  14040
ttgtacgata ccacccggtt gtacctggtg gacaacaagt cggcggacat cgcctcgctg  14100
aactaccaga acgaccacag caacttcctg accaccgtgg tgcagaacaa cgatttcacc  14160
cccacggagg ccagcaccca gaccatcaac tttgacgagc gctcgcggtg gggcggccag  14220
ctgaaaacca tcatgcacac caacatgccc aacgtgaacg agttcatgta cagcaacaag  14280
ttcaaggcgc gggtgatggt ctcgcgcaag acccccaacg gggtcacagt aacagatggt  14340
agtcaggacg agctgaccta cgagtgggtg gagtttgagc tgcccgaggg caacttctcg  14400
gtgaccatga ccatcgatct gatgaacaac gccatcatcg acaactactt ggcggtgggg  14460
cggcagaacg gggtgctgga gagcgacatc ggcgtgaagt tcgacacgcg caacttccgg  14520
ctgggctggg accccgtgac cgagctggtg atgccgggcg tgtacaccaa cgaggccttc  14580
caccccgaca tcgtcctgct gcccggctgc ggcgtggact tcaccgagag ccgcctcagc  14640
aacctgctgg gcatccgcaa gcggcagccc ttccaggagg gcttccagat cctgtacgag  14700
gacctggagg ggggcaacat ccccgcgctc ttggatgtcg aagcctacga gaaaagcaag  14760
gaggatagca ccgccgtggc taccgccgcg actgtggcag atgccactgt caccaggggc  14820
gatacattcg ccacccaggc ggaggaagca gccgccctag cggcgaccga tgatagtgaa  14880
agtaagatag ttatcaagcc ggtggagaag gacagcaagg acaggagcta caacgttcta  14940
tcggatggaa agaacaccgc ctaccgcagc tggtacctgg cctacaacta cggcgacccc  15000
gagaagggcg tgcgctcctg gacgctgctc accacctcgg acgtcacctg cggcgtggag  15060
caagtctact ggtcgctgcc cgacatgatg caagacccgg tcaccttccg ctccacgcgt  15120
caagttagca actacccggt ggtgggcgcc gagctcctgc ccgtctactc caagagcttc  15180
ttcaacgagc aggccgtcta ctcgcagcag ctgcgcgcct tcacctcgct cacgcacgtc  15240
ttcaaccgct tccccgagaa ccagatcctc gtccgcccgc ccgcgcccac cattaccacc  15300
gtcagtgaaa acgttcctgc tctcacagat cacgggaccc tgccgctgcg cagcagtatc  15360
cggggagtcc agcgcgtgac cgtcactgac gccagacgcc gcacctgccc ctacgtctac  15420
aaggccctgg gcgtagtcgc gccgcgcgtc ctctcgagcc gcaccttcta aaaaatgtcc  15480
attctcatct cgcccagtaa taacaccggt tggggcctgc gcgcgcccag caagatgtac  15540
ggaggcgctc gccaacgctc cacgcaacac cccgtgcgcg tgcgcgggca cttccgcgct  15600
ccctggggcg ccctcaaggg tcgcgtgcgc tcgcgcacca ccgtcgacga cgtgatcgac  15660
caggtggtgg ccgacgcgcg caactacacg cccgccgccg cgcccgcctc caccgtggac  15720
gccgtcatcg acagcgtggt ggccgacgcg cgccggtacg cccgcgccaa gagccggcgg  15780
cggcgcatcg cccggcggca ccggagcacc cccgccatgc gcgcggcgcg agccttgctg  15840
cgcagggcca ggcgcacggg acgcagggcc atgctcaggg cggccagacg cgcggcctcc  15900
ggcagcagca gcgccggcag gacccgcaga cgcgcggcca cggcggcggc ggcggccatc  15960
gccagcatgt cccgcccgcg gcgcggcaac gtgtactggg tgcgcgacgc cgccaccggt  16020
gtgcgcgtgc ccgtgcgcac ccgcccccct cgcacttgaa gatgctgact tcgcgatgtt  16080
gatgtgtccc agcggcgagg aggatgtcca agcgcaaata caaggaagag atgctccagg  16140
tcatcgcgcc tgagatctac ggccccgcgg cggcggtgaa ggaggaaaga aagccccgca  16200
aactgaagcg ggtcaaaaag gacaaaaagg aggaggaaga tgtggacgga ctggtggagt  16260
ttgtgcgcga gttcgccccc cggcggcgcg tgcagtggcg cgggcggaaa gtgaaaccgg  16320
```

-continued

```
tgctgcggcc cggcaccacg gtggtcttca cgcccggcga gcgttccggc tccgcctcca  16380
agcgctccta cgacgaggtg tacggggacg aggacatcct cgagcaggcg gccgagcgtc  16440
tgggcgagtt tgcttacggc aagcgcagcc gccccgcgcc cttgaaagag gaggcggtgt  16500
ccatcccgct ggaccacggc aaccccacgc cgagcctgaa gccggtgacc ctgcagcagg  16560
tgctgccgag cgcggcgccg cgccggggct tcaagcgcga gggcggcgag gatctgtacc  16620
cgaccatgca gctgatggtg cccaagcgcc agaagctgga ggacgtgctg gagcacatga  16680
aggtggaccc cgaggtgcag cccgaggtca aggtgcggcc catcaagcag gtggccccgg  16740
gcctgggcgt gcagaccgtg gacatcaaga tccccacgga gcccatggaa acgcagaccg  16800
agcccgtgaa gcccagcacc agcaccatgg aggtgcagac ggatccctgg atgccggcgc  16860
cggcttccac caccactcgc cgaagacgca agtacggcgc ggccagcctg ctgatgccca  16920
actacgcgct gcatccttcc atcatcccca cgccgggcta ccgcggcacg cgcttctacc  16980
gcggctacag cagccgccgc aagaccacca cccgccgccg ccgtcgccgc acccgccgca  17040
gcaccaccgc gacttccgcc gccgccttgg tgcggagagt gtaccgcagc gggcgtgagc  17100
ctctgaccct gccgcgcgcg cgctaccacc cgagcatcgc catttaactc tgccgtcgcc  17160
tccttgcaga tatggccctc acatgccgcc tccgcgtccc cattacgggc taccgaggaa  17220
gaaagccgcg ccgtagaagg ctgacgggga acgggctgcg tcgccatcac caccggcggc  17280
ggcgcgccat cagcaagcgg ttgggggag gcttcctgcc cgcgctgatc cccatcatcg  17340
ccgcggcgat cggggcgatc cccggcatag cttccgtggc ggtgcaggcc tctcagcgcc  17400
actgagacac agcttggaaa atttgtaata aaaaaatgga ctgacgctcc tggtcctgtg  17460
atgtgtgttt ttagatggaa gacatcaatt tttcgtccct ggcaccgcga cacggcacgc  17520
ggccgtttat gggcacctgg agcgacatcg gcaacagcca actgaacggg ggcgccttca  17580
attggagcag tctctggagc gggcttaaga atttcgggtc cacgctcaaa acctatggca  17640
acaaggcgtg gaacagcagc acagggcagg cgctgaggga aaagctgaaa gagcagaact  17700
tccagcagaa ggtggtcgat ggcctggcct cgggcatcaa cggggtggtg gacctggcca  17760
accaggccgt gcagaaacag atcaacagcc gcctggacgc ggtcccgccc gcggggtccg  17820
tggagatgcc ccaggtggag gaggagctgc ctcccctgga caagcgcggc gacaagcgac  17880
cgcgtcccga cgcggaggag acgctgctga cgcacacgga cgagccgccc ccgtacgagg  17940
aggcggtgaa actgggtctg cccaccacgc ggcccgtggc gcctctggcc accggggtgc  18000
tgaaacccag cagcagcagc agccagcccg cgaccctgga cttgcctcca cctcgcccct  18060
ccacagtggc taagcccctg ccgccggtgg ccgtcgcgtc gcgcgccccc cgaggccgcc  18120
cccaggcgaa ctggcagagc actctgaaca gcatcgtggg tctgggagtg cagagtgtga  18180
agcgccgccg ctgctattaa aagacactgt agcgcttaac ttgcttgtct gtgtgtatat  18240
gtatgtccgc cgaccagaag gaggaggaag aggcgcgtcg ccgagttgca agatggccac  18300
cccatcgatg ctgccccagt gggcgtacat gcacatcgcc ggacaggacg cttcggagta  18360
cctgagtccg ggtctggtgc agttcgcccg cgccacagac acctacttca gtctggggaa  18420
caagtttagg aaccccacgg tggcacccac gcacgatgtg accaccgacc gcagccagcg  18480
gctgacgctg cgcttcgtgc ccgtggaccg cgaggacaac acctactcgt acaaagtgcg  18540
ctacacgctg gccgtgggcg acaaccgcgt gctggacatg gccagcacct actttgacat  18600
ccgcggcgtg ctggatcggg gccccagctt caaaccctac tccggcaccg cctacaacag  18660
cctggctccc aagggagcgc ccaacacctc acagtggata accaaagaca atggaactga  18720
```

-continued

```
taagacatac agttttggaa atgctccagt cagaggattg gacattacag aagagggtct  18780
ccaaatagga accgatgagt caggggggtga aagcaagaaa atttttgcag acaaaaccta  18840
tcagcctgaa cctcagcttg gagatgagga atggcatgat actattggag ctgaagacaa  18900
gtatggaggc agagcgctta aacctgccac caacatgaaa ccctgctatg ggtctttcgc  18960
caagccaact aatgctaagg gaggtcaggc taaaagcaga accaaggacg atggcactac  19020
tgagcctgat attgacatgg ccttctttga cgatcgcagt cagcaagcta gtttcagtcc  19080
agaacttgtt ttgtatactg agaatgtcga tctggacacc ccggataccc acattattta  19140
caaacctggc actgatgaaa caagttcttc tttcaacttg ggtcagcagt ccatgcccaa  19200
cagacccaac tacattggct tcagagacaa ctttatcggg ctcatgtact acaacagcac  19260
tggcaatatg ggtgtactgg ccggtcaggc ctcccagctg aatgctgtgg tggacttgca  19320
ggacagaaac actgaactgt cctaccagct cttgcttgac tctctgggtg acagaaccag  19380
gtatttcagt atgtggaatc aggcggtgga cagctatgac cccgatgtgc gcattattga  19440
aaatcacggt gtggaggatg aactccccaa ctattgcttc cctttgaatg gtgtgggctt  19500
tacagataca ttccagggaa ttaaggttaa aactacaaat aacggaacag caaatgctac  19560
agagtgggaa tctgatacct ctgtcaataa tgctaatgag attgccaagg gcaatccttt  19620
cgccatggag atcaacatcc aggccaacct gtggcggaac ttcctctacg cgaacgtggc  19680
gctgtacctg cccgactcct acaagtacac gccggccaac atcacgctgc ccaccaacac  19740
caacacctac gattacatga acggccgcgt ggtggcgccc tcgctggtgg acgcctacat  19800
caacatcggg gcgcgctggt cgctggaccc catggacaac gtcaacccct tcaaccacca  19860
ccgcaacgcg ggcctgcgct accgctccat gctcctgggc aacgggcgct acgtgccctt  19920
ccacatccag gtgccccaaa agtttttcgc catcaagagc ctcctgctcc tgcccgggtc  19980
ctacacctac gagtggaact tccgcaagga cgtcaacatg atcctgcaga gctccctcgg  20040
caacgacctg cgcacggacg gggcctccat cgccttcacc agcatcaacc tctacgccac  20100
cttcttcccc atggcgcaca acaccgcctc cacgctcgag gccatgctgc gcaacgacac  20160
caacgaccag tccttcaacg actacctctc ggcggccaac atgctctacc ccatcccggc  20220
caacgccacc aacgtgccca tctccatccc ctcgcgcaac tgggccgcct tccgcggatg  20280
gtccttcacg cgcctcaaga cccgcgagac gccctcgctc ggctccgggt tcgaccccta  20340
cttcgtctac tcgggctcca tcccctacct cgacggcacc ttctacctca accacacctt  20400
caagaaggtc tccatcacct tcgactcctc cgtcagctgg cccggcaacg accgcctcct  20460
gacgcccaac gagttcgaaa tcaagcgcac cgtcgacgga gaggggtaca acgtggccca  20520
gtgcaacatg accaaggact ggttcctggt ccagatgctg gcccactaca acatcggcta  20580
ccagggcttc tacgtgcccg agggctacaa ggaccgcatg tactccttct tccgcaactt  20640
ccagcccatg agccgccagg tcgtggacga ggtcaactac aaggactacc aggccgtcac  20700
cctggcctac cagcacaaca actcgggctt cgtcggctac ctcgcgccca ccatgcgcca  20760
gggccagccc taccccgcca actaccccta cccgctcatc ggcaagagcg ccgtcgccag  20820
cgtcacccag aaaaagttcc tctgcgaccg ggtcatgtgg cgcatcccct tctccagcaa  20880
cttcatgtcc atgggcgcgc tcaccgacct cggccagaac atgctctacg ccaactccgc  20940
ccacgcgcta gacatgaatt tcgaagtcga ccccatggat gagtccaccc ttctctatgt  21000
tgtcttcgaa gtcttcgacg tcgtccgagt gcaccagccc caccgcggcg tcatcgaggc  21060
cgtctacctg cgcacgccct tctcggccgg caacgccacc acctaagcct cttgcttctt  21120
```

-continued

```
gcaagatgac ggcctgtggc tccggcgagc aggagctcag ggccatcctc cgcgacctgg  21180
gctgcgggcc ctacttcctg ggcaccttcg acaagcgctt cccgggattc atggccccgc  21240
acaagctggc ctgcgccatc gtcaacacgg ccggccgcga gaccgggggc gagcactggc  21300
tggccttcgc ctggaacccg cgcacccaca cctgctacct cttcgacccc ttcgggttct  21360
cggacgagcg cctcaagcag atctaccagt tcgagtacga gggcctgctg cgccgcagcg  21420
ccctggccac cgaggaccgc tgcgtcaccc tggaaaagtc cacccagacc gtgcagggtc  21480
cgcgctcggc cgcctgcggg ctcttctgct gcatgttcct gcacgccttc gtgcactggc  21540
ccgaccgccc catggacaag aaccccacca tgaacttgct gacgggggtg cccaacggca  21600
tgctccagtc gccccaggtg gaacccaccc tgcgccgcaa ccaggaggcg ctctaccgct  21660
tcctcaacgc ccactccgcc tactttcgct cccaccgcgc gcgcatcgag aaggccaccg  21720
ccttcgaccg catgaatcaa gacatgtaaa ctgtgtgtat gtgaatgctt tattcataat  21780
aaacagcaca tgtttatgcc accttctctg aggctctgac tttatttaga aatcgaaggg  21840
gttctgccgg ctctcggcgt gccccgcggg cagggatacg ttgcggaact ggtacttggg  21900
cagccacttg aactcgggga tcagcagctt cggcacgggg aggtcgggga acgagtcgct  21960
ccacagcttg cgcgtgagtt gcagggcgcc cagcaggtcg ggcgcggata tcttgaaatc  22020
acagttggga cccgcgttct gcgcgcgaga gttgcggtac acggggttgc agcactggaa  22080
caccatcagg gccgggtgct tcacgctcgc cagcaccgtc gcgtcggtga tgccctccac  22140
gtccagatcc tcggcgttgg ccatcccgaa gggggtcatc ttgcaggtct gccgccccat  22200
gctgggcacg cagccgggct tgtggttgca atcgcagtgc agggggatca gcatcatctg  22260
ggcctgctcg gagctcatgc ccgggtacat ggccttcatg aaagcctcca gctggcggaa  22320
ggcctgctgc gccttgccgc cctcggtgaa gaagaccccg caggacttgc tagagaactg  22380
gttggtggcg cagccggcgt cgtgcacgca gcagcgcgcg tcgttgttgg ccagctgcac  22440
cacgctgcgc ccccagcggt tctgggtgat cttggcccgg tcggggttct ccttcagcgc  22500
gcgctgcccg ttctcgctcg ccacatccat ctcgatcgtg tgctccttct ggatcatcac  22560
ggtcccgtgc aggcaccgca gcttgccctc ggcttcggtg catccgtgca gccacagcgc  22620
gcagccggtg cactcccagt tcttgtgggc gatctgggag tgcgagtgca cgaagccctg  22680
caggaagcgg cccatcatcg cggtcagggt cttgttgctg gtgaaggtca gcgggatgcc  22740
gcggtgctcc tcgttcacat acaggtggca gatgcggcgg tacacctcgc cctgctcggg  22800
catcagctgg aaggcggact tcaggtcgct ctccacgcgg taccgctcca tcagcagcgt  22860
catgacttcc atgcccttct cccaggccga aacgatcggc aggctcaggg ggttcttcac  22920
cgttgtcatc ttagtcgccg ccgccgaggt cagggggtcg ttctcgtcca gggtctcaaa  22980
cactcgcttg ccgtccttct cggtgatgcg cacgggggga aagctgaagc ccacggccgc  23040
cagctcctcc tcggcctgcc tttcgtcctc gctgtcctgg ctgatgtctt gcaaaggcac  23100
atgcttggtc ttgcggggtt tctttttggg cggcagaggc ggcggcggag acgtgctggg  23160
cgagcgcgag ttctcgctca ccacgactat ttcttcttct tggccgtcgt ccgagaccac  23220
gcggcggtag gcatgcctct tctggggcag aggcggaggc gacgggctct cgcggttcgg  23280
cgggcggctg gcagagcccc ttccgcgttc gggggtgcgc tcctggcggc gctgctctga  23340
ctgacttcct ccgcggccgg ccattgtgtt ctcctaggga gcaagcatgg agactcagcc  23400
atcgtcgcca acatcgccat ctgcccccgc cgccgccgac gagaaccagc agcagcagaa  23460
tgaaagctta accgccccgc cgcccagccc cacctccgac gccgcggccc cagacatgca  23520
```

-continued

```
agagatggag gaatccatcg agattgacct gggctacgtg acgcccgcgg agcacgagga  23580
ggagctggca gcgcgctttt cagccccgga agagaaccac caagagcagc cagagcagga  23640
agcagagagc gagcagagcc aggctgggct cgagcatggc gactacctga gcggggcaga  23700
ggacgtgctc atcaagcatc tggcccgcca atgcatcatc gtcaaggatg cgctgctcga  23760
ccgcgccgag gtgcccctca gcgtggcgga gctcagccgc gcctacgagc gcaacctctt  23820
ctcgccgcgc gtgcccccca agcgccagcc caacggcacc tgcgagccca acccgcgcct  23880
caacttctac ccggtcttcg cggtgcccga ggccctggcc acctaccacc tctttttcaa  23940
gaaccaaagg atccccgtct cctgccgcgc caaccgcacc cgcgccgacg ccctgctcaa  24000
cctgggcccc ggcgcccgcc tacctgatat cgcctccttg gaagaggttc ccaagatctt  24060
cgagggtctg ggcagcgacg agactcgggc cgcgaacgct ctgcaaggaa gcggagagga  24120
gcatgagcac cacagcgccc tggtggagtt ggaaggcgac aacgcgcgcc tggcggtcct  24180
caagcgcacg gtcgagctga cccacttcgc ctacccggcg ctcaacctgc cccccaaggt  24240
catgagcgcc gtcatggacc aggtgctcat caagcgcgcc tcgcccctct cggaggagga  24300
gatgcaggac cccgagagct cggacgaggg caagcccgtg gtcagcgacg agcagctggc  24360
gcgctggctg ggagcgagta gcaccccccca gagcctggaa gagcggcgca agctcatgat  24420
ggccgtggtc ctggtgaccg tggagctgga gtgtctgcgc cgcttcttcg ccgacgcgga  24480
gaccctgcgc aaggtcgagg agaacctgca ctacctcttc aggcacgggt tcgtgcgcca  24540
ggcctgcaag atctccaacg tggagctgac caacctggtc tcctacatgg gcatcctgca  24600
cgagaaccgc ctggggcaga acgtgctgca caccaccctg cgcggggagg cccgccgcga  24660
ctacatccgc gactgcgtct acctgtacct ctgccacacc tggcagacgg gcatgggcgt  24720
gtggcagcag tgcctggagg agcagaacct gaaagagctc tgcaagctcc tgcagaagaa  24780
cctgaaggcc ctgtggaccg ggttcgacga gcgcaccacc gcctcggacc tggccgacct  24840
catcttcccc gagcgcctgc ggctgacgct gcgcaacggg ctgcccgact ttatgagcca  24900
aagcatgttg caaaactttc gctctttcat cctcgaacgc tccgggatcc tgcccgccac  24960
ctgctccgcg ctgccctcgg acttcgtgcc gctgaccttc cgcgagtgcc ccccgccgct  25020
ctggagccac tgctacctgc tgcgtctggc caactacctg gcctaccact cggacgtgat  25080
cgaggacgtc agcggcgagg gtctgctcga gtgccactgc cgctgcaacc tctgcacgcc  25140
gcaccgctcc ctggcctgca acccccagct gctgagcgag acccagatca tcggcacctt  25200
cgagttgcaa ggccccggcg aggagggcaa ggggggtctg aaactcaccc cggggctgtg  25260
gacctcggcc tacttgcgca agttcgtgcc cgaggactac catcccttcg agatcaggtt  25320
ctacgaggac caatcccagc cgcccaaggc cgagctgtcg gcctgcgtca tcacccaggg  25380
ggccatcctg gcccaattgc aagccatcca gaaatcccgc caagaatttc tgctgaaaaa  25440
gggccacggg gtctacttgg acccccagac cggagaggag ctcaaccccca gcttccccca  25500
ggatgcccag aggaagcagc aagaagctga aagtggagct gccgctgccg ccggaggatt  25560
tggaggaaga ctgggagagc agtcaggcag aggaggagga gatggaagac tgggacagca  25620
ctcaggcaga ggaggacagc ctgcaagaca gtctggaaga cgaggtggag gaggaggcag  25680
aggaagaagc agccgccgcc agaccgtcgt cctcggcgga gaaagcaagc agcacggata  25740
ccatctccgc tccgggtcgg ggtctcggcg gccgggccca cagtaggtgg gacgagaccg  25800
ggcgcttccc gaaccccacc acccagaccg gtaagaagga gcggcaggga tacaagtcct  25860
ggcgggggca caaaaacgcc atcgtctcct gcttgcaagc ctgcgggggc aacatctcct  25920
```

-continued

```
tcacccggcg ctacctgctc ttccaccgcg gggtgaactt cccccgcaac atcttgcatt  25980
actaccgtca cctccacagc ccctactact gtttccaaga agaggcagaa acccagcagc  26040
agcagaaaac cagcagcagc tagaaaatcc acagcggcgg cggcggcagg tggactgagg  26100
atcgcggcga acgagccggc gcagacccgg gagctgagga accggatctt tcccaccctc  26160
tatgccatct tccagcagag tcgggggcag gagcaggaac tgaaagtcaa gaaccgttct  26220
ctgcgctcgc tcacccgcag ttgtctgtat cacaagagcg aagaccaact tcagcgcact  26280
ctcgaggacg ccgaggctct cttcaacaag tactgcgcgc tcactcttaa agagtagccc  26340
gcgcccgccc acacacggaa aaaggcggga attacgtcac cacctgcgcc cttcgcccga  26400
ccatcatcat gagcaaagag attcccacgc cttacatgtg gagctaccag ccccagatgg  26460
gcctggccgc cggcgccgcc caggactact ccacccgcat gaactggctc agtgccgggc  26520
ccgcgatgat ctcacgggtg aatgacatcc gcgcccgccg aaaccagata ctcctagaac  26580
agtcagcgat caccgccacg ccccgccatc accttaatcc gcgtaattgg cccgccgccc  26640
tggtgtacca ggaaattccc cagcccacga ccgtactact tccgcgagac gcccaggccg  26700
aagtccagct gactaactca ggtgtccagc tggccggcgg cgccgccctg tgtcgtcacc  26760
gccccgctca gggtataaag cggctggtga tccgaggcag aggcacacag ctcaacgacg  26820
aggtggtgag ctcttcgctg ggtctgcgac ctgacggagt cttccaactc gccggatcgg  26880
ggagatcttc cttcacgcct cgtcaggccg tcctgacttt ggagagttcg tcctcgcagc  26940
cccgctcggg tggcatcggc actctccagt tcgtggagga gttcactccc tcggtctact  27000
tcaacccctt ctccggctcc cccggccact acccggacga gttcatcccg aacttcgacg  27060
ccatcagcga gtcggtggac ggctacgatt gaatgtccca tggtggcgcg gctgacctag  27120
ctcggcttcg acacctggac cactgccgcc gcttccgctg cttcgctcgg gatctcgccg  27180
agtttgccta ctttgagctg cccgaggagc accctcaggg cccggcccac ggagtgcgga  27240
tcatcgtcga agggggcctc gactcccacc tgcttcggat cttcagccag cgtccgatcc  27300
tggtcgagcg cgagcaagga cagacccgtc tgaccctgta ctgcatctgc aaccaccccg  27360
gcctgcatga aagtctttgt tgtctgctgt gtactgagta taataaaagc tgagatcagc  27420
gactactccg gacttccgtg tgttcctgaa tccatcaacc agtccctgtt cttcaccggg  27480
aacgagaccg agctccagct ccagtgtaag ccccacaaga agtacctcac ctggctgttc  27540
cagggctccc cgatcgccgt tgtcaaccac tgcgacaacg acggagtcct gctgagcggc  27600
cctgccaacc ttactttttc cacccgcaga agcaagctcc agctcttcca acccttcctc  27660
cccgggacct atcagtgcgt ctcgggaccc tgccatcaca ccttccacct gatcccgaat  27720
accacagcgt cgctccccgc tactaacaac caaactaccc accaacgcca ccgtcgcgac  27780
ctttcctctg aatctaatac cactaccgga ggtgagctcc gaggtcgacc aacctctggg  27840
atttactacg gcccctggga ggtggtgggg ttaatagcgc taggcctagt tgtgggtggg  27900
cttttggctc tctgctacct atacctccct tgctgttcgt acttagtggt gctgtgttgc  27960
tggtttaaga aatggggcag atcaccctag tgagctgcgg tgtgctggtg gcggtggtgc  28020
tttcgattgt gggactgggc ggcgcggctg tagtgaagga gaaggccgat ccctgcttgc  28080
atttcaatcc cgacaaatgc cagctgagtt ttcagcccga tggcaatcgg tgcgcggtgc  28140
tgatcaagtg cggatgggaa tgcgagaacg tgagaatcga gtacaataac aagactcgga  28200
acaatactct cgcgtccgtg tggcagcccg gggaccccga gtggtacacc gtctctgtcc  28260
ccggtgctga cggctccccg cgcaccgtga ataatacttt catttttgcg cacatgtgcg  28320
```

-continued acacggtcat gtggatgagc aagcagtacg atatgtggcc ccccacgaag gagaacatcg 28380
tggtcttctc catcgcttac agcctgtgca cggtgctaat caccgctatc gtgtgcctga 28440
gcattcacat gctcatcgct attcgcccca gaaataatgc cgaaaaagag aaacagccat 28500
aacacgtttt ttcacacacc ttgtttttac agacaatgcg tctgttaaat tttttaaaca 28560
ttgtgctcag tattgcttat gcctctggct atgcaaacat acagaaaacc ctctatgtag 28620
gatctgatga tacactagag ggtacccaat cacaagctag ggtttcatgg tatttttata 28680
aaagctcaga taatcctatt actctttgca aaggtgatca ggggcggaca acaaagccgc 28740
ctatcacatt tagctgtacc agaacaaatc tcacgctttt ctcaattaca aaacaatatg 28800
ctggtattta ttacagtaca aactttcata gtgggcaaga taaatattat actgttaagg 28860
tagaaaatcc taccactcct agaactacca ccaccaccac caccaccacc actactgcga 28920
agcccactaa acctaaaact accaagaaaa ccactgtgaa aactacaact agaaccacca 28980
caactacaga aaccaccacc agcacaacac ttgctgcaac tacacacaca cacactgagc 29040
taaccttaca gaccactaat gatttgatag ccctgttgca aaagggggat aacagcacca 29100
cttccaatga ggagataccc aaatccatga ttggcattat tgttgctgta gtggtgtgca 29160
tgttgatcat cgccttgtgc atggtgtact atgccttctg ctacagaaag cacagactga 29220
acgacaagct ggaacactta ctaagtgttg aattttaatt ttttagaacc atgaagatcc 29280
taggcctttt agtttttctt atcattacct ctgctctatg caattctgac aatgaggacg 29340
ttactgtcgt tgtcggatca aattatacac tgaaaggtcc agcgaagggt atgctttcgt 29400
ggtattgctg gtttggaact gacactgatc aaactgagct ttgcaatgca atgaaaggtc 29460
aaataccaac ctcaaaaatt aaacataaat gcaatggtac tgacttagta ctactcaata 29520
tcacgaaatc atatgctggc agctattcat gccctggaga tgatgctgag aacatgattt 29580
tttacaaagt aactgttgtt gatcccacta ctccaccacc caccaccaca actactcaca 29640
ccacacacac agaacaaaca ccagaggcag cagaagcaga gttggccttc caggttcacg 29700
gagattcctt tgctgtcaat acccctacac ccgatcatcg gtgtccgggg ctgctagtca 29760
gcggcattgt cggtgtgctt tcgggattag cagtcataat catctgcatg ttcatttttg 29820
cttgctgcta tagaaggctt taccgacaaa aatcagaccc actgctgaac ctctatgttt 29880
aatttttttcc agagccatga aggcagttag cgctctagtt ttttgttctt tgattggcat 29940
tgtttttttgc aatcctatta ctagagttag ctttattaaa gatgtgaatg ttactgaggg 30000
gggcaatgtg acactggtag gtgtagaggg tgctaaaaac accacctgga caaaatacca 30060
ccttgggtgg aaagatattt gcaattggag tgtcactgtg tacacatgtg agggagttaa 30120
tcttaccatt gtcaatgcca cctcagctca aaatggtaga attcaaggac aaagtgttag 30180
tgtgaccagt gatgggtatt ttacccaaca tacttttatc tatgacgtta aagtcatacc 30240
actgcctacg cctagcccac ctagcaccac tacacaaaca acccacacta cacagacaac 30300
cacatacagt acatcaaatc agcctaccac cactacagca gcagaggttg ccagctcgtc 30360
tggagttcaa gtggcatttt tgttgttgcc cccatctagc agtcccactg ctattaccaa 30420
tgagcagact actgcatttt tgtccactgt cgagagccac accacagcta cctccagtgc 30480
cttctctagc accgccaatc tctcctcgct ttcctctaca ccaatcagtc ccgctactac 30540
tactaccccc gctattcttc ccactcccct gaagcaaaca gacggcggca tgcaatggca 30600
gatcaccctg ctcattgtga tcgggttggt catcctagcc gtgttgctct actacatctt 30660
ctgccgccgc attcccaacg cgcaccgcaa gccggtctac aagcccatca ttgtcgggca 30720

-continued gccggagccg cttcaggtgg aagggggtct aaggaatctt ctcttctctt ttacagtatg 30780
gtgattgaac tatgattcct agacaattct tgatcactat tcttatctgc ctcctccaag 30840
tctgtgccac cctcgctctg gtggccaacg ccagtccaga ctgtattggg cccttcgcct 30900
cctacgtgct ctttgccttc atcacctgca tctgctgctg tagcatagtc tgcctgctta 30960
tcaccttctt ccagttcatt gactggatct ttgtgcgcat cgcctacctg cgccaccacc 31020
cccagtaccg cgaccagcga gtggcgcagc tgctcaggct cctctgataa gcatgcgggc 31080
tctgctactt ctcgcgcttc tgctgttagt gctcccccgt cccgttgacc cccggccccc 31140
cactcagtcc cccgaggagg tccgcaaatg caaattccaa gaaccctgga aattcctcaa 31200
atgctaccgc caaaaatcag acatgcatcc cagctggatc atgatcattg ggatcgtgaa 31260
cattctggcc tgcaccctca tctcctttgt gatttacccc tgctttgact ttggttggaa 31320
ctcgccagag gcgctctatc tcccgcctga acctgacaca ccaccacagc aacctcaggc 31380
acacgcacta ccaccaccac agcctaggcc acaatacatg cccatattag actatgaggc 31440
cgagccacag cgacccatgc tccccgctat tagttacttc aatctaaccg gcggagatga 31500
ctgacccact ggccaacaac aacgtcaacg accttctcct ggacatggac ggccgcgcct 31560
cggagcagcg actcgcccaa cttcgcattc gccagcagca ggagagagcc gtcaaggagc 31620
tgcaggacgg catagccatc caccagtgca agaaaggcat cttctgcctg gtgaaacagg 31680
ccaagatctc ctacgaggtc acccagaccg accatcgcct ctcctacgag ctcctgcagc 31740
agcgccagaa gttcacctgc ctggtcggag tcaaccccat cgtcatcacc cagcagtcgg 31800
gcgataccaa ggggtgcatc cactgctcct gcgactcccc cgactgcgtc cacactctga 31860
tcaagaccct ctgcggcctc cgcgacctcc tccccatgaa ctaatcaccc acttatccag 31920
tgaaataaaa aaataatcat ttgatttgaa ataaagatac aatcatattg atgatttgag 31980
tttaacaaaa ataaagaatc acttacttga aatctgatac caggtctctg tccatatttt 32040
ctgccaacac cacctcactc ccctcttccc agctctggta ctgcaggccc cggcgggctg 32100
caaacttcct ccacacgctg aaggggatgt caaattcctc ctgcccctca atcttcattt 32160
tatcttctat cagatgtcca aaaagcgcgt ccgggtggat gatgacttcg accccgtcta 32220
cccctacgat gcagacaacg caccgaccgt gcccttcatc aaccccccct tcgtctcttc 32280
agatggattc caagagaagc ccctgggggt gttgtccctg cgactggccg accccgtcac 32340
caccaagaac ggggaaatca ccctcaagct gggagagggg gtggacctcg actcctcggg 32400
aaaactcatc tccaacacgg ccaccaaggc cgctgcccct ctcagttttt ccaacaacac 32460
catttccctt aacatggatc acccctttta cactaaagat ggaaaattag ccttacaagt 32520
ttctccacca ttaaatatac tgagaacaag cattctaaac acactagctt taggttttgg 32580
atcaggttta ggactccgtg gctctgcctt ggcagtacag ttagtctctc cacttacatt 32640
tgatactgat ggaaacataa agcttacctt agacagaggt ttgcatgtta caacaggaga 32700
tgcaattgaa agcaacataa gctgggctaa aggtttaaaa tttgaagatg gagccatagc 32760
aaccaacatt ggaaatgggt tagagtttgg aagcagtagt acagaaacag gtgtcgatga 32820
tgcttaccca atccaagtta aacttggatc tggccttagc tttgacagta caggagccat 32880
aatggctggt aacaaagaag acgataaact cactttgtgg acaacacctg atccatcacc 32940
aaactgtcaa atactcgcag aaaatgatgc aaaactaaca ctttgcttga ctaaatgtgg 33000
tagtcaaata ctggccactg tgtcagtctt agttgtagga agtggaaacc taaaccccat 33060
tactggcacc gtaagcagtg ctcaggtgtt tctacgtttt gatgcaaacg gtgttctttt 33120

-continued

```
aacagaacat tctacactaa aaaaatactg ggggtatagg cagggagata gcatagatgg  33180
cactccatat gtcaatgctg taggattcat gcccaattta aaagcttatc caaagtcaca  33240
aagttctact actaaaaata atatagtagg gcaagtatac atgaatggag atgtttcaaa  33300
acctatgctt ctcactataa ccctcaatgg tactgatgac agcaacagta catattcaat  33360
gtcattttca tacacctgga ctaatggaag ctatgttgga gcaacatttg gagctaactc  33420
ttataccttc tcctacatcg cccaagaatg aatactgtat cccaccctgc atgcccaacc  33480
ctcccccacc tctgtctata tggaaaactc tgaaacacaa aataaaataa agttcaagtg  33540
ttttattgat tcaacagttt tacaggattc gagcagttat ttttcctcca ccctcccagg  33600
acatggaata caccaccctc tccccccgca cagccttgaa catctgaatg ccattggtga  33660
tggacatgct tttggtctcc acgttccaca cagtttcaga gcgagccagt ctcgggtcgg  33720
tcagggagat gaaaccctcc gggcactccc gcatctgcac ctcacagctc aacagctgag  33780
gattgtcctc ggtggtcggg atcacggtta tctggaagaa gcagaagagc ggcggtggga  33840
atcatagtcc gcgaacggga tcggccggtg gtgtcgcatc aggccccgca gcagtcgctg  33900
ccgccgccgc tccgtcaagc tgctgctcag ggggtccggg tccagggact ccctcagcat  33960
gatgcccacg gccctcagca tcagtcgtct ggtgcggcgg gcgcagcagc gcatgcggat  34020
ctcgctcagg tcgctgcagt acgtgcaaca caggaccacc aggttgttca acagtccata  34080
gttcaacacg ctccagccga aactcatcgc gggaaggatg ctacccacgt ggccgtcgta  34140
ccagatcctc aggtaaatca agtggcgccc cctccagaac acgctgccca tgtacatgat  34200
ctccttgggc atgtggcggt tcaccacctc ccggtaccac atcaccctct ggttgaacat  34260
gcagccccgg atgatcctgc ggaaccacag ggccagcacc gccccgcccg ccatgcagcg  34320
aagagacccc gggtcccggc aatggcaatg gaggacccac cgctcgtacc cgtggatcat  34380
ctgggagctg aacaagtcta tgttggcaca gcacaggcac acgctcatgc atctcttcag  34440
cactctcagc tcctcggggg tcaaaaccat atcccagggc acgggaaact cttgcaggac  34500
agcgaagccc gcagaacagg gcaatcctcg cacataactt acattgtgca tggacagggt  34560
atcgcaatca ggcagcaccg ggtgatcctc caccagagaa gcgcgggtct cggtctcctc  34620
acagcgtggt aagggggccg gccgatacgg gtgatggcgg gacgcggctg atcgtgttcg  34680
cgaccgtgtc atgatgcagt tgctttcgga cattttcgta cttgctgaag cagaacctgg  34740
tccgggcgct gcacaccgat cgccggcggc ggtctcggcg cttggaacgc tcggtgttga  34800
agttgtaaaa cagccactct ctcagaccgt gcagcagatc tagggcctca ggagtgatga  34860
agatcccatc atgcctgatg gctctgatca catcgaccac cgtggaatgg gccagaccca  34920
gccagatgat gcaattttgt tgggtttcgg tgacggcggg ggagggaaga acaggaagaa  34980
ccatgattaa cttttaatcc aaacggtctc ggagcacttc aaaatgaagg tcgcggagat  35040
ggcacctctc gcccccgctg tgttggtgga aaataacagc caggtcaaag gtgatacggt  35100
tctcgagatg ttccacggtg gcttccagca aagcctccac gcgcacatcc agaaacaaga  35160
caatagcgaa agcgggaggg ttctctaatt cctcaatcat catgttacac tcctgcacca  35220
tccccagata attttcattt ttccagcctt gaatgattcg aactagttcc tgaggtaaat  35280
ccaagccagc catgataaag agctcgcgca gagcgccctc caccggcatt cttaagcaca  35340
ccctcataat tccaagatat tctgctcctg gttcacctgc agcagattga caagcgggat  35400
atcaaaatct ctgccgcgat ccctgagctc ctccctcagc aataactgta agtactcttt  35460
catatcctct ccgaaatttt tagccatagg acccccagga ataagagaag ggcaagccac  35520
```

attacagata aaccgaagtc ccccccagtg agcattgcca aatgtaagat tgaaataagc 35580
atgctggcta gacccggtga tatcttccag ataactggac agaaaatcgg gcaagcaatt 35640
tttaagaaaa tcaacaaaag aaaaatcttc caggtgcacg tttagggcct cgggaacaac 35700
gatggagtaa gtgcaagggg tgcgttccag catggttagt tagctgatct gtaaaaaaac 35760
aaaaaataaa acattaaacc atgctagcct ggcgaacagg tgggtaaatc gttctctcca 35820
gcaccaggca ggccacgggg tctccggcgc gaccctcgta aaaattgtcg ctatgattga 35880
aaaccatcac agagagacgt tcccggtggc cggcgtgaat gattcgagaa gaagcataca 35940
cccccggaac attggagtcc gtgagtgaaa aaaagcggcc gaggaagcaa tgaggcacta 36000
caacgctcac tctcaagtcc agcaaagcga tgccatgcgg atgaagcaca aaattttcag 36060
gtgcgtaaaa aatgtaatta ctcccctcct gcacaggcag cgaagctccc gatccctcca 36120
gatacacata caaagcctca gcgtccatag cttaccgagc ggcagcagca gcggcacaca 36180
acaggcgcaa gagtcagaga aaagactgag ctctaacctg tccgcccgct ctctgctcaa 36240
tatatagccc cagatctaca ctgacgtaaa ggccaaagtc taaaaatacc cgccaaataa 36300
tcacacacgc ccagcacacg cccagaaacc ggtgacacac tcaaaaaaat acgcgcactt 36360
cctcaaacgc ccaaactgcc gtcatttccg ggttcccacg ctacgtcatc aaaacacgac 36420
tttcaaattc cgtcgaccgt taaaaacgtc acccgccccg cccctaacgg tcgccgctcc 36480
cgcagccaat cagcgccccg catccccaaa ttcaaacagc tcatttgcat attaacgcgc 36540
accaaaagtt tgaggtatat tattgatgat g 36571

<210> SEQ ID NO 3
<211> LENGTH: 1109
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 3
ggagttccgc gttacataac ttacggtaaa tggcccgcct ggctgaccgc ccaacgaccc 60
ccgcccattg acgtcaataa tgacgtatgt tcccatagta acgccaatag ggactttcca 120
ttgacgtcaa tgggtggagt atttacggta aactgcccac ttggcagtac atcaagtgta 180
tcatatgcca agtacgcccc ctattgacgt caatgacggt aaatggcccg cctggcatta 240
tgcccagtac atgaccttat gggactttcc tacttggcag tacatctacg tattagtcat 300
cgctattacc atggtcgagg tgagccccac gttctgcttc actctcccca tctccccccc 360
ctccccaccc ccaattttgt atttatttat tttttaatta ttttgtgcag cgatgggggc 420
gggggggggg gggggcgcgc gccaggcggg gcggggcggg gcgaggggcg gggcggggcg 480
aggcggagag gtgcggcggc agccaatcag agcggcgcgc tccgaaagtt tccttttatg 540
gcgaggcggc ggcggcggcg gccctataaa aagcgaagcg ctccctatca gtgatagaga 600
tctccctatc agtgatagag atcgtcgacg agctcgcggc gggcgggagt cgctgcgcgc 660
tgccttcgcc ccgtgccccg ctccgccgcc gcctcgcgcc gcccgccccg gctctgactg 720
accgcgttac taaaacaggt aagtccggcc tccgcgccgg gttttggcgc ctcccgcggg 780 cgccccccctc ctcacggcga gcgctgccac gtcagacgaa gggcgcagcg agcgtcctga 840
tccttccgcc cggacgctca ggacagcggc ccgctgctca taagactcgg ccttagaacc 900
ccagtatcag cagaaggaca ttttaggacg ggacttgggt gactctaggg cactggtttt 960

-continued

```
ctttccagag agcggaacag gcgaggaaaa gtagtccctt ctcggcgatt ctgcggaggg   1020

atctccgtgg ggcggtgaac gccgatgatg cctctactaa ccatgttcat gttttctttt   1080

tttttctaca ggtcctgggt gacgaacag                                      1109


<210> SEQ ID NO 4
<211> LENGTH: 1187
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 4

ccattgcata cgttgtatcc atatcataat atgtacattt atattggctc atgtccaaca     60

ttaccgccat gttgacattg attattgact agttattaat agtaatcaat tacggggtca    120

ttagttcata gcccatatat ggagttccgc gttacataac ttacggtaaa tggcccgcct    180

ggctgaccgc ccaacgaccc ccgcccattg acgtcaataa tgacgtatgt tcccatagta    240

acgccaatag ggactttcca ttgacgtcaa tgggtggagt atttacggta aactgcccac    300

ttggcagtac atcaagtgta tcatatgcca agtacgcccc ctattgacgt caatgacggt    360

aaatggcccg cctggcatta tgcccagtac atgaccttat gggactttcc tacttggcag    420

tacatctacg tattagtcat cgctattacc atggtgatgc ggttttggca gtacatcaat    480

gggcgtggat agcggtttga ctcacgggga tttccaagtc tccaccccat tgacgtcaat    540

gggagtttgt tttggcacca aaatcaacgg gactttccaa aatgtcgtaa caactccgcc    600

ccattgacgc aaatgggcgg taggcgtgta cggtgggagg tctatataag gcgaagcgct    660

ccctatcagt gatagagatc tccctatcag tgatagagat cgtcgacgag ctcgcggcgg    720

gcgggagtcg ctgcgcgctg ccttcgcccc gtgccccgct ccgccgccgc ctcgcgccgc    780

ccgccccggc tctgactgac cgcgttacta aaacaggtaa gtccggcctc cgcgccgggt    840

tttggcgcct cccgcgggcg cccccctcct cacggcgagc gctgccacgt cagacgaagg    900

gcgcagcgag cgtcctgatc cttccgcccg gacgctcagg acagcggccc gctgctcata    960

agactcggcc ttagaacccc agtatcagca gaaggacatt ttaggacggg acttgggtga   1020

ctctagggca ctggttttct ttccagagag cggaacaggc gaggaaaagt agtcccttct   1080

cggcgattct gcggagggat ctccgtgggg cggtgaacgc cgatgatgcc tctactaacc   1140

atgttcatgt tttctttttt tttctacagg tcctgggtga cgaacag                  1187
```

REPLICATION COMPETENT ADENOVIRAL VECTORS

CROSS-REFERENCE TO RELATED APPLICATIONS

This application is filed pursuant to 35 U.S.C. § 371 as a United States National Phase Application of International Application No. PCT/EP2018/078206 filed 16 Oct. 2018, which claims priority to U.S. Provisional Patent Application No. 62/572,927, filed on 16 Oct. 2017, the complete contents of each of which are hereby incorporated by reference for all purposes.

SEQUENCE LISTING

The instant application contains a Sequence Listing which has been submitted electronically in ASCII format and is hereby incorporated by reference in its entirety. Said ASCII copy, created on Sep. 28, 2018, is named VU66430_WO_SL.txt and is 100,598 bytes in size.

FIELD OF THE INVENTION

This invention is in the field of recombinant adenoviruses. It provides isolated replication competent adenoviral vectors, recombinant polynucleotides, polypeptides, vectors and compositions comprising polynucleotide and polypeptide sequences.

BACKGROUND OF THE INVENTION

Human adenoviruses have been widely used for gene transfer applications due to their large transgene capacity and ability to achieve highly efficient gene transfer in a variety of target tissues. Recombinant adenoviruses are useful in gene therapy and as vaccines. Viral vectors based on simian adenoviruses can provide an alternative to the use of human derived adenoviral vectors for the development of nucleic acid based vaccines.

Most humans are exposed to and develop immunity to human adenoviruses. There is a demand for vectors which effectively deliver molecules to a target and minimize the effect of pre-existing immunity to human adenovirus serotypes. Simian adenoviruses are effective in this regard; they are sufficiently closely related to human viruses to be effective in inducing immunity to delivered exogenous antigens to which humans have little or no pre-existing immunity.

Replication defective adenoviruses deliver their genome to the interior of a cell and, because they do not replicate, do not amplify the transgene payload. Typically, the E1 gene is replaced with a transgene cassette comprising a promoter of choice and a nucleic acid sequence corresponding to a gene or genes of interest, resulting in a replication defective recombinant virus.

Unlike replication defective adenoviruses, replication competent adenoviruses replicate their DNA and their transgenes, thus amplifying their transgene expression to a much greater extent. Replication competent adenoviruses have the potential for greater potency but they pose a risk of spreading and infecting family members or health care workers. Despite potential safety issues, replication competent human adenoviruses have been successfully used to immunize against respiratory illness. Hundreds of thousands of United States military recruits were effectively and safely vaccinated against Acute Respiratory Disease with live, nonattenuated isolates of whole virus human Ad4, Ad7 and Ad21 formulated as enteric-coated capsules or tablets (Cancer Gene Therapy (2004) 11:819).

Human and canine replication competent vectors have been described (Vaccine (2002) 20:3485) however, no simian replication competent adenoviral vector has yet been found to be capable of delivering an immunogen or therapeutic agent for the prophylaxis or treatment of a disease. Such a vector would combine the advantages of a potent replication competent vector with the advantages of a simian adenovirus. Also, while simian vectors have the ability to replicate in human cells they replicate less well than in simian cells, thus their potency is attenuated compared to that in simians. Accordingly, there is a need in the art for vectors that combine the advantages of potent replication and no pre-existing immunity in humans.

SUMMARY OF THE INVENTION

Replication competent simian adenoviral vectors of the invention generate stronger gene-based vaccine responses than replication defective simian adenoviral vectors. The vectors of the invention have been optimized to provide improved in vivo potency while maintaining a safety profile suitable for human immunization. They have intrinsically strong immunomodulatory backbones and promoters able to drive strong and sustained transgene expression. The replication competent vectors of the invention are useful as components of immunogenic compositions for the induction of an immune response in a subject, methods for their use in treatment and processes for manufacture.

The present invention provides a replication competent simian adenoviral vector comprising an expression cassette which comprises a promoter and a transgene, wherein the expression cassette is inserted in the E3 region, the HE1 site or the HE2 site of the vector.

The present invention also provides a method of using this replication competent simian adenoviral vector to induce an immune response against a disease caused by a pathogen in a subject in need thereof.

In one embodiment the simian is a chimpanzee. The vector may be ChAd155 or ChAd83.

The replication competent chimpanzee adenoviral may further comprise a nucleotide sequence encoding a chimpanzee adenoviral fiber polypeptide or functional derivative thereof and/or a chimpanzee adenoviral E4 region.

The promoter may be chosen from a CASI promoter and an enhanced cytomegalovirus promoter. In some embodiments, the expression cassette may further comprise a posttranscriptional regulatory element. In one embodiment, the posttranscriptional regulatory element is a Woodchuck Hepatitis Postranscriptional Regulatory Element.

The transgene may be an antigen. The antigen may be chosen from a rabies virus antigen, a respiratory syncytial virus antigen, a human immunodeficiency virus antigen, a tuberculosis antigen, a malaria antigen, a hepatitis C virus antigen, a Chikungunya antigen and a hepatitis B virus antigen.

Replication competent simian adenoviral vectors were constructed by inserting a transgene expression cassette in place of the E3 region of the adenoviral genome ("RC1") (top panel), by inserting a transgene expression cassette in the HE1 region, i.e., between the stop codons of the fiber gene and the E4 region (middle panel) or by inserting a transgene expression cassette in the HE2 region, i.e., downstream of the right ITR ("RC2") (bottom panel).

Figure 2:
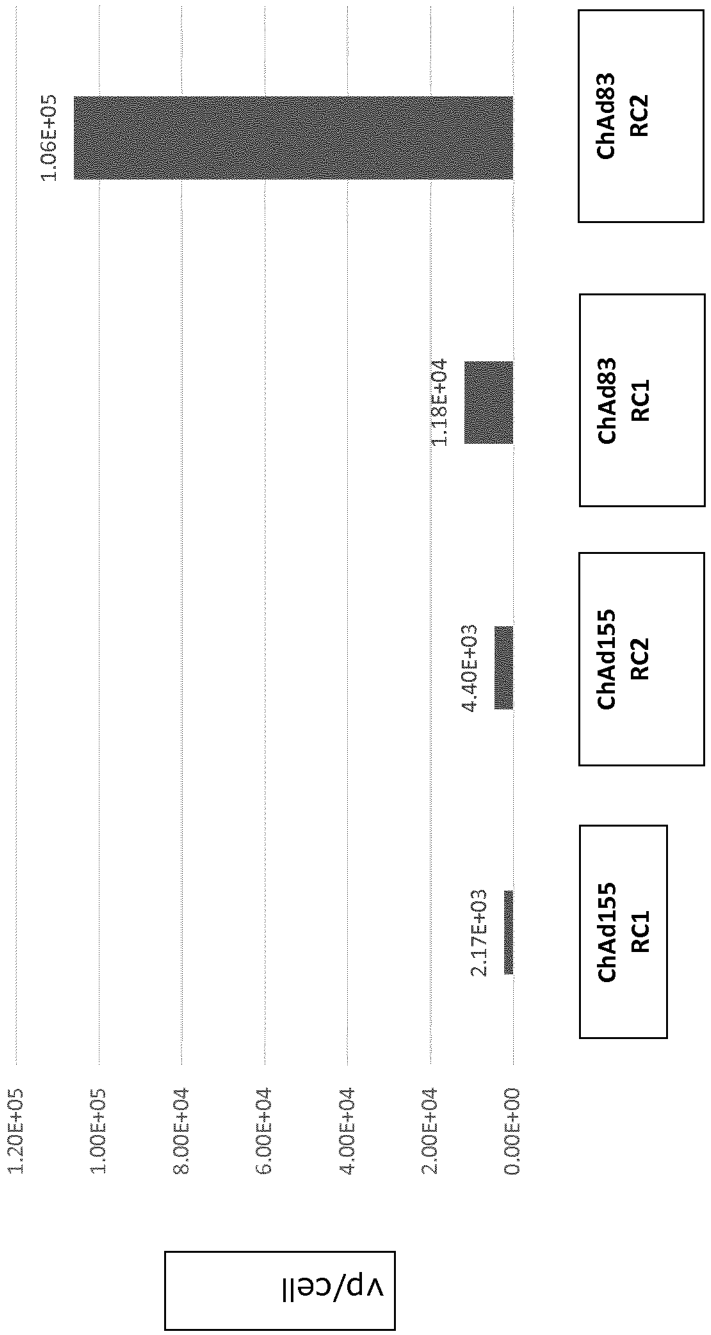

FIG. 2: Production of replication competent ChAd155 and ChAd83 expressing RC1 and RC2 vectors in a primary human cell line. The bars represent the number of viral particles expressed per cell.

Figure 3:
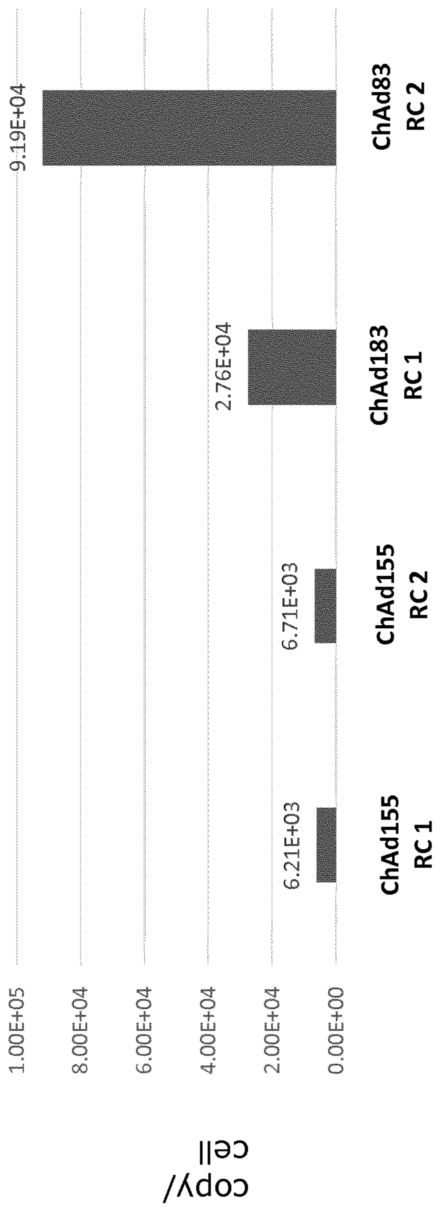

FIG. 3: Total viral genome copy number of replication competent ChAd155 and ChAd83 expressing RC1 and RC2 vectors in a primary human cell line. The bars represent the number of vector genome copies per cell.

Figure 4:
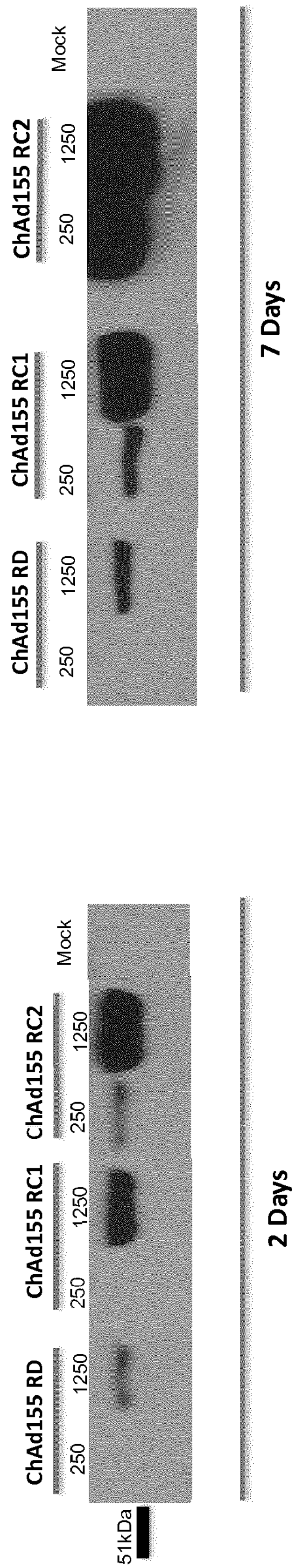

FIG. 4: Expression levels of ChAd155 replication defective (RD) and replication competent (RC1 and RC2) vectors by a primary human cell line at a multiplicity of infection of 250 and 1250. The vectors express a rabies glycoprotein transgene (51 kDa), demonstrated by western blot. The left panel shows expression on day 2 post-infection and the right panel shows expression on day 7 post-infection.

Figure 5:
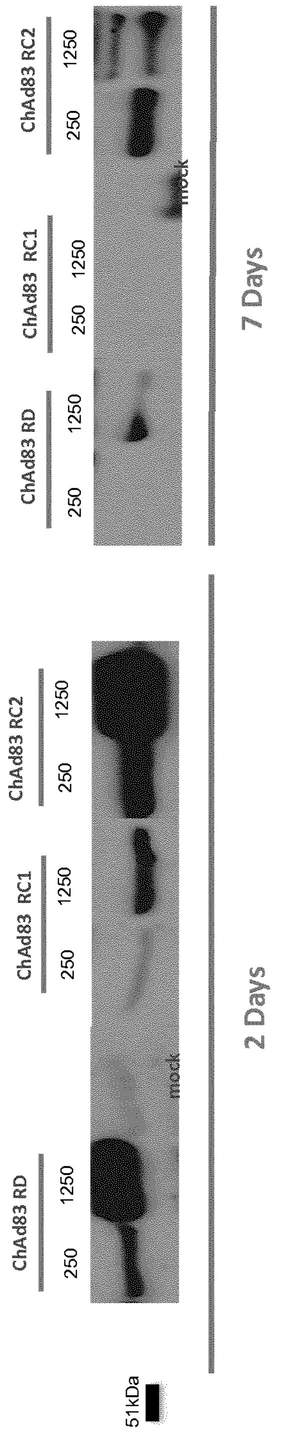

FIG. 5: Expression levels of ChAd83 replication defective (RD) and replication competent (RC1 and RC2) vectors by a primary human cell line at a multiplicity of infection of 250 and 1250. The vectors express a rabies glycoprotein transgene (51 kDa) demonstrated by western blot. The top panel shows expression on day 2 post-infection and the bottom panel shows expression on day 7 post-infection.

Figure 6:
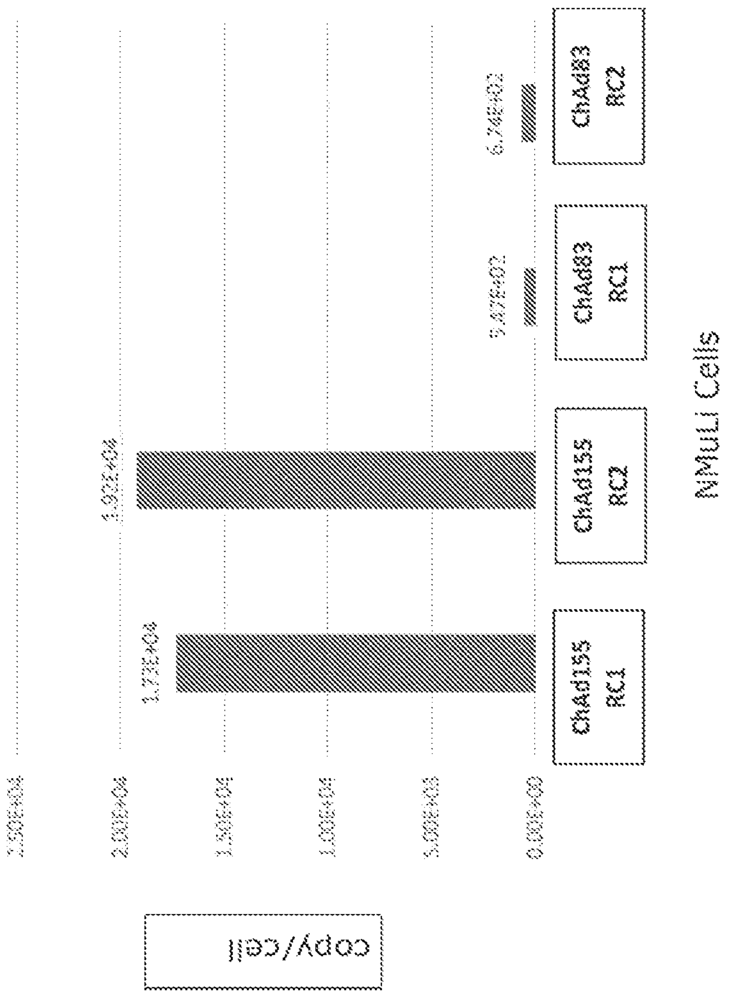
Figure 6:
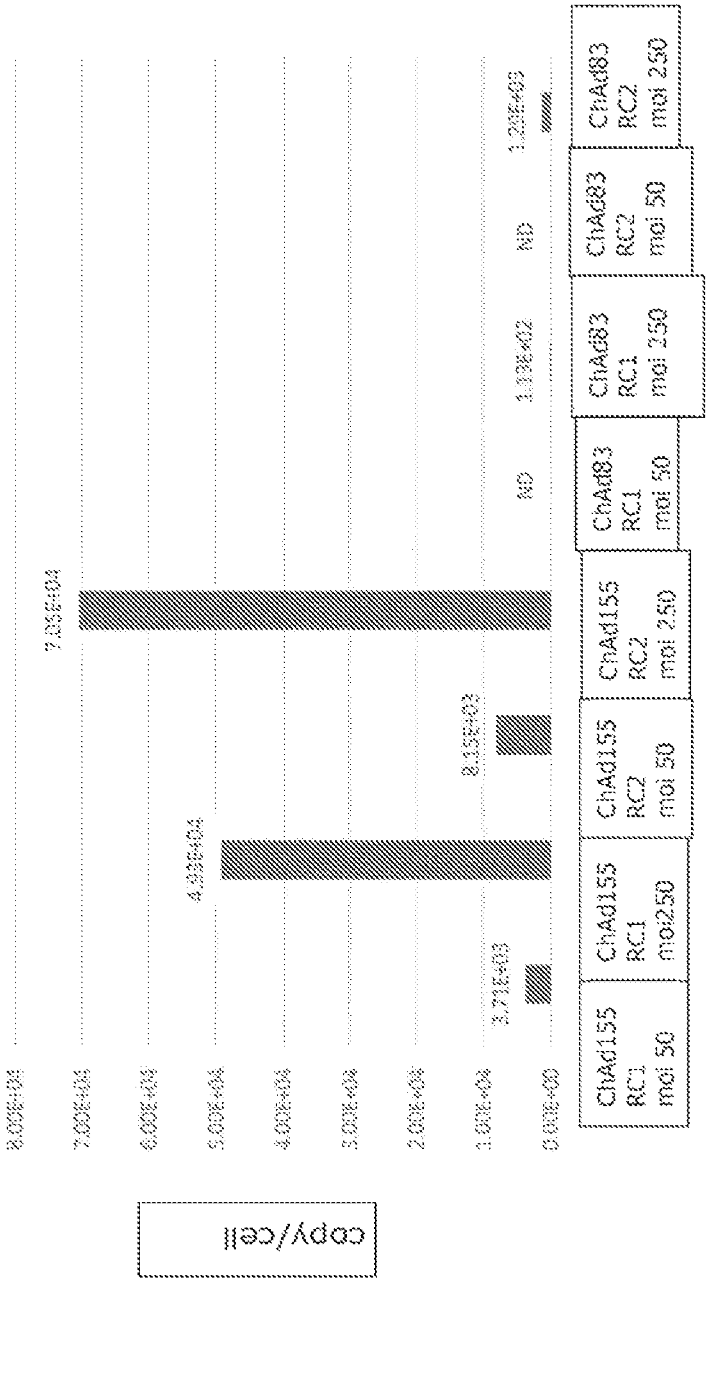

FIG. 6: Viral genome copy numbers of replication competent ChAd155 RC1 and RC2 and ChAd83 expressing RC1 and RC2 vectors in the murine cell line NMuLi (top panel) and in the Vero non-human primate cell line (bottom panel). Cells were infected at multiplicities of infection of 50 and 250.

Figure 7:
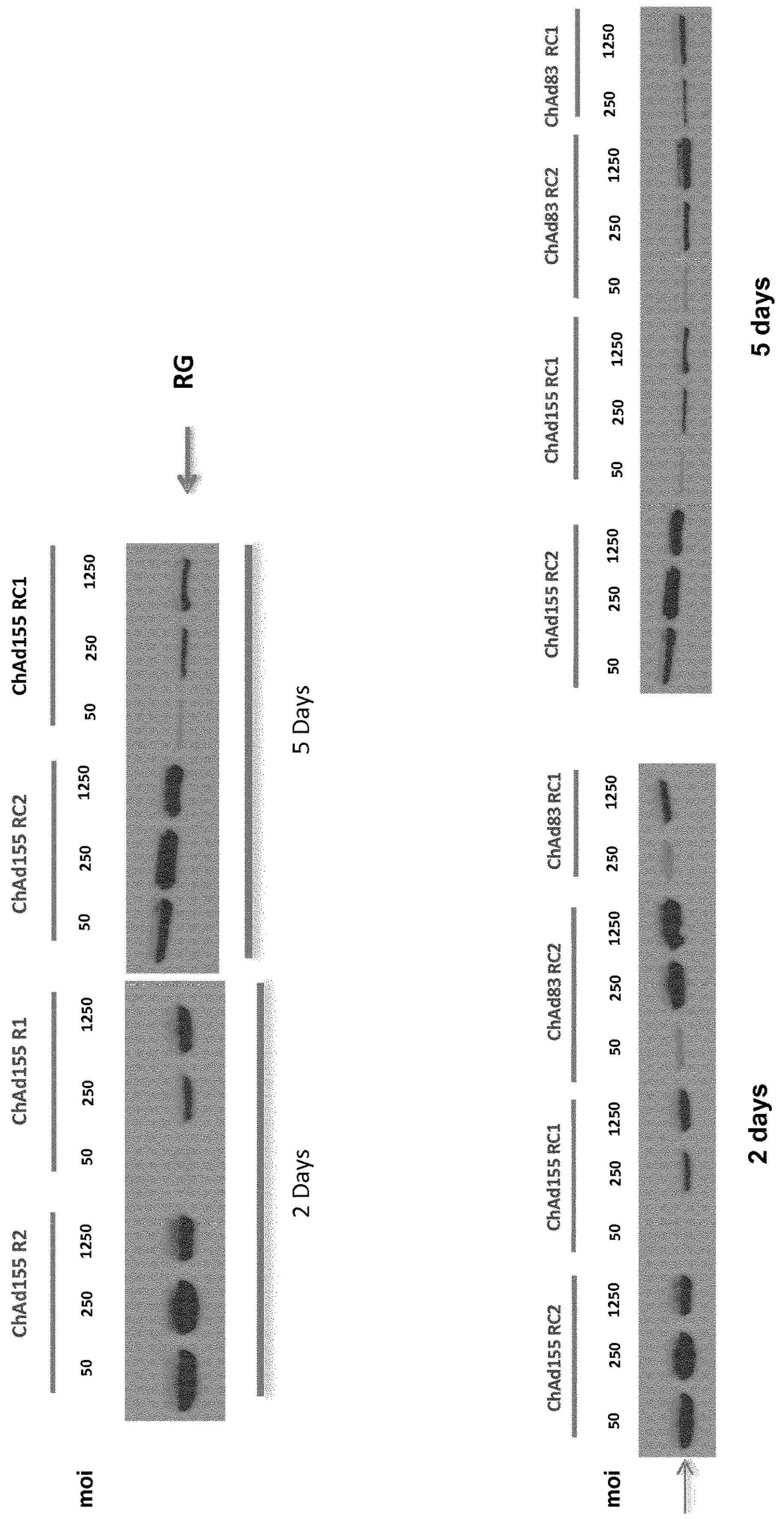

FIG. 7: Comparison of the expression levels of ChAd155 RC1 and RC2 vectors expressing a model rabies glycoprotein (RG) transgene in a murine cell line, demonstrated by western blot at two and five days post-infection (top panel). Comparison of the expression levels of ChAd155 RC1 and RC2 vectors with ChAd83 RC1 and RC2 vectors expressing a model rabies glycoprotein (RG) transgene in a murine cell line, demonstrated by western blot at two and five days post-infection (bottom panel). Cells were infected at multiplicities of infection of 50, 250 and 1250.

Figure 8:
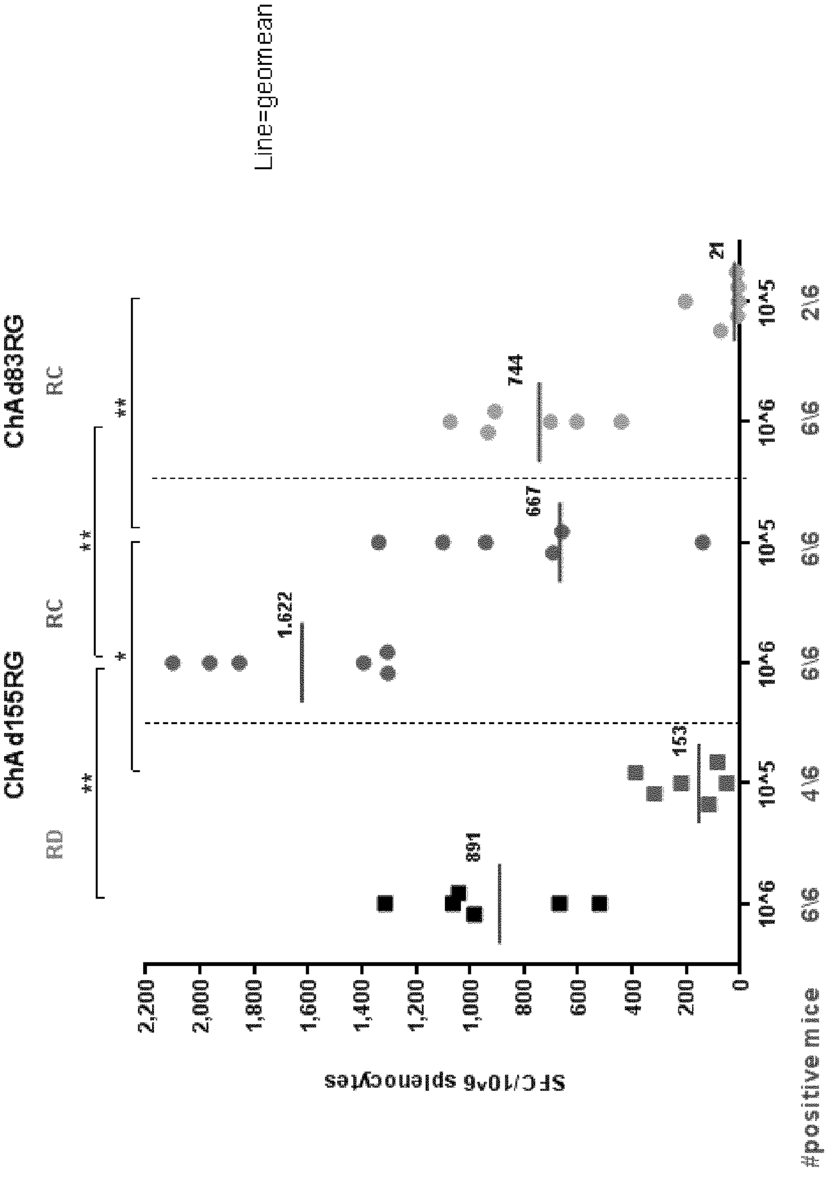

FIG. 8: Immunogenicity of ChAd155 replication defective (RD), ChAd155 RC1 and ChAd83 RC1 vectors expressing a model protein transgene in mice, measured by IFN-gamma ELISpot and expressed as spot forming cells per $10^6$ splenocytes.

Figure 9:
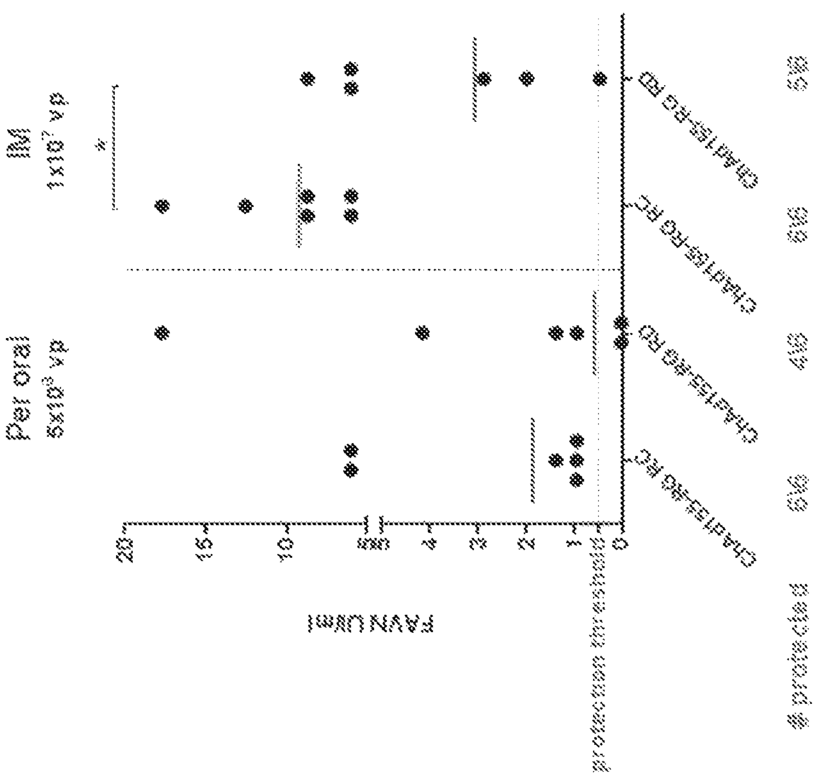
Figure 9:
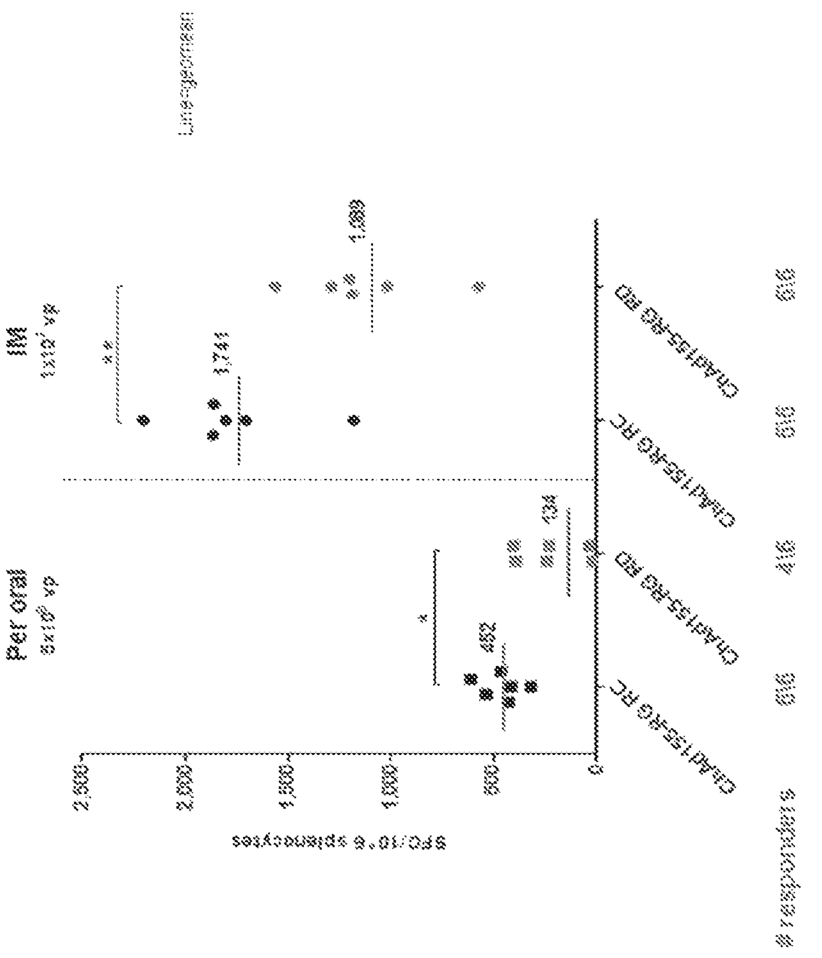

FIG. 9: Neutralizing antibody (top panel) and T cell (bottom panel responses to oral and intramuscular (IM) delivery of ChAd155 RD and ChAd155 RC1 expressing a model rabies glycoprotein protein transgene in mice. The top panel shows neutralizing antibody protection against rabies infection, measured with a fluorescent antibody virus neutralization assay (FAVN). The dotted line indicates the threshold of protection. The bottom panel shows the rabies specific T cell response, measured by interferon gamma ELIspot assay.

ANNOTATION OF THE SEQUENCES

SEQ ID NO: 1—Polynucleotide sequence encoding wild type ChAd155

SEQ ID NO: 2—Polynucleotide sequence encoding wild type ChAd83

SEQ ID NO: 3—Polynucleotide sequence encoding the CASI promoter

SEQ ID NO: 4—Polynucleotide sequence encoding the enhanced hCMV promoter

DETAILED DESCRIPTION OF THE INVENTION

Adenoviruses

Adenoviruses are nonenveloped icosahedral viruses with a linear double stranded DNA genome of approximately 36 kb. Adenoviruses can transduce numerous cell types of several mammalian species, including both dividing and nondividing cells, without integrating into the genome of the host cell. They have been widely used for gene transfer applications due to their proven safety, ability to achieve highly efficient gene transfer in a variety of target tissues, and large transgene capacity. Human adenoviral vectors are currently used in gene therapy and vaccines but have the drawback of a high worldwide prevalence of pre-existing immunity, following previous exposure to common human adenoviruses.

Adenoviruses have a characteristic morphology with an icosahedral capsid comprising three major proteins, hexon (II), penton base (III) and a knobbed fiber (IV), along with a number of other minor proteins, VI, VIII, IX, IIIa and IVa2. The hexon accounts for the majority of the structural components of the capsid, which consists of 240 trimeric hexon capsomeres and 12 penton bases. The hexon has three conserved double barrels and the top has three towers, each tower containing a loop from each subunit that forms most of the capsid. The base of the hexon is highly conserved between adenoviral serotypes, while the surface loops are variable. The penton is another adenoviral capsid protein; it forms a pentameric base to which the fiber attaches. The trimeric fiber protein protrudes from the penton base at each of the 12 vertices of the capsid and is a knobbed rod-like structure. The primary role of the fiber protein is to tether the viral capsid to the cell surface via the interaction of the knob region with a cellular receptor. Variations in the flexible shaft, as well as knob regions of fiber, are characteristic of the different adenoviral serotypes.

The adenoviral genome has been well characterized. The linear, double-stranded DNA is associated with the highly basic protein VII and a small peptide pX (also termed mu). Another protein, V, is packaged with this DNA-protein complex and provides a structural link to the capsid via protein VI. There is general conservation in the overall organization of the adenoviral genome with respect to specific open reading frames being similarly positioned, e.g. the location of the E1A, E1B, E2A, E2B, E3, E4, L1, L2, L3, L4 and L5 genes of each virus. Each extremity of the adenoviral genome comprises a sequence known as an inverted terminal repeat (ITR), which is necessary for viral replication. The 5' end of the adenoviral genome contains the 5' cis-elements necessary for packaging and replication; i.e., the 5' ITR sequences (which can function as origins of replication) and the native 5' packaging enhancer domains, which contain sequences necessary for packaging linear adenoviral genomes and enhancer elements for the E1 promoter. The 3' end of the adenoviral genome includes 3' cis-elements, including the ITRs, necessary for packaging and encapsidation. The virus also comprises a virus-encoded protease, which is necessary for processing some of the structural proteins required to produce infectious virions.

The structure of the adenoviral genome is described on the basis of the order in which the viral genes are expressed following host cell transduction. More specifically, the viral genes are referred to as early (E) or late (L) genes according to whether transcription occurs prior to or after onset of DNA replication. In the early phase of transduction, the E1A, E1B, E2A, E2B, E3 and E4 genes of adenovirus are expressed to prepare the host cell for viral replication. The E1 gene is considered a master switch, it acts as a transcription activator and is involved in both early and late gene transcription. E2 is involved in DNA replication; E3 is involved in immune modulation and E4 regulates viral mRNA metabolism. During the late phase of infection, expression of the late genes L1-L5, which encode the structural components of the viral particles, is activated. Late genes are transcribed from the Major Late Promoter (MLP) with alternative splicing.

Adenovirus Capsid Proteins and their Encoding Polynucleotides

As outlined above, the adenoviral capsid comprises three major proteins, hexon, penton and fiber. The hexon accounts for the majority of the structural components of the capsid, which consists of 240 trimeric hexon capsomeres and 12 penton bases. The hexon has three conserved double barrels, while the top has three towers, each tower containing a loop from each subunit that forms most of the capsid. The base of hexon is highly conserved between adenoviral serotypes, while the surface loops are variable.

The penton is another adenoviral capsid protein that forms a pentameric base to which fiber attaches. The trimeric fiber protein protrudes from the penton base at each of the 12 vertices of the capsid and is a knobbed rod-like structure. A remarkable difference in the surface of adenovirus capsids compared to that of most other icosahedral viruses is the presence of the long, thin fiber protein. The primary role of the fiber protein is the tethering of the viral capsid to the cell surface via its interaction with a cellular receptor.

The fiber proteins of many adenovirus serotypes share a common architecture: an N-terminal tail, a central shaft made of repeating sequences, and a C-terminal globular knob domain (or "head"). The central shaft domain consists of a variable number of beta-repeats. The beta-repeats connect to form an elongated structure of three intertwined spiralling strands that is highly rigid and stable. The shaft connects the N-terminal tail with the globular knob structure, which is responsible for interaction with the target cellular receptor. The globular nature of the adenovirus knob domain presents large surfaces for binding the receptor laterally and apically. The effect of this architecture is to project the receptor-binding site far from the virus capsid, thus freeing the virus from steric constraints presented by the relatively flat capsid surface.

Although fibers of many adenovirus serotypes have the same overall architecture, they have variable amino acid sequences that influence their function as well as structure. For example, a number of exposed regions on the surface of the fiber knob present an easily adaptable receptor binding site. The globular shape of the fiber knob allows receptors to bind at the sides of the knob or on top of the fiber knob. These binding sites typically lie on surface-exposed loops connecting beta-strands that are poorly conserved among human adenoviruses. The exposed side chains on these loops give the knob a variety of surface features while preserving the tertiary and quaternary structure. For example, the electrostatic potential and charge distributions at the knob surfaces can vary due to the wide range of isoelectric points in the fiber knob sequences, varying from a pl of approximately 9 for adenovirus "Ad" 8, Ad 19, and Ad 37 to approximately 5 for subgroup B adenoviruses. As a structurally complex virus ligand, the fiber protein allows the presentation of a variety of binding surfaces (knob) in a number of orientations and distances (shaft) from the viral capsid.

One of the most obvious variations between some serotypes is fiber length. Studies have shown that the length of the fiber shaft strongly influences the interaction of the knob and the virus with its target receptors. Further, fiber proteins between serotypes can also vary in their ability to bend. Although beta-repeats in the shaft form a highly stable and regular structure, electron microscopy (EM) studies have shown distinct hinges in the fiber. Analysis of the protein sequence from several adenovirus serotype fibers pinpoints a disruption in the repeating sequences of the shaft at the third beta-repeat from the N-terminal tail, which correlates strongly with one of the hinges in the shaft, as seen by EM. The hinges in the fiber allow the knob to adopt a variety of orientations relative to the virus capsid, which may circumvent steric hindrances to receptor engagement requiring the correct presentation of the receptor binding site on the knob. For example, the rigid fibers of subgroup D adenoviruses require a flexible receptor or one prepositioned for virus attachment, as they themselves are unable to bend.

The identification of specific cell receptors for different Ad serotypes and the knowledge of how they contribute to tissue tropism have been achieved through the use of fiber pseudotyping technology. Although Ads of some subgroups use the Coxsackievirus and adenovirus receptor ("CAR") as a primary receptor, it is becoming clear that many Ads use alternate primary receptors, leading to vastly different tropism in vitro and in vivo. The fibers of these serotypes show clear differences in their primary and tertiary structures, such as fiber shaft rigidity, the length of the fiber shaft, and the lack of a CAR binding site and/or the putative HSPG binding motif, together with the differences in net charge within the fiber knob. Pseudotyping Ad 5 particles with an alternate fiber shaft and knob therefore provides an opportunity to remove important cell binding domains and, in addition, may allow more efficient (and potentially more cell-selective) transgene delivery to defined cell types compared to that achieved with Ad 5. Neutralization of fiber-pseudotyped Ad particles may also be reduced if the fibers used are from Ads with lower seroprevalence in humans or experimental models, a situation that favours successful administration of the vector. Furthermore, full length fiber as well as isolated fiber knob regions, but not hexon or penton alone, are capable of inducing dendritic cell maturation and are associated with induction of a potent CD8+ T cell response. Taken together, adenoviral fiber protein plays an important role in at least receptor-binding and immunogenicity of adenoviral vectors.

Adenoviral Replication

Historically, adenovirus vaccine development has focused on defective, non-replicating vectors. They are rendered replication defective by deletion of the E1 region genes, which are essential for replication. Typically, non-essential E3 region genes are also deleted to make room for exogenous transgenes. An expression cassette comprising the transgene under the control of an exogenous promoter is then inserted. These replication-defective viruses are then produced in E1-complementing cells.

The term "replication-defective" or "replication-incompetent" adenovirus refers to an adenovirus that is incapable of replication because it has been engineered to comprise at least a functional deletion (or "loss-of-function" mutation), i.e. a deletion or mutation which impairs the function of a gene without removing it entirely, e.g. introduction of artificial stop codons, deletion or mutation of active sites or interaction domains, mutation or deletion of a regulatory sequence of a gene etc, or a complete removal of a gene encoding a gene product that is essential for viral replication, such as one or more of the adenoviral genes selected from E1A, E1B, E2A, E2B, E3 and E4 (such as E3 ORF1, E3 ORF2, E3 ORF3, E3 ORF4, E3 ORF5, E3 ORF6, E3 ORF7, E3 ORF8, E3 ORF9, E4 ORF7, E4 ORF6, E4 ORF4, E4 ORF3, E4 ORF2 and/or E4 ORF1). Suitably, E1 and optionally E3 and/or E4 are deleted. If deleted, the aforementioned deleted gene region will suitably not be considered in the alignment when determining percent identity with respect to another sequence.

The term "replication-competent" adenovirus refers to an adenovirus which can replicate in a host cell in the absence of any recombinant helper proteins comprised in the cell. Suitably, a "replication-competent" adenovirus comprises intact structural genes and the following intact or functionally essential early genes: E1A, E1B, E2A, E2B and E4. Wild type adenoviruses isolated from a particular animal will be replication competent in that animal.

Vectors of the Invention

Viral vectors based on non-human simian adenovirus represent an alternative to the use of human derived vectors for gene therapy and genetic vaccines. Certain adenoviruses isolated from non-human simians are closely related to adenoviruses isolated from humans, as demonstrated by their efficient propagation in cells of human origin. As humans develop little or no immunity to simian adenoviruses, they promise to provide an improved alternative to human adenoviral uses.

The term "vector" refers to at least one polynucleotide or to a mixture of at least one polynucleotide and at least one polypeptide capable of introducing the polynucleotide into a cell. "Low seroprevalence" may mean having a reduced pre-existing neutralizing antibody level as compared to human adenovirus 5 (Ad5). Similarly or alternatively, "low seroprevalence" may mean less than about 35% seroprevalence, less than about 30% seroprevalence, less than about 20% seroprevalence, less than about 15% seroprevalence, less than about 10% seroprevalence, less than about 5% seroprevalence, less than about 4% seroprevalence, less than about 3% seroprevalence, less than about 2% seroprevalence, less than about 1% seroprevalence or no detectable seroprevalence. Seroprevalence can be measured as the percentage of individuals having a clinically relevant neutralizing titer (defined as a 50% neutralisation titer >200) using methods as described in Hum. Gene Ther. (2004) 15:293.

In one embodiment, the adenoviral vector of the present invention is derived from a nonhuman simian adenovirus, also referred to as a "simian adenovirus." Numerous adenoviruses have been isolated from nonhuman simians such as chimpanzees, bonobos, rhesus macaques, orangutans and gorillas. Vectors derived from these adenoviruses can induce strong immune responses to transgenes encoded by these vectors. Certain advantages of vectors based on nonhuman simian adenoviruses include a relative lack of cross-neutralizing antibodies to these adenoviruses in the human target population, thus their use overcomes the pre-existing immunity to human adenoviruses. For example, some simian adenoviruses have no cross reactivity with preexisting human neutralizing antibodies and cross-reaction of certain chimpanzee adenoviruses with pre-existing human neutralizing antibodies is only present in 2% of the target population, compared with 35% in the case of certain candidate human adenovirus vectors (Sci. Transl. Med. (2012) 4:1).

Adenoviral vectors of the invention may be derived from a non-human adenovirus, such as a simian adenovirus, e.g., from chimpanzees (*Pan troglodytes*), bonobos (*Pan paniscus*), gorillas (*Gorilla gorilla*) and orangutans (*Pongo abelii* and *Pongo pygnaeus*). They include adenoviruses from Group B, Group C, Group D, Group E and Group G. Chimpanzee adenoviruses include, but are not limited to ChAd3, ChAd15, ChAd19, ChAd25.2, ChAd26, ChAd27, ChAd29, ChAd30, ChAd31, ChAd32, ChAd33, ChAd34, ChAd35, ChAd37, ChAd38, ChAd39, ChAd40, ChAd63, ChAd83, ChAd155, ChAd157, ChAdOx1, ChAdOx2 and SadV41. Alternatively, adenoviral vectors may be derived from nonhuman simian adenoviruses isolated from bonobos, such as PanAd1, PanAd2, PanAd3, Pan 5, Pan 6, Pan 7 (also referred to as C7) and Pan 9. Vectors may include, in whole or in part, a nucleotide encoding the fiber, penton or hexon of a non-human adenovirus.

In a preferred embodiment of the invention, the simian is a chimpanzee. In some embodiments of the invention the replication competent chimpanzee adenoviral vector further comprises a nucleotide sequence encoding a chimpanzee adenoviral fiber polypeptide or functional derivative thereof and/or a chimpanzee adenoviral E4 region.

In an embodiment of the invention, the vector is an adenovirus with a low seroprevalence in humans, where "low seroprevalence" is less than 30% in human subjects. In an embodiment of the adenoviral vectors of the invention, the adenovirus has a seroprevalence of less than 30% in human subjects, preferably no seroprevalence in human subjects and more preferably no seroprevalence in human subjects that have not previously been in contact with a chimpanzee adenovirus.

The choice of gene expression cassette insertion sites of replication defective vectors has been primarily focused on replacing regions known to be involved in viral replication. The choice of gene expression cassette insertion sites of replication competent vectors must preserve the replication machinery. Viruses maximize their coding capacity by generating highly complex transcription units controlled by multiple promoters and alternative splicing. Consequently, replication competent viral vectors must preserve the sequences necessary for replication while allowing room for functional expression cassettes.

In a preferred embodiment, the simian adenoviral vector of the invention is ChAd155 or ChAd83.

In embodiments of the adenoviral vectors of the invention, the adenoviral DNA is capable of entering a mammalian target cell, i.e. it is infectious. An infectious recombinant adenovirus of the invention can be used as a prophylactic or therapeutic vaccine and for gene therapy. Thus, in an embodiment, the recombinant adenovirus comprises an endogenous molecule for delivery into a target cell. The target cell is a mammalian cell, e.g. a bovine cell, a canine cell, a caprine cell, a cervine cell, a chimpanzee cell, a chiroptera cell, an equine cell, a feline cell, a human cell, a lupine cell, an ovine cell, a porcine cell, a rodent cell, an ursine cell or a vulpine cell. For example, the endogenous molecule for delivery into a target cell can be an expression cassette.

According to the invention there is a replication competent simian adenoviral vector comprising an expression cassette which comprises a promoter and a transgene, wherein the expression cassette is inserted in the E3 region, the HE1 site or the HE2 site of the vector. The vector comprises the E1 region or fragments thereof necessary for replication.

In one embodiment, the promoter is chosen from a CASI promoter and an enhanced cytomegalovirus promoter.

In a further embodiment, the expression cassette may further comprise a posttranscriptional regulatory element, and the posttranscriptional regulatory element may be a Woodchuck Hepatitis Postranscriptional Regulatory Element.

In another embodiment, the transgene is an antigen. The antigen may be chosen from a rabies virus antigen, a respiratory syncytial virus antigen, a human immunodeficiency virus antigen, a tuberculosis antigen, a malaria antigen, a hepatitis C virus antigen, a Chikungunya antigen and a hepatitis B virus antigen.

In embodiments of the invention, the E1 region or fragments thereof necessary for replication are present and the exogenous sequence of interest is inserted into the fully or partially deleted E3 region. In an embodiment, the vector comprises a left ITR region, followed by an E1 region, then the E3 region, which is substituted with an expression cassette comprising a promoter, an antigen of interest and, optionally, additional enhancer elements; these are followed by a fiber region, an E4 region and a right ITR; translation occurs in a rightward direction. In a further embodiment, the promoter is a CMV promoter. In a yet further embodiment, the enhancer element is the Hepatitis B Postranslational Regulatory Element (HPRE) or the Woodchuck Hepatitis Postranslational Element (WPRE).

In other embodiments, the vector comprises a left ITR region; followed by an E1 region; a fully or partially deleted E3 region; a fiber region; an E4 region; an expression cassette comprising a promoter, an antigen of interest and, optionally, one or more enhancer elements inserted at the HE1 site, i.e., between the stop codons of the fiber gene and an E4 region ("the HE1 site"); followed by a right ITR. The ChAd155 HE1 insertion site is between bp 34611 and 34612 of the wild type ChAd155 sequence. The ChAd83 HE1 insertion site is between bp 33535 and 33536 of the wild type ChAd83 sequence. Translation occurs in a rightward direction. In a further embodiment, the promoter is a CASI promoter. In a yet further embodiment, the enhancer element is HPRE or WPRE.

In further embodiments, the vector comprises a left ITR region; followed by an E1 region; a fully or partially deleted E3 region; a fiber region; an E4 region; an expression cassette comprising a promoter, an antigen of interest and, optionally, one or more enhancer elements inserted at the HE2 site, i.e., between the end of the left ITR and the cap site of the E4 mRNA ("the HE2 site"); followed by a right ITR. The ChAd155 HE2 insertion site is between bp 37662 and 37663 of the wild type ChAd155 sequence. The ChAd83 HE2 insertion site is between bp 36387 and 36388 of the wild type ChAd83 sequence.

Translation occurs in a leftward direction. In a further embodiment, the promoter is a CASI promoter. In a yet further embodiment, the enhancer element is HPRE or WPRE.

The HE1 and HE2 sites were identified as insertion sites for a transgene, as the insertion in these specific points does not interrupt the coding sequences or regulatory sequences of ChAd155 and ChAd83. Therefore, inserting expression cassettes in the HE1 or HE2 sites of the ChAd genome does not affect the viral replication cycle.

In an embodiment of the invention, the vector is a functional or an immunogenic derivative of an adenoviral vector. By "derivative of an adenoviral vector" is meant a modified version of the vector, e.g., one or more nucleotides of the vector are deleted, inserted, modified or substituted.

Regulatory Elements

Regulatory elements, i.e., expression control sequences, include appropriate transcription initiation, termination, promoter and enhancer sequences; efficient RNA processing signals such as splicing and polyadenylation (poly A) signals including rabbit beta-globin polyA; tetracycline regulatable systems, microRNAs, posttranscriptional regulatory elements e.g., WPRE, posttranscriptional regulatory element of woodchuck hepatitis virus); sequences that stabilize cytoplasmic mRNA; sequences that enhance translation efficiency (e.g., Kozak consensus sequence); sequences that enhance protein stability; and when desired, sequences that enhance secretion of an encoded product.

A "promoter" is a nucleotide sequence that permits the binding of RNA polymerase and directs the transcription of a gene. Typically, a promoter is located in a non-coding region of a gene, proximal to the transcriptional start site. Sequence elements within promoters that function in the initiation of transcription are often characterized by consensus nucleotide sequences. Examples of promoters include, but are not limited to, promoters from bacteria, yeast, plants, viruses, and mammals, including simians and humans. A great number of expression control sequences, including promoters which are internal, native, constitutive, inducible and/or tissue-specific, are known in the art and may be utilized.

Promoters of the invention will typically be heterologous promoters. "Heterologous" means derived from a genotypically distinct entity from that of the rest of the entity to which it is being compared. Promoters of the invention can be constitutive or inducible. Constitutive promoters initiate RNA synthesis independently from regulatory influences. Inducible promoters allow regulation of gene expression and can be regulated by exogenously supplied compounds, environmental factors such as temperature, or the presence of a specific physiological state.

Promoters of the invention include, but are not limited to, CMV promoters, beta-actin promoters, e.g., chicken beta actin (CAG) promoters, CASI promoters, human phosphoglycerate kinase-1 (PGK) promoters, TBG promoters, retroviral Rous sarcoma virus LTR promoters, SV40 promoters, dihydrofolate reductase promoters, phosphoglycerol kinase (PGK) promoters, EF1a promoters, zinc-inducible sheep metallothionine (MT) promoters, dexamethasone (Dex)-inducible mouse mammary tumor virus (MMTV) promoters, T7 polymerase promoter systems, ecdysone insect promoters, tetracycline-repressible systems, tetracycline-inducible systems, RU486-inducible systems and rapamycin-inducible systems.

The transgene may be operably linked to a tissue-specific promoter. For instance, if expression in skeletal muscle is desired, a promoter active in muscle should be used. These include the promoters from genes encoding skeletal beta-actin, myosin light chain 2A, dystrophin, muscle creatine kinase, as well as synthetic muscle promoters with activities higher than naturally occurring promoters. Examples of promoters that are tissue-specific are known for liver, e.g., albumin, hepatitis B virus core, alpha-fetoprotein (AFP); bone, e.g., osteocalcin, bone sialoprotein; lymphocytes, e.g., CD2, immunoglobulin heavy chain and T cell receptor chain; and neuronal, e.g., neuron-specific enolase (NSE).

Optionally, vectors carrying transgenes encoding therapeutically useful or immunogenic products may also include selectable markers or reporter genes. The reporter gene may be chosen from those known in the art. Suitable reporter genes include, but are not limited to enhanced green fluorescent protein, red fluorescent protein, luciferase and secreted embryonic alkaline phosphatase (seAP), which may include sequences encoding geneticin, hygromicin or purimycin resistance, among others. Such selectable reporters or marker genes (which may or may not be located outside the viral genome to be packaged into a viral particle) can be used to signal the presence of the plasmids in bacterial cells, such as ampicillin resistance. Other components of the vector may include an origin of replication.

Suitable promoters include the cytomegalovirus (CMV) promoter and the CASI promoter. The CMV promoter is strong and ubiquitously active. It has the ability to drive high levels of transgene expression in many tissue types and is well known in the art. The CMV promoter can be used in vectors of the invention, either with or without a CMV enhancer.

The CASI promoter is a synthetic promoter described as a combination of the CMV enhancer, the chicken beta-actin promoter, and a splice donor and splice acceptor flanking the ubiquitin (UBC) enhancer (U.S. Pat. No. 8,865,881).

In some embodiments, the CASI promoter can include a nucleic acid sequence having at least about 90%, at least about 95%, at least about 96%, at least about 97%, at least about 98%, at least about 99%, or more, sequence identity to SEQ ID NO: 3. In some embodiments, the promoter comprises or consists of a nucleic acid sequence of SEQ ID NO: 3. In some embodiments, the enhanced hCMV promoter can include a nucleic acid sequence having at least about 90%, at least about 95%, at least about 96%, at least about 97%, at least about 98%, at least about 99%, or more, sequence identity to SEQ ID NO: 4. In some embodiments, the promoter comprises or consists of a nucleic acid sequence of SEQ ID NO: 4.

Suitable promoters also include, but are not limited to, the chimpanzee Elongation Factor 1 promoter (chEF1), a strongly active and ubiquitous promoter, yielding persistent expression of transgenes in vivo. In an embodiment, the promoter is a human ferritin light chain promoter with a CMV enhancer. In this embodiment, the 5'UTRs of the ferritin heavy and light chains are replaced by the 5' UTR of chimpanzee elongation factor 1 alpha, to eliminate iron regulation by ferritin. In an embodiment, the promoter is a chicken beta actin promoter with a CMV enhancer. In an embodiment, the promoter is a hybrid promoter. In an embodiment, the hybrid promoter is a CMV promoter with a CMV enhancer and the ubiquitin gene enhancer, and is a stronger promoter than a conventional CMV promoter.

A "posttranscriptional regulatory element," as used herein, is a DNA sequence that, when transcribed, enhances the expression of the transgene(s) or fragments thereof that are delivered by viral vectors of the invention. Postranscriptional regulatory elements include, but are not limited to the Hepatitis B Virus Postranscriptional Regulatory Element (HPRE) and the Woodchuck Hepatitis Postranscriptional Regulatory Element (WPRE). The WPRE is a tripartite cis-acting element that has been demonstrated to enhance transgene expression driven by certain, but not all promoters.

In embodiments of the invention, a ChAd155 vector may comprise one or more of a promoter, an enhancer, and a reporter gene. For example, vectors of the invention may comprise ChAd155-enhanced hCMV-SeAP, ChAd155-CASI-seAP and ChAd155-hCMV-seAP, optionally with a tetracycline on/off transcriptional control and ChAd155-CMV-hFerL-chEF1-seAP with a tetracycline on/off transcriptional control.

In embodiments of the invention, a ChAd83 vector may comprise one or more of a promoter, an enhancer, and a reporter gene. For example, vectors of the invention may comprise ChAd83 enhanced hCMV SeAP, ChAd83 enhanced hCMV SeAP, ChAd83-CASI-seAP and ChAd83-hCMV-seAP, optionally with a tetracycline on/off transcriptional control and ChAd83-CMV-hFerL-chEF1-seAP with a tetracycline on/off transcriptional control.

Vectors of the invention are generated using techniques provided herein, in conjunction with techniques known to those of skill in the art. Such techniques include conventional cloning techniques of cDNA such as those described in texts, use of overlapping oligonucleotide sequences of the adenovirus genomes, polymerase chain reaction, and any suitable method which provides the desired nucleotide sequence.

Transgenes Adenoviral vectors may be used to deliver desired RNA or protein sequences, for example heterologous sequences, for in vivo expression. A vector of the invention may include any genetic element, including naked DNA, a phage, transposon, cosmid, episome, plasmid or viral component. Vectors of the invention may contain simian adenoviral DNA and an expression cassette. An "expression cassette" comprises a transgene and regulatory elements necessary for the translation, transcription and/or expression of the transgene in a host cell.

A "transgene" is a nucleic acid sequence, heterologous to the vector sequences flanking the transgene, which encodes a polypeptide of interest. The nucleic acid coding sequence is operatively linked to regulatory components in a manner which permits transgene transcription, translation, and/or expression in a host cell. In embodiments of the invention, the vectors express transgenes at a therapeutic or a prophylactic level. A "functional derivative" of a transgenic polypeptide is a modified version of a polypeptide, e.g., wherein one or more amino acids are deleted, inserted, modified or substituted.

The transgene may be used for prophylaxis or treatment, e.g., as a vaccine for inducing an immune response, to correct genetic deficiencies by correcting or replacing a defective or missing gene, or as a cancer therapeutic. As used herein, induction of an immune response refers to the ability of a protein to induce a T cell and/or a humoral antibody immune response to the protein.

The immune response elicited by the transgene may be an antigen specific B cell response, which produces neutralizing antibodies. The elicited immune response may be an antigen specific T cell response, which may be a systemic and/or a local response. The antigen specific T cell response may comprise a CD4+ T cell response, such as a response involving CD4+ T cells expressing cytokines, e.g. interferon gamma (IFN gamma), tumor necrosis factor alpha (TNF alpha) and/or interleukin 2 (IL2). Alternatively, or additionally, the antigen specific T cell response comprises a CD8+ T cell response, such as a response involving CD8+ T cells expressing cytokines, e.g., IFN gamma, TNF alpha and/or IL2.

Transgenes of the invention include, but are not limited to, rabies virus antigens, e.g., rabies glycoprotein (RG), respiratory syncytial virus (RSV) antigens, human immunodeficiency virus (HIV) antigens, tuberculosis antigens, malaria antigens hepatitis C viral (HCV) antigens, Chikungunya antigens and hepatitis B (HBV) antigens.

The composition of the transgene sequence will depend upon the use to which the resulting vector will be put. In an embodiment, the transgene is a sequence encoding a product which is useful in biology and medicine, such as a prophylactic transgene, a therapeutic transgene or an immunogenic transgene, e.g., protein or RNA. Protein transgenes include antigens. Antigenic transgenes of the invention induce an immunogenic response to a disease causing organism. RNA transgenes include tRNA, dsRNA, ribosomal RNA, catalytic RNAs, and antisense RNAs. An example of a useful RNA sequence is a sequence which extinguishes expression of a targeted nucleic acid sequence in the treated animal.

Alternatively, a transgene sequence may include a reporter sequence, which upon expression produces a detectable signal. Such reporter sequences include, without limitation, DNA sequences encoding beta-lactamase, beta-galactosidase (LacZ), alkaline phosphatase, thymidine kinase, green fluorescent protein (GFP), chloramphenicol acetyltransferase (CAT), luciferase, membrane bound proteins including, for example, CD2, CD4, CD8, the influenza hemagglutinin protein, and others well known in the art, to which high affinity antibodies directed thereto exist or can be produced by conventional means, and fusion proteins comprising a membrane bound protein appropriately fused to an antigen tag domain from, among others, hemagglutinin or Myc. These coding sequences, when associated with regulatory elements which drive their expression, provide signals detectable by conventional means, including enzymatic, radiographic, colorimetric, fluorescence or other spectrographic assays, fluorescent activating cell sorting assays and immunological assays, including enzyme linked immunosorbent assay (ELISA), radioimmunoassay (RIA) and immunohistochemistry.

As a result of the redundancy in the genetic code, a polypeptide can be encoded by a variety of different nucleic acid sequences. Coding is biased to use some synonymous codons, i.e., codons that encode the same amino acid, more than others. By "codon optimized," it is meant that modifications in the codon composition of a recombinant nucleic acid are made without altering the amino acid sequence. Codon optimization has been used to improve mRNA expression in different organisms by using organism-specific codon-usage frequencies.

In addition to, and independently from, codon bias, some synonymous codon pairs are used more frequently than others. This codon pair bias means that some codon pairs are overrepresented and others are underrepresented. Codon pair deoptimization has been used to reduce viral virulence. For example, it has been reported that polioviruses modified to contain underrepresented codon pairs demonstrated decreased translation efficiency and were attenuated compared to wild type poliovirus (Science (2008) 320:1784). Engineering a synthetic attenuated virus by codon pair deoptimization can produce viruses that encode the same amino acid sequences as wild type but use different pairwise arrangements of synonymous codons. Viruses attenuated by codon pair deoptimization generated up to 1000-fold fewer plaques compared to wild type, produced fewer viral particles and required about 100 times as many viral particles to form a plaque.

In contrast, polioviruses modified to contain codon pairs that are overrepresented in the human genome acted in a manner similar to wild type RNA and generated plaques identical in size to wild type RNA (Coleman et al. (2008) Science 320:1784). This occurred despite the fact that the virus with overrepresented codon pairs contained a similar number of mutations as the virus with underrepresented codon pairs and demonstrated enhanced translation compared to wild type. This observation suggests that codon pair optimized constructs would be expected to act in a manner similar to their non-codon pair optimized counterparts and would not be expected to provide a functional advantage.

A construct of the invention may comprise a codon optimized nucleic acid sequence. Alternatively or additionally, a vector of the invention comprises a codon optimized sequence of a transgene or an immunogenic derivative or fragment thereof. A construct of the invention may comprise a codon pair optimized nucleic acid sequence. Alternatively or additionally, a vector of the invention comprises or consists of a codon pair optimized sequence of a transgene or an immunogenic derivative or fragment thereof.

Delivery of Replication Competent Adenoviral Vectors

In some embodiments, the recombinant adenovirus of the invention is administered to a subject by epicutaneous administration, intradermal administration, intramuscular injection, intraperitoneal injection, intravenous injection, mucosal administration, nasal administration, oral administration, rectal administration, subcutaneous injection, transdermal administration or intravaginal administration.

If the therapeutic regimen involves co-administration of one or more adenoviral vectors and a further component, each formulated in different compositions, they are favorably administered co-locationally at or near the same site. For example, the components can be administered (e.g. via an administration route selected from intramuscular, transdermal, intradermal, sub-cutaneous) to the same side or extremity ("co-lateral" administration) or to opposite sides or extremities ("contra-lateral" administration).

In an embodiment of the invention, the vectors can be administered intramuscularly (IM), i.e., injection directly into muscle. Muscles are well vascularized and the uptake is typically rapid.

In an embodiment of the invention, the vectors can be administered orally. Oral vaccine delivery offers several advantages over intramuscular delivery, including elimination of pain at the injection site, ease of delivery and convenience. It allows less qualified health care workers to effectively administer the vaccine and circumvents the possibility of contaminated needles and syringes in areas with a high prevalence of, e.g., HIV, hepatitis B and hepatitis C.

The oral mucous membrane is composed of an outer layer of stratified squamous epithelia, which are mostly non-keratinized, and an underlying layer of dense connective tissue, the lamina propria. The lamina propria comprises many immune cells and is a site where immune responses occur as a barrier to protect internal tissues from pathogenic organisms.

Administration via the oral/gastrointestinal route provides an antigen with access to a large surface area through a single cell layer of simple, columnar epithelium, where it targets Peyer's Patches and induces a systemic response.

Live replication competent adenoviruses have been successfully administered orally for decades but the administration of viral vectors encoding antigenic transgenes is more challenging. Mechanisms of immune recognition are not easily accessible to the luminal side of the intestine; this protects the body from mounting immune responses to ingested proteins in food. Thus, constructs of the invention face the obstacle of raising immune responses to protein antigens when delivered to the intestine via an oral route. For example, in a phase 1 study, human subjects were dosed orally with a replication competent live human Ad4 vaccine with an influenza hemagglutinin antigen as a transgene. They responded with a cellular immune response but did not mount a humoral antibody response until boosted intramuscularly (Lancet Infect Dis (2013) 13:238). Similarly, conventional pigs were dosed either orally or subcutaneously with a replication competent live recombinant pig adenovirus vaccine with a swine fever virus antigen as a transgene. None of the pigs dosed orally, but 75% of the pigs dosed subcutaneously, developed antibodies against the transgenic antigen (Vaccine (2001) 146:1787).

In an embodiment of the invention, the vectors can be administered mucosally. Mucosal vaccine delivery also offers several advantages to intramuscular delivery of vaccines. As the mucosa is contiguous with the outside of the body, mucosal vaccines can be effective and safe at a slightly lower degree of purity compared to parenteral vaccines, thus they are easier to produce. They are also typically effective at low doses, thus are cost-effective.

"Mucosal" delivery as used herein encompasses all mucus membranes. Mucosa typically line body cavities and passages that comprise epithelium and lamina propria. Mucosa can be keratinized or non-keratinized. Mucosal tissues include, but are not limited to, alveolar, bronchial, buccal, dermal, endometrial, gastric, intestinal, jugal, lining, masticatory, nasal, olfactory, oral, otic, palatine, rectal, specialized (tongue), sublingual, tracheal and vaginal mucosas.

Mucus membranes provide a highly specialized immune system comprised of lymphoid microcompartments such as the Peyer's patches, mesenteric lymph nodes, appendix, tonsils and adenoids. Antigens taken up by absorptive epithelial cells of the mucosa can be shuttled to, or directly presented to antigen presenting cells and presented to T cells.

Immune responses in mucosal tissues are determined by the nature of the antigen, the types of antigen presenting cells and the local microenviroment. Sensitized mucosal B and T cells leave the site of the initial antigen encounter, transit through the lymph and enter the circulation. Mucosal delivery can be, for example, buccal, genital, e.g., vaginal, intranasal, ocular, e.g., eye conjunctival, otic, e.g., inner ear, rectal or sublingual.

In an embodiment of the invention, the vectors can be administered sublingually. Vaccine delivery via the sublingual route provides an antigen with fast access through a very thin layer of stratified, squamous non-keratinized epithelium, where it targets Langerhans cells and induces a systemic response. Antigen delivered under the tongue becomes available to a dense network of dendritic cells in the sublingual mucosa. Replication competent vectors delivered sublingually bypass the liver, thus avoiding first-pass metabolism, increasing their persistence, thus potentially generating a stronger immune response.

In an embodiment of the invention, the vectors can be administered buccally. Vaccine delivery via the buccal route also provides an antigen with access through a layer of stratified, squamous non-keratinized epithelium which is somewhat thicker than the sublingual layer. Buccal delivery also targets Langerhans cells and induces a systemic response.

Adjuvants

Approaches to establishing strong and lasting immunity to specific pathogens include addition of adjuvants to vaccines. By "adjuvant" is meant an agent that augments, stimulates, activates, potentiates or modulates the immune response to an active ingredient of the composition. The adjuvant effect may occur at the cellular or humoral level, or both.

Adjuvants stimulate the response of the immune system to the actual antigen but have no immunological effect themselves. Alternatively or additionally, adjuvanted compositions of the invention may comprise one or more immunostimulants. By "immunostimulant" it is meant an agent that induces a general, temporary increase in a subject's immune response, whether administered with the antigen or separately.

A composition of the invention may be administered with or without an adjuvant. Alternatively or additionally, the composition may comprise, or be administered in conjunction with, one or more adjuvants (e.g. vaccine adjuvants), in particular the composition comprises an immunologically effective amount of a vector of the invention encoding a transgene.

Methods of Use/Uses

Methods are provided for inducing an immune response against a disease caused by a pathogen in a subject in need thereof comprising a step of administering an immunologically effective amount of a construct or composition as disclosed herein. In some embodiments are provided the use of the constructs or compositions disclosed herein for inducing an immune response to a transgenic antigen in a subject in need thereof. Vectors of the invention may be applied for the prophylaxis, treatment or amelioration of diseases due to infection.

Methods of the invention include the use of a vector of the invention in medicine. They include the use of a vector of the invention for the treatment of a disease caused by a pathogen. A vector of the invention can be used in the manufacture of a medicament for treating a disease caused by a pathogen.

Effective immunization with adenoviral vectors depends on the intrinsic immunomodulatory capability of the adenoviral vector backbone. Immunologically less potent adenoviruses induce less antigen expression. Effective immunization also depends on the ability of the promoter to drive strong and sustained transgene expression. For example, adenoviral vectors driven by the viral promoter CMV-IE do not sustain long-term transgene expression because they induce cytokines that dampen expression.

By "subject" is intended a vertebrate, such as a mammal e.g. a human or a veterinary mammal. In some embodiments the subject is human.

General

Vectors of the invention are generated using techniques and sequences provided herein, in conjunction with techniques known to those of skill in the art. Such techniques include conventional cloning techniques of cDNA such as those described in texts, use of overlapping oligonucleotide sequences of the adenovirus genomes, polymerase chain reaction, and any suitable method which provides the desired nucleotide sequence.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. The term "plurality" refers to two or more. Additionally, numerical limitations given with respect to concentrations or levels of a substance, such as solution component concentrations or ratios thereof, and reaction conditions such as temperatures, pressures and cycle times are intended to be approximate. The term "about" used herein is intended to mean the amount ±10%.

The present invention will now be further described by means of the following non-limiting examples.

EXAMPLES

Example 1: Construction of Replication Competent Chimpanzee Adenoviruses

Wild type chimpanzee adenoviruses type 155 (ChAd155) (WO 2016 198621) and type 83 (ChAd83) (WO 2010/086189) were isolated from healthy chimpanzees using standard procedures and were constructed as replication defective viruses as described in Sci Transl Med (2012) 4:1 and WO 2010/086189.

Replication competent ChAd155 and ChAd 83 were each constructed by inserting a transgene expression cassette. The expression cassette components used either the classical human CMV promoter or the CASI promoter, rabies glycoprotein as a model antigen and, optionally, a WPRE enhancer. The insertion sites for the transgene cassette comprised replacing the E3 region, inserting between the fiber and the E4 region (site HE1) and inserting downstream of the right ITR (site HE2).

Figure 1:
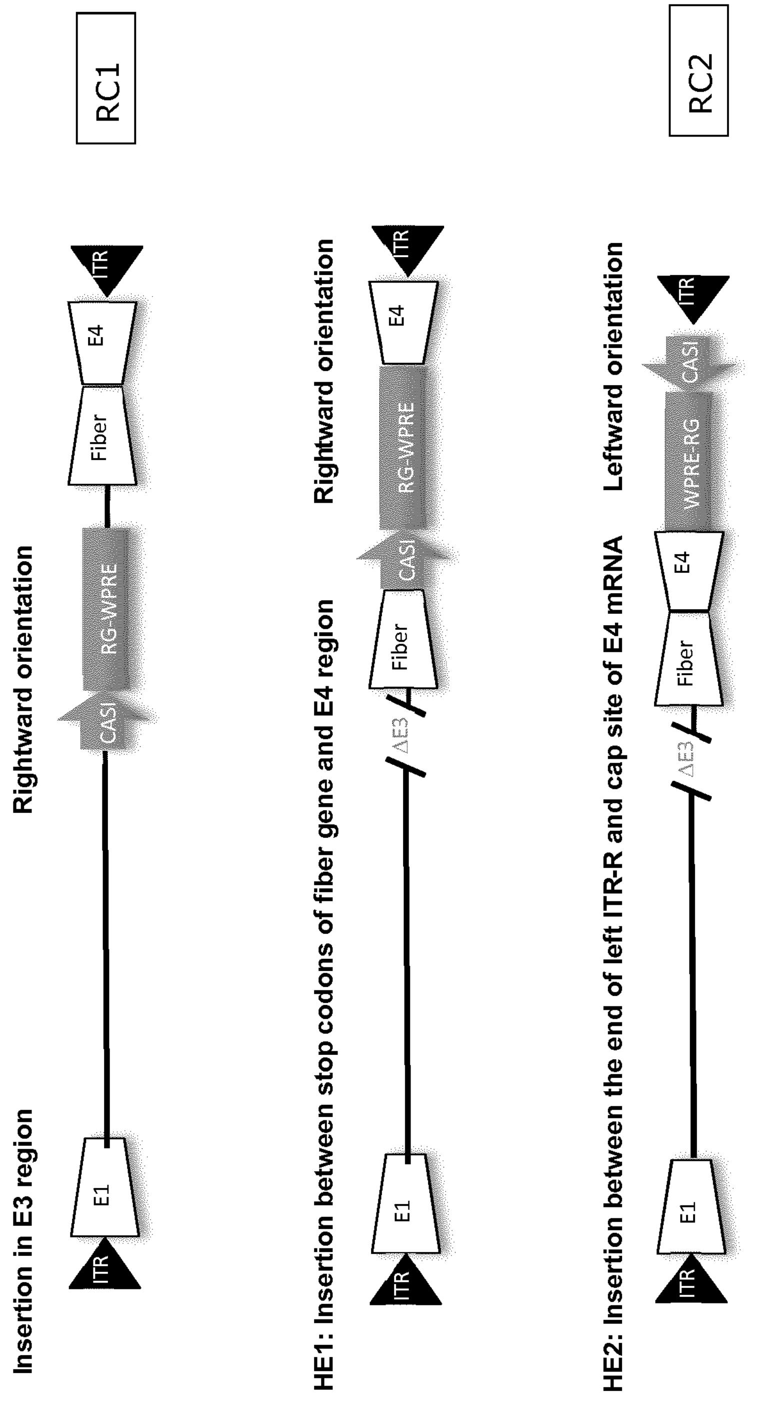
FIG. 1: Replication competent simian adenoviral constructs. Inverted terminal repeats (ITR) flank the 3' and 5' ends; E1 is the early gene 1; CMV is the cytomegalovirus promoter; CASI is the CASI promoter, RG is a model antigen, WPRE is the Woodchuck Hepatitis Postranscriptional Regulatory Element, ΔE3 denotes that the early gene 3 is deleted; fiber denotes the adenoviral gene encoding the fiber protein and E4 is the early gene 4.

The top panel in FIG. 1 illustrates the RC1 vector, in which a transgene cassette replaced the E3 region. The middle panel illustrates a construct in which a transgene cassette was inserted between the stop codons of the fiber gene and the E4 region (site HE1). When the transgene cassette was inserted in site HE1, ChAd155 failed to replicate. However, insertion of a transgene into the HE1 site of ChAd83 produced a viable vector. The bottom panel illustrates the RC2 vector, in which a transgene cassette is inserted downstream of the right ITR (site HE2). The E1 region remains intact in both the RC1 and RC2 configuration. The transgene was inserted by homologous recombination techniques in the following positions of the SEQ ID NO: 1 and of the SEQ ID NO: 2:

HE1 ChAd155: insertion site between bp 34611 and 34612 of SEQ ID NO: 1;

HE2 ChAd155: insertion site between bp 37662 and 37663 of SEQ ID NO: 1;

HE1 ChAd83: insertion site between bp 33535 and 33536 of SEQ ID NO: 2;

HE2 ChAd83: insertion site between bp 36387 and 36388 of SEQ ID NO: 2.

Example 2: Virus Production, Vector Titer and Expression

To identify an animal model in which to evaluate vector replication, the type C replication competent adenovirus ChAd155 RC2 and the type E replication competent adenovirus ChAd83 RC2 vectors were assessed for their ability to replicate, measured by vector titer and genome copy number, in cells of various animal origins. The results are shown in Table 1.

TABLE 1

Replication and Expression of Replication Competent ChAd155 and ChAd83

| Cell line: Species | Vector | Vector Titer | Genome Copy | Expression Day 2 | Expression Day 7 |
|---|---|---|---|---|---|
| MRC5: Human | ChAd155 | +++ | +++ | ++ | ++++ |
| | ChAd83 | +++++ | +++++ | +++ | +++++ |
| PK15: | ChAd155 | +++++ | +++++ | NA | NA |
| Swine | ChAd83 | +++ | ++++ | NA | NA |
| NMuLi: | ChAd155 | ++ | +++ | +++ | +++ |
| Mouse | ChAd83 | ND | + | ++ | ++ |
| Vero: | ChAd155 | ++ | ++++ | +++ | +++ |
| Non-human primate | ChAd83 | ND | + | + | + |

ND = not detectable;
NA = not available

As shown in Table 1, human MRC5 cells and swine PK15 cells produced high vector titers and high genome copy numbers of both replication competent ChAd155 and ChAd83. Murine NMuLi and non-human primate Vero cells also produced RC ChAd155 but to a lesser extent than the human or swine cells. RC ChAd83 failed to grow well in murine NMuLi cells and, surprisingly, in non-human primate Vero cells.

Human MRC5, mouse NMuLi and non-human primate Vero cells supported the expression of RC ChAd155 through day 7. Human MRC5 cells supported the expression of RC ChAd83 through day 7, as did mouse NMuLi and non-human primate Vero cells, but to a lesser extent than the human cells.

Virus Production

FIG. 2 shows the amount of virus produced by human primary MRC5 cells infected with either replication competent ChAd155 or ChAd83, each comprising either RC1 or RC2. The cells were harvested seven days post-infection and the vector titer was evaluated in cell lysates obtained following three freeze-thaw cycles. Vector titers were measured by quantitative PCR (QPCR) analysis with primers designed for the respective promoter regions. The multiplicity of infection (moi) was 1250 virus particles per cell. The virus production is indicated as vector particles/cell, above the bars.

Human MRC5 cells supported production of ChAd155 comprising either RC1 ($2.17\times10^3$ vp/cell) or RC2 ($4.40\times10^3$ vp/cell) and also supported production of ChAd83 comprising either RC1 ($1.18\times10^4$ vp/cell) or RC2 ($1.06\times10^5$ vp/cell). As shown in FIG. 2, ChAd83 was produced at a higher level than ChAd155; the ChAd83 vector comprising RC2 was the most robust of the four viral/vector combinations.

Vector Genome Copy Number

After infection, the vector is replicated in the cell and the vector genome copy number can be measured by QPCR. Vector DNA replication can occur even in cells not fully permissive for viral replication and propagation. QPCR of vector DNA provides a measure of vector replication within the infected cell, independently of the ability of the virus to complete the replication cycle and be released as mature viral progeny. Vector replication can thus be quantified in animal species, tissue types and cell types which are not permissive for ChAd virus replication or propagation.

Vector genome copy number was measured in parallel with vector titer and the results shown in FIG. 3. Human MRC5 cells were infected with either ChAd155 or ChAd83, each comprising either RC1 or RC2. The cells were harvested seven days post-infection, the total DNA extracted, the viral genome quantified by QPCR and the results expressed as vector genome copy per cell. The moi was 250 virus particles per cell and the numbers of virus particles per cell are indicated above the bars denoting viral genome copies per cell. The copy number is directly proportional to the level of transgene expression.

As shown in FIG. 3, the amount of viral DNA replication of RC1 ($6.21\times10^3$ vp/cell) and RC2 ($6.71\times10^3$ vp/cell) by ChAd155 was similar. ChAd83 produced more RC1 ($2.76\times10^4$ vp/cell) and RC2 ($9.19\times10^4$ vp/cell) viral DNA than ChAd155. The highest level of viral DNA replication was observed by ChAd83 RC2.

Example 3: Viral Transgene Expression from Human Cells

Western blot analysis was performed to compare the level of transgene expression in replication defective and replication competent ChAd155 (FIG. 4) and ChAd83 (FIG. 5) viral vectors. MRC5 cells were transduced with ChAd155 RC1 or ChAd155 RC2 vector at an moi of either 250 or 1250 viral particles per cell. The cells were harvested at two and seven days post infection, extracts prepared using standard methods and an equivalent amount of extract loaded onto SDS-PAGE gels. Following electrophoretic separation, the proteins were transferred onto nitrocellulose membranes, which were then probed with a commercially available monoclonal antibody to the rabies glycoprotein transgene.

FIG. 4 and FIG. 5 demonstrate that, at both two and seven days post-infection, the replication competent ChAd155 RC (FIG. 4) and ChAd83 RC (FIG. 5) vectors expressed the transgene at a higher level than the replication defective ChAd155 RD and ChAd83 RD vectors, respectively. A band of about 51 kDa, which corresponds to the expected molecular weight of the rabies glycoprotein, indicated by the bar to the left of the blots, was observed upon probing with an antibody to the rabies glycoprotein.

Increasing the moi resulted in an increased transgene expression at both day 2 and day 7 for all vectors tested. With respect to ChAd155, the RC2 vector produced the highest level of transgene expression, followed by ChAd155 RC1, then the ChAd155 RD. With respect to ChAd83, the RC2 vector produced the highest level of transgene expression, followed by ChAd155 RD vector, then ChAd155 RC1.

At day 2 post infection, low levels of expression by ChAd155 were observed by western blot when driven from either the hCMV (RC1) or the CASI (RC2) promoter. Peak expression of the transgene by ChAd83 was observed two days after infection, most likely occurring at this early time point because the ChAd83 vector is cytopathic in MRC5 cells. In addition, ChAd83 expression driven by the CMV promoter in MRC5 cells was not sustained longer than two days because the adeno backbone E enhances promoter shut-off/transcriptional silencing.

By day 7, expression driven by the hCMV promoter increased to a small extent and expression driven by the CASI promoter was greatly increased, and was more robust than expression driven by the hCMV promoter. In contrast, at day 2 post infection, ChAd 83 expression driven by both hCMV and CASI was much higher than that observed with ChAd155. However, by day 7, expression driven by the hCMV promoter had dropped to nearly undetectable levels, while expression driven by the CASI promoter remained constant. Without being constrained by theory, this suggests that while the adeno backbone of ChAd83 (E type adenovirus) enhances promoter shut off, the CASI promoter can overcome the transcriptional silencing.

These studies demonstrate that the RC2 vectors, which comprise a CASI promoter in a leftward orientation, situated in the HE2 locus, express the transgene more robustly than the RC1 vectors, which place a CMV promoter in a rightward orientation situated in a deleted E3 region (FIG. 1).

Example 4: Replication Competent Adenoviral Genome Copy Number

The efficiency of replication competent adenoviral vectors of the invention, expressed as vector copies per cell, was evaluated in cell cultures derived from both mice and non-human primates. FIG. 6 (top panel) shows the genome copy number of replication competent vectors grown in murine hepatic NMuLi cells grown in monolayers and infected with ChAd155 RC1, ChAd155 RC2, ChAd83 RC1 or ChAd83 RC2 at an moi of 250 virus particles per cell. Total DNA was extracted at five days post-infection and the vector replication was measured by QPCR using primers annealing to the vector's promoter region.

The results, expressed as vector copies per cell, are shown in FIG. 6 (top panel). ChAd155 amplified both the RC1 and RC2 vector with high efficiency in NMuLi cells. ChAd155 replicated the RC1 ($1.73\times10^4$) and RC2 ($1.92\times10^4$) vectors to approximately the same degree. ChAd83 was less efficient than ChAd155 in replicating the RC1 and RC2 vectors. ChAd83 replicated the vector DNA only in small amounts in the murine cells. The RC1 vector replicated at a level of $5.47\times10^2$ copies per cell and the RC2 vector at a level of $6.74\times10^2$ copies per cell.

Non-human primate Vero cells were also grown in monolayers and infected with ChAd155 RC1, ChAd155 RC2, ChAd83 RC1 or ChAd83 RC2 (FIG. 6 bottom panel). Two different multiplicities of infection were used: 50 and 250 virus particles per cell. Total DNA was extracted at five days post-infection and the vector replication was measured by QPCR using primers annealing to the vector's promoter region.

The results, expressed as vector copies per cell, are shown in FIG. 6 (bottom panel). The Vero primate cell line was permissive for ChAd155 RC1 ($3.71\times10^3$ copies per cell at an moi of 50 and $4.93\times10^4$ copies per cell at an moi of 250) and ChAd155 RC2 ($8.15\times10^3$ copies per cell at an moi of 50 and $7.05\times10^4$ copies per cell at an moi of 250). The Vero primate cell line was poorly, if at all, permissive for ChAd83 RC1 or ChAd83 RC2. No ChAd83 RC1 or ChAd83 RC2 vectors were detected to be expressed from Vero cells at an moi of 50. At an moi of 250, ChAd83 replicated the RC1 vector at a level of $1.13\times10^2$ copies per cell and the RC2 vector at a level of $1.29\times10^3$ copies per cell.

Example 5: Transgene Expression from Murine and Non-Human Primate Cells

Western blot analysis was performed to compare the level of transgene expression by ChAd155 RC1 and ChAd155 RC2 in murine NMuLi cells (FIG. 7 top panel). The cells were infected with ChAd155 RC1 or ChAd155 RC2 at an moi of 50, 250 or 1250 viral particles per cell. The cells were harvested at two and five days post infection, extracts prepared using standard methods and an equivalent amount of total cell extract loaded onto SDS-PAGE gels. Following electrophoretic separation, the proteins were transferred onto nitrocellulose membranes, which were then probed with a commercially available monoclonal antibody to the rabies glycoprotein transgene.

FIG. 7 (top panel) demonstrates that both ChAd155 RC1 and ChAd155 RC2 express a transgene in murine NMuLi cells. Expression was observed at both two and five days post infection, indicated by the band of about 51 kDa, which corresponds to the expected molecular weight of the rabies glycoprotein (RG). The ChAd155 RC2 vector produced a higher level of transgene expression than the ChAd155 RC1 vector at both two and five days post-infection.

Western blot analysis was then performed to compare the level of transgene expression by ChAd155 RC1, ChAd155 RC2, ChAd83 RC1 and ChAd83 RC2 in murine NMuLi cells (FIG. 7 bottom panel). The cells were infected with ChAd155 RC1, ChAd155 RC2, ChAd83 RC1 or ChAd83 RC2 at an moi of 50, 250 or 1250 viral particles per cell (250 and 1250 for ChAd83 RC1). The cells were processed for western blot as described in FIG. 4.

FIG. 7 (bottom panel) demonstrates that ChAd155 RC1, ChAd155 RC2, ChAd83 RC1 and ChAd83 RC2 express a transgene in murine NMuLi cells. Expression was observed at both two and five days post infection, indicated by the band of about 51 kDa, which corresponds to the expected molecular weight of the rabies glycoprotein (RG). ChAd155 demonstrated more efficient expression of the transgene than ChAd83. At two days post-infection, robust transgene expression by ChAd155 RC2 was observed even at the low moi of 50 vp/cell, whereas robust transgene expression by ChAd155 RC1 was first observed at higher mois. Also, RC2 demonstrated more efficient transgene expression than RC1 in both ChAd155 and ChAd83 viral serotypes. RC2 was more robustly expressed than RC1 in each of the direct comparisons.

Example 6: Immunogenicity of RD and RC1 Vectors in Mice

The immunological potency of the ChAd155 RD vector to induce a T cell response was compared to that of the ChAd155 RC1 and ChAd83 RC1 vectors in Balb/c mice, six mice per group. The vectors were injected intramuscularly at doses of $10^5$ and $10^6$ viral particles.

Three weeks post-immunization, the animals were sacrificed and the splenocytes of immunized mice were isolated and analyzed by IFN-gamma-ELISpot using a rabies glycoprotein T cell epitope. The results are shown in FIG. 8, expressed as IFN-gamma Spot Forming Cells (SFC) per million splenocytes. Each dot represents the response in a single mouse, and the horizontal lines correspond to the geomean for each dose group.

At a dose of $10^6$ vp, all of the mice responded positively, mounting an immune response to the antigenic transgene (FIG. 8). As expected, the immune response was more robust at the higher dose for each of the three vectors. ChAd155 RC1 was more potent in inducing an immune response than either the equivalent ChAd155 RD or the ChAd83 RC1 vector dose.

These results are consistent with the data shown in Example 4 and FIG. 6 demonstrating little or no replication of ChAd83 in mouse NMuLi cells and a lower level of antigen expression compared to the ChAd155 RC1 vector.

Example 7: Immunogenicity of RD and RC1 Vectors Administered Orally to Mice

The immunological potency of the ChAd155-RD and ChAd155 RC1 vectors was evaluated in mice; replication defective and replication competent ChAd155 vectors were compared and the results are shown in FIG. 9. The animals (six per group) were immunized by either an oral or intramuscular route, then evaluated for a neutralizing antibody response (top panel) and a T cell response (bottom panel) to the transgenic antigen.

FIG. 9 (top panel) describes the humoral neutralizing antibody immune response of mice dosed orally with $5\times10^8$ virus particles or intramuscularly with $1\times10^7$ virus particles. At eight weeks post-immunization, neutralizing antibody titers were measured with a fluorescent antibody virus neutralization assay (FAVN) using a commercially available monoclonal antibody to the rabies G protein.

Virus neutralization titers, a measure of the B cell (antibody) response are shown in FIG. 9 (top panel). Each dot represents the response of a single mouse. The top panel of FIG. 9 demonstrates that functional neutralizing antibodies were detected in the serum within eight weeks following a single administration of ChAd155 RD or ChAd155 RC1. When ChAd155 RC1 was administered orally, all six of the mice had a neutralizing antibody titer above the protection threshold (dotted line). An oral administration of ChAd155 RD resulted in four of the six mice producing a neutralizing antibody titer above the protection threshold.

When ChAd155 RC1 was administered intramuscularly, all six of the mice had a neutralizing antibody titer above the protection threshold. An intramuscular administration of ChAd155 RD resulted in five of the six mice generating a neutralizing antibody titer above the protection threshold.

The neutralization titers of the mice immunized with the ChAd155 RC1 vector were higher than those immunized with the ChAd155 RD vector regardless of whether administered orally or IM. This demonstrates that the replication competent ChAd155 vectors of the invention are more effective than the replication defective ChAd155 vectors in inducing an antibody response to a transgenic antigen, whether administered orally or intramuscularly.

T cell response by IFN-gamma secretion was measured by ELISpot in splenocytes of vaccinated animals with the transgenic antigen and is shown in FIG. 9 (bottom panel). Mice were dosed orally with $5\times10^8$ virus particles or intramuscularly with $1\times10^7$ virus particles. At three weeks post-immunization, the T cell response was measured by ELISpot, as described in Example 6. Each dot represents the response of a single mouse.

IFN-gamma secretion, a measure of the T cell (cellular immune) response, is shown in FIG. 9 (bottom panel). Each dot represents the response of a single mouse. FIG. 9 demonstrates that T cell immune response was detected within three weeks post-immunization following a single administration of ChAd155 RD or ChAd155 RC1. When ChAd155 RC1 was administered orally, all six of the mice mounted a T cell response. Oral administration of ChAd155 RD resulted in four of the six mice mounting a T cell response.

The T cell responses of the mice immunized with the ChAd155 RC1 vector were higher than those immunized with the ChAd155 RD vector regardless of whether administered orally or IM. This demonstrates that the replication competent ChAd155 vectors of the invention are more effective than the replication defective ChAd155 vectors in inducing a cellular immune response to a transgenic antigen, whether administered orally or intramuscularly.

Example 8: Immunogenicity of Replication Competent Vectors in Swine

Animals of the genus Sus, commonly known as pigs or swine, provide a relevant model because, based on the in vitro data in PK1 swine cells, they are likely to be permissive for ChAd replication. To demonstrate immunogenicity, pigs, e.g., *Sus scrofa domesticus*, can be immunized with replication competent ChAd155 or ChAd83 vectors delivered intramuscularly or intranasally at a dose of approximately $1\times10^{10}$-$1\times10^{12}$ viral particles. Collected serum samples can be analysed for neutralizing antibodies, T cell response and B cell response. Post-vaccination shedding can be monitored by collecting nasal secretions, saliva or feces. The site from which virus is shed can indicate its biodistribution, e.g., if shedding occurs predominantly from nasal secretions, it can be inferred that the virus has a preference to replicate in the upper respiratory tract. Indications of safety may include measurements of body weight, temperature, food consumption, hematologic parameters and serum chemistry.

Once immunogenicity of the vectors of the invention has been demonstrated in the pig model via intramuscular and intranasal administration, immunogenicity can be tested via other routes, including sublingual administration. The experimental designs may include comparisons of replication competent and replication defective vectors, comparisons of ChAd155 and ChAd 83 vectors, comparisons of promoters, including CASI and CMV promoters in various locations within a construct, comparisons of the effects of various enhancer elements, e.g., WPRE, and comparisons of the sublingual route to other immunization routes.

What is claimed is:

1. A replication competent simian adenoviral vector comprising an expression cassette which comprises a promoter and a transgene, wherein the expression cassette is inserted in the E3 region, the HE1 site or the HE2 site of the vector and wherein the simian is a chimpanzee or a bonobo.

2. The replication competent adenoviral vector of claim 1, wherein the vector comprises a nucleotide sequence encoding one or more of a chimpanzee or bonobo adenoviral fiber polypeptide and a chimpanzee or bonobo adenoviral E4 region.

3. The replication competent simian adenoviral vector of claim 1, wherein the vector is an adenovirus with a low seroprevalence in humans.

4. A replication competent chimpanzee adenoviral vector of claim 1, wherein the vector is ChAd155.

5. A replication competent chimpanzee adenoviral vector of claim 1, wherein the vector is ChAd83.

6. The replication competent simian adenoviral vector of claim 1, wherein the promoter is chosen from a CASI promoter and an enhanced cytomegalovirus promoter.

7. The replication competent simian adenoviral vector of claim 6, wherein the promoter is a CASI promoter.

8. The replication competent simian adenoviral vector of claim 6, wherein the promoter is an enhanced cytomegalovirus promoter.

9. The replication competent simian adenoviral vector of claim 1, wherein the expression cassette further comprises a posttranscriptional regulatory element.

10. The replication competent simian adenoviral vector of claim 9, wherein the posttranscriptional regulatory element is a Woodchuck Hepatitis Postranscriptional Regulatory Element.

11. The replication competent simian adenoviral vector of claim 1, wherein the transgene is an antigen.

12. The replication competent simian adenoviral vector of claim 11, wherein the antigen is chosen from a rabies virus antigen, a respiratory syncytial virus antigen, a human immunodeficiency virus antigen, a tuberculosis antigen, a malaria antigen, a hepatitis C virus antigen, a Chikungunya antigen and a hepatitis B virus antigen.

13. The replication competent simian adenoviral vector of claim 1, wherein the expression cassette is inserted in the E3 region.

14. The replication competent simian adenoviral vector of claim 1, wherein the expression cassette is inserted in the HE1 site.

15. The replication competent simian adenoviral vector of claim 1, wherein the expression cassette is inserted in the HE2 site.

16. The replication competent simian adenoviral vector of claim 1, wherein the vector is administered by intramuscular injection.

17. The replication competent simian adenoviral vector of claim 1, wherein the vector is administered orally.

18. A method of using the replication competent simian adenoviral vector of claim 1 to induce an immune response against a disease caused by a pathogen in a subject in need thereof.

* * * * *